US010675343B2

(12) United States Patent
Michael et al.

(10) Patent No.: US 10,675,343 B2
(45) Date of Patent: *Jun. 9, 2020

(54) VACCINES AND METHODS FOR CREATING A VACCINE FOR INDUCING IMMUNITY TO ALL DENGUE VIRUS SEROTYPES

(71) Applicants: Scott F. Michael, Estero, FL (US); Sharon Isern, Estero, FL (US)

(72) Inventors: Scott F. Michael, Estero, FL (US); Sharon Isern, Estero, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/174,253

(22) Filed: Oct. 29, 2018

(65) Prior Publication Data

US 2020/0129607 A1    Apr. 30, 2020

(51) Int. Cl.
*A61K 39/12* (2006.01)
*A61K 39/00* (2006.01)
*C12N 7/00* (2006.01)
*C07K 14/005* (2006.01)
*A61K 39/295* (2006.01)

(52) U.S. Cl.
CPC .... *A61K 39/12* (2013.01); *A61K 2039/55505* (2013.01); *A61K 2039/55527* (2013.01); *A61K 2039/55538* (2013.01); *A61K 2039/55555* (2013.01)

(58) Field of Classification Search
CPC .......... A61K 39/12; C12N 2770/24134; C12N 7/00; Y02A 50/386; C07K 14/005
See application file for complete search history.

*Primary Examiner* — Barry A Chestnut
(74) *Attorney, Agent, or Firm* — Robert Varkonyi; Zagrebelsky Law P.A.

(57) ABSTRACT

A method to produce a chimeric protein having a flavivirus backbone and portions dengue virus is provided. The flavivirus envelope protein, such as from yellow fever virus 17D vaccine strain, is modified replacing amino acids surrounding the fusion loop of the flavivirus backbone with corresponding amino acids from the dengue virus envelope protein. The chimeric protein is useful as a vaccine to stimulate an immune response against DENV infection, thereby producing broadly neutralizing (protective) antibodies against dengue virus and reduce the induction of non-neutralizing antibodies that will cause enhancement.

20 Claims, 22 Drawing Sheets

Specification includes a Sequence Listing.
Dengue/yellow fever E protein alignment

```
        1                                                              >DI/II
DENV4E MRCVGVGNRDFVEGVSGGAWVDLVLEHGGCVTTMAQGKPTLDFELTKTTAKEVALLRTYCIEASISNITT
DENV3E MRCVGVGNRDFVEGLSGATWVDVVLEHGGCVTTMAKNKPTLDIELQKTEATQLATLRKLCIEGKITNITT
DENV2E MRCIGISNRDFVEGVSGGSWVDIVLEHGSCVTTMAKNKPTLDFELIKTEAKQPATLRKYCIEAKLTNTTT
DENV1E MRCVGIGSRDFVEGLSGATWVDVVLEHGSCVTTMAKDKPTLDIELLKTEVTNPAVLRKLCIEAKISNTTT
17DE   AHCIGITDRDFIEGVHGGTWVSATLEQDKCVTVMAPDKPSLDISLETVAIDRPAEVRKVCYNAVLTHVKI

71                                                             >DII/I
DENV4E ATRCPTQGEPYLKEEQDQQYICRRDVVDR W      LF KGGVVTCAKFSCSGKITGNLVQIENLEYTVV
DENV3E DSRCPTQGEAXLPEEQDQNYVCKHTYVDR W      LF KGSLVTCAKFQCLEPIEGKVVQYENLKYTVI
DENV2E ESRCPTQGEPSLNEEQDKRFVCKHSMVDR W      LF KGGIVTCAMFTCKKNMEGKXVQPENLEYTIV
DENV1E DSRCPTQGEATLVEEQDANFVCRRTFVDR W      LF KGSLITCAKFKCVTKLEGKIVQYENLKYSVI
17DE   NDKCPSTGEAHLAEENEGDNACKRTYSDR W      LF KGSIVACAKFTCAKSMSLFEVDQTKIQYVIR

141                                                             >DI/II
DENV4E VTVHNGDTHAVGNDTSNHGVTATITPRSPSVEVKLPDYGELTLDCEPRSGIDFNEMILMKMKKKTWLVHK
DENV3E ITVHTGDQHQVGNET--QGVTAEITPQASTTEAILPEYGTLGLECSPRTGLDFNEMILLTMKNKAWMVHR
DENV2E ITPHSGEEHAVGNDTGKHGKEIKITPQSSITEAELTGYGTVTMECSPRTGLDFNEMVLLQMEXKAWLVHR
DENV1E VTVHTGDQHQVGNESTEHGTTATITPQAPTXEIQLTDYGALTLDCSPRTGLDFNEMVLLTMKEKSWLVHK
17DE   AQLHVGAKQENWNTDIK---TLKFDALSGSQEVEFIGYGKATLECQVQTAVDFGNSYIAEMETESWIVDR

211
DENV4E QWFLDLPLPWTAGADTSEVHWNYKERMVTFKVPHAKRQDVTVLGSQEGAMHSALAGATEVDSGDGNH-
DENV3E QWFFDLPLPWTSGATTETPTWNRKELLVTFKNAHAKKQEVVVLGSQEGAMHTALTGATEIQNSGGTS-
DENV2E QWFLDLPLPWLPGADTQGSNWIQKETLVTFKNPHAKKQDVVVLGSQEGAMHTALTGATEIQMSSGNL-
DENV1E QWFLDLPLPWTSGASTSQETWNRQDLLVTFKTAHAKKQEVVVLGSQEGAMHTALTGATEIQTSGTTT-
17DE   QWAQDLTLPWQSG---SGGVWREMHHLVEFEPPHAATIRVLALGNQEGSLKTALTGAMRVTKDTNDNNLY

281 >DII/I          >DI/DIII
DENV4E -MFAGHLKCKVRMEKLRIKGMSYTMCSGKFSIDKEMAETQHGTTVVKVKYEGAGAPCKVPIEIRDVNKEK
DENV3E -IFAGHLKCRLKMDKLELKGMSYAMCTNTFVLKKEVSETQHGTILIKVEYKGEDXPCKIPFSTEDGQGKA
DENV2E -LFTGHLKCRLRMDKLQLKGMSYSMCTGKFKXVKEIAETQHGTIVIRVQYEGDGSPCKIPFEIMDLEKRH
DENV1E -IFAGHLKCRLKMDKLTLKGMSYVMCTGSFKLEKEVAETQHGTVLVQIKYEGTDAPCKIPFSTQDEKGVT
17DE   KLHGGHVSCRVKLSALTLKGTSYKICTDKMFFVKNPTDTGHGTVVMQVKV-SKGAPCRIPVIVADDLTAA
```

FIG. 2

```
                351
DENV4E  VV-GRVISSTPLAENTNSVTNIELEPPFGDSYIVIGVGNSALTLHWFRKGSSIGKMFESTYRGAKRMAIL
DENV3E  HN-GRLITANPVVTKKEEPVNIEAEPPFGESNIVIGIGDNALKINWYKKGSSIGKMFEATARGARRMAIL
DENV2E  VL-GRLITVNPIVTEKDSPVNIEAEPPFGDSYIIIGVEPGQLKLNWFKKGSSIGQMFETTMRGAKRMAIL
DENV1E  QN-GRLITANPIVTDKEKPVNIEAEPPFGESYIVIGAGEKALKLSWFKKGSSIGKMFEATARGARRMAIL
17DE    INKGILVTVNPIASTNDDEVLIEVNPPFGDSYIIVGRGDSRLTYQWHKEGSSIGKLFTQTMKGVERLAVM
            421
DENV4E  GETAWDFGSVGGLFTSLGKAVHQVFGSVYTTMFGGVSWMIRILIGFLVLWIGTNSRNTSMAMTCIAVGGI
DENV3E  GDTAWDFGSVGGVLNSLGKMVHQIFGSAYTALFSGVSWVMKIGIGVLLTWIGLNSKNTSMSFSCIAIGII
DENV2E  GDTAWDFGSLGGVFTSIGKALHQVFGAIYGAAFSGVSWTMKILIGVIITWIGMNSRSTSLSVSLVLGVV
DENV1E  GDTAWDFGSIGGVFTSVGKLVHQIFGTAYGVLFSGVSWTMKIGIGVLLTWLGLNSRSTSLSMTCIAVGLV
17DE    GDTAWDFSSAGGFFTSVGKGIHTVFGSAFQGLFGGLNWITKVIMGAVLIWVGINTRNMTMSMSMILVGVI

491
DENV4E  TLFLGFTVQA
DENV3E  TLYLGAVVQA
DENV2E  TLYLGVMVQA
DENV1E  TLYLGVMVQA
17DE    MMFLSLGVGA
```

 = Fusion Loop
Bold and Underlined = Within 5A of Fusion Loop
Teal = Within 14A of Fusion Loop (shown only for DENV2)
Blue = Loss of binding position for 4.8A, D11Ck1, and 1.6D

```
4.8A        W101, L107

VACCINES AND METHODS FOR CREATING A VACCINE FOR INDUCING IMMUNITY TO ALL DENGUE VIRUS SEROTYPES

STATEMENT OF GOVERNMENT SUPPORT

This invention was made with government support under Grant No. R01AI099210 awarded by the National Institute of Allergy and Infectious Diseases. The government has certain rights to the invention.

CROSS-REFERENCE TO RELATED APPLICATIONS

This application is a continuation-in-part of U.S. Nonprovisional patent application Ser. No. 15/413,347, filed Jan. 23, 2017, entitled "Vaccines And Methods For Creating A Vaccine For Inducing Immunity To All Dengue Virus Serotypes", which claims priority to U.S. Nonprovisional patent application Ser. No. 13/660,653, filed Oct. 25, 2012, entitled "Vaccines And Methods For Creating A Vaccine For Inducing Immunity To All Dengue Virus Serotypes", and which claims priority to and the benefit of U.S. Provisional Patent Application No. 61/550,982, filed on Oct. 25, 2011, entitled "Vaccines And Methods For Creating A Vaccine For Inducing Immunity To All Dengue Virus Serotypes", and is incorporated herein by reference in its entirely.

FIELD OF INVENTION

This invention relates to viral vaccines. More specifically, the present invention provides vaccines for inducing of neutralizing antibody responses to various Dengue viral serotypes.

BACKGROUND OF THE INVENTION

Dengue virus (DENV) is a mosquito-transmitted virus from the genus *Flavivirus*. It is the most common cause of mosquito-borne viral diseases in tropical and subtropical regions around the world, and is expanding in geographic range and also in disease severity. The virus is a small, enveloped, icosahedral virus, with positive strand RNA of 11,000 nucleotides (Thaisomboonsuk, et al., Characterization of dengue-2 virus binding to surfaces of mammalian and insect cells. Am J Trop Med Hyg. 2005 April; 72(4): 375-83). There are four distinct serotypes of dengue that cause similar disease symptoms, serotypes 1-4 (DENV-1, DENV-2, DENV-3, and DENV-4) that cocirculate in many areas of the world and give rise to sequential epidemic outbreaks when the number of susceptible individuals in the local population reaches a critical threshold and weather conditions favor reproduction of the mosquito vectors *Aedes aegypti* and *Aedes albopictus*.

2.5 billion people living in regions where dengue is endemic are at risk of infection (Mackenzie, et al., Emerging flaviviruses: the spread and resurgence of Japanese encephalitis, West Nile and dengue viruses. Nat. Med. 2004 December; 10((12 Suppl):S98-S109; WHO 2012. Dengue and severe dengue. Fact sheet no. 117 last updated Sep. 13, 2018). Exposure to Dengue virus typically results in symptoms 3 days to 2 weeks after exposure. Approximately 50 to 100 million people per year are infected with DENV. DENV infections may be asymptomatic, but most often manifest as dengue fever (DF), a self-limited disease. An estimated 500,000 people, many of them children, are hospitalized annually with severe dengue symptoms, including dengue hemorrhagic fever/dengue shock syndrome (DHF/DSS) (WHO 2012. Dengue and severe dengue. Fact sheet no. 117 last updated Sep. 13, 2018; Gubler, Epidemic dengue/ dengue hemorrhagic fever as a public health, social and economic problem in the 21st century. Trends Microbiol. 2002 February; 10(2):100-103). Dengue infection symptoms include severe headache, occular pain; muscle, joint, and hone pain; macular or maculopapular rash; and varying levels of hemorrhagic response.

Infection with one serotype confers lifelong homotypic immunity, that is protective against that same serotype. The infection causes a cross-reactive antibody response against the other serotypes (and other flaviviruses as well). However, the immunity only provides short term (approximately three to six months) cross protection against heterotypic serotypes (Sabin, Research on dengue during World War II. Am. J. Trop. Med. Hyg. 1952 January; 1(1):30-50). Secondary, or more, DENV infections tend to produce broadly neutralizing response. Low levels of neutralizing antibodies, cross-reactive but nonneutralizing antibodies, or both from previous infections bind virions of other serotypes and target them to Fc receptors on macrophages and certain other cell types, enhancing infection of these cells (Halstead, et al., Dengue viruses and mononuclear phagocytes. I. Infection enhancement by non-neutralizing antibody. J. Exp. Med. 1977 Jul. 1; 146(1):201-17). DENV imposes one of the largest social and economic burdens of any mosquito-borne viral pathogen. There is no specific treatment for infection, and control of dengue virus by vaccination has proved elusive. However, the risk of severe disease is greatest during secondary, heterotypic infections in subjects with more than one circulating serotype. An increasing problem for public health officials has been the occurrence of severe complications arising from dengue viral infection. Both dengue hemorrhagic fever (DHF) and shock syndromes (DSS) are clinical outcomes related to the presence of pre-existing immunity to a heterologous dengue virus serotype. The presence of these cross-reactive and nonneutralizing antibodies also correlated with severe disease outcome (DHF/DSS) in several studies (Halstead, Pathogenesis of dengue: challenges to molecular biology. Science. 1988 Jan. 29; 239(4839):476-81; Kliks, et al., Evidence that maternal dengue antibodies are important in the development of dengue hemorrhagic fever in infants. Am. J. Trop. Med. Hyg. 1988 March; 38(2):411-9; Vaughn, et al., Dengue viremia titer, antibody response pattern, and virus serotype correlate with disease severity. J. Infect. Dis. 2000 January; 181(1):2-9). Higher levels of viremia are associated with the development of DHF (Vaughn, et al., Dengue viremia titer, antibody response pattern, and virus serotype correlate with disease severity. J. Infect. Dis. 2000 January; 181(1):2-9; Vaughn, et al., Dengue in the early febrile phase: viremia and antibody responses. J. Infect. Dis. 1997 August; 176(2): 322-30). A preponderance of antibodies that recognize neutralizing epitopes will lead to virus clearance and reduced symptoms, while an abundance of antibodies that recognize enhancing epitopes will lead to more severe disease. Antibody-dependent enhancement (ADE) is an increase in viral infection as a result of antibody-mediated cellular entry, is common among flaviviruses, and has been shown to decrease as viral particles remain extracellularly with antibodies, i.e. virus particles exposed to antibodies experience time-dependent loss of infectivity even when exposed to partially neutralizing antibodies, which is not attributed to increased antibody binding (Dowd, et al., A dynamic landscape for antibody binding modulates antibody-mediated neutralization of West Nile virus. PLoS Pathog. 2011 June;

7(6):e1002111). This antibody-dependent enhancement effect may also explain the sequential nature of epidemic outbreaks, as well as the severe disease seen in infants as maternal antibodies wane (Halstead, Pathogenesis of dengue: challenges to molecular biology. Science. 1988 Jan. 29; 239(4839):476-81; Kliks, et al., Evidence that maternal dengue antibodies are important in the development of dengue hemorrhagic fever in infants. Am. J. Trop. Med. Hyg. 1988 March; 38(2):411-9; Simmons, et al., Maternal antibody and viral factors in the pathogenesis of dengue virus in infants. J. Infect. Dis. 2007 Aug. 1; 196(3):416-24).

Dengue Haemorrhagic Fever is initially characterized by a minor febrile illness lasting 3-5 days. The patient may deteriorate at defervescence into the next phase of the syndrome with hemostatic disorders, and increased vascular permeability frequently accompanied by internal bleeding and shock. As many as 1.5 million children are reported to have been hospitalized with 33,000 deaths from this syndrome since it was first recognized in the Philippines and Thailand in the 1950s. DHF/DSS has since continued to persist, and outbreaks can pose major problems to public health in many countries. Unfortunately, the pathogenesis of DHF/DSS is not completely understood. Epidemiological studies have shown that the presence of cross-reactive antibodies correlates with a more severe disease outcome during subsequent infections with a different serotype. The mechanism for this effect appears to be an antibody-dependent enhancement of infection of macrophage and macrophage-like cells that express Fc receptors. These cells are normally not infected efficiently by dengue, but become highly infectable in the presence of dengue virus binding antibodies that then target the virus particles directly to the macrophages through the interaction of the antibody heavy chains and the cellular Fc receptors.

Like other members of the genus Flavivirus, DENV has a lipid envelope and a positive-strand RNA genome that codes for a single large polyprotein that encodes 3 structural proteins- the capsid (C) protein, the membrane (M) protein, and the envelop (E) protein- and 7 nonstructural proteins, including proteases and RNA polymerase. This polyprotein is cleaved into separate segments to form the capsid (C), premembrane (prM/M), and envelope (E) structural proteins and enzymatic components required for viral replication and transmission (Dengue and dengue hemorrhagic fever: history and current status. Gubler, Goode. Eds. (Novartis Foundation (2006)).

The E glycoprotein assembles as a dimer on the viral surface, and possesses domains, DI, DII, and DIII, as well as a transmembrane domain (Modis, et al., A ligand-binding pocket in the dengue virus envelope glycoprotein. Proc. Natl. Acad. Sci. U.S.A 2003 Jun. 10; 100(12):6986-91; Rey, et al., The envelope glycoprotein from tick-borne encephalitis virus at 2 A resolution. Nature. 1995 May 25; 375 (6529):291-8). At one end of the molecule is the fusion loop within DII, and at the other end is DIII, which is involved in host cell binding (Crill, et al., Monoclonal antibodies that bind to domain III of dengue virus E glycoprotein are the most efficient blockers of virus adsorption to Vero cells. J. Virol. 2001 August; 75(16):7769-73). E protein is believed to facilitate cell binding to surface receipts, like heparin sulfate, resulting in endocytosis or fusion with the plasma membrane itself. Studies suggest the virus is uptaken by antibody-dependent Fc receptor endocytosis or trypsin-sensitive receptor-based endocytosis, whereby the virus is released into the cell via a fusion loop, found in domain DII of the E protein (Thaisomboonsuk, et al., Characterization of dengue-2 virus binding to surfaces of mammalian and insect cells. Am J Trop Med Hyg. 2005 April; 72(4):375-83). During the infection process, the fusion loop is projected outward by a structural rearrangement of the E protein, resulting in the fusion loop "harpooning" into the target cell membrane. This interaction is critical for the subsequent membrane fusion step, mediated by a further E protein movement that pulls the cell and virus membranes together. Low pH causes a conformation change in the E protein, exposing domains in or around the fusion loop, which interact with host receptors, including CD209, Rab 5, GRP 78, and the mannose receptor, to mediate entry into a cell. During viral packaging, the external E glycoprotein is physically arranged in a herringbone pattern as a series of 90 homodimers on the outer surface of the mature virus particle (Kuhn, et al., Structure of dengue virus: implications for flavivirus organization, maturation, and fusion. Cell. 2002 Mar. 8; 108(5):717-25). On immature particles, the prM protein lies over the E protein and serves to protect the virus particle from undergoing premature fusion or inactivation within the secretory pathway of the host cell. prM is subsequently cleaved by a host protease to release the ectodomain and allow viral maturation (Yu, et al., Structure of the immature dengue virus at low pH primes proteolytic maturation. Science. 2008 Mar. 28; 319(5871):1834-7). Upon infection and entry of DENV into the acidic environment of the endosome, the E proteins undergo a conformational change and reassemble into 60 trimers with their fusion loops forming the tip of a trimeric spike oriented to insert into the endosomal membrane within the target cell. Subsequent reconfiguration of the E protein trimers results in fusion of the viral membrane and target cell endosomal membrane to facilitate release of the viral contents into the cytoplasm (Harrison, Viral membrane fusion. Nat. Struct. Mol. Biol. 2008 July; 15(7):690-8; Heinz, et al., Flavivirus structure and membrane fusion. Adv. Virus Res. 2003; 59:63-97; Zhang, et al., Visualization of membrane protein domains by cryo-electron microscopy of dengue virus. Nat. Struct. Biol. 2003 November; 10(11):907-12).

Monoclonal antibodies (MAbs) have been used to further elucidate important epitopes. However, to date, most anti-DENV monoclonal antibodies are of murine origin (mMAbs), generated from mice (Crill, et al., Monoclonal antibodies that bind to domain III of dengue virus E glycoprotein are the most efficient blockers of virus adsorption to Vero cells. J. Virol. 2001 August; 75(16):7769-73; Halstead, Neutralization and antibody-dependent enhancement of dengue viruses. Adv. Virus Res. 2003; 60:421-67; Sukupolvi-Petty, et al., Structure and function analysis of therapeutic monoclonal antibodies against dengue virus type 2. J. Virol. 2010 September; 84(18):9227-39). mMAbs may not accurately represent the human antibody response to DENV, as mice do not experience human disease other than a transitory viremia and produce an antibody response with more limited diversity and typically lower-affinity antibodies than humans. Recent studies with human monoclonal anti-DENV antibodies (hMAbs) have highlighted both similarities and major differences between the behavior of sera from convalescent DENV patients and purified hMAbs.

Further, studies have attempted to determine the human antibody response against dengue virus by characterizing human anti-dengue monoclonal antibodies. The nature of the human antibody response to DENV is likely to play a dominant role in defining the outcome of infection. Studies with sera from convalescent DENV patients have yielded conflicting information regarding the human antibody response and the epitopes that these antibodies target.

In the work of Schieffelin et al., three antibodies that targeted the E protein were isolated from a single donor (Schieffelin, et al., Neutralizing and non-neutralizing monoclonal antibodies against dengue virus E protein derived from a naturally infected patient. Virol. J. 2010 Feb. 4; 7:28). All three antibodies were cross-reactive with at least two DENV serotypes, one was neutralizing, and all were able to enhance DENV infection. Dejnirattisai et al. reported that in a panel of hMAbs from seven donors, the majority of the antibody response was against prM and was very poorly neutralizing but highly enhancing (Dejnirattisai, et al., Cross-reacting antibodies enhance dengue virus infection in humans. Science. 2010 May 7; 328(5979):745-8). Beltramello et al. described a wide variety of hMAbs from five DENV patients (Beltramello, et al., The human immune response to Dengue virus is dominated by highly cross-reactive antibodies endowed with neutralizing and enhancing activity. Cell Host Microbe. 2010 Sep. 16; 8(3):271-83). They included hMAbs against prM, as well as E. However, in contrast to the findings of Dejnirattisai, et al., half of the prM hMAbs reported by Beltramello et al. showed substantial neutralization activity (Beltramello, et al., The human immune response to Dengue virus is dominated by highly cross-reactive antibodies endowed with neutralizing and enhancing activity. Cell Host Microbe. 2010 Sep. 16; 8(3): 271-83). Among the hMAbs recognizing E, Beltramello et al. described antibodies targeting DI/II and DIII. The DIII hMAbs were very highly neutralizing and included serotype-specific and cross-reactive examples. The neutralization activities of the DI/II hMAbs were more diverse and included nonneutralizing, serotype-specific neutralizing, and cross-neutralizing examples. Two of the cross-neutralizing DI/II hMAbs were mapped to the fusion loop using West Nile virus (WNV) E protein mutants. However, antibodies to this flavivirus epitope are typically conformation-sensitive (Lai, et al., Antibodies to envelope glycoprotein of dengue virus during the natural course of infection are predominantly cross-reactive and recognize epitopes containing highly conserved residues at the fusion loop of domain II. J. Virol. 2008 July; 82(13):6631-43)

de Alwis et al. reported that after primary infection most hMAbs were cross-reactive and weakly neutralizing and that many bound to prM (de Alwis, et al., In-depth analysis of the antibody response of individuals exposed to primary dengue virus infection. PLoS Negl. Trop. Dis. 2011 June; 5(6): e1188). Using a modified screening procedure, they were able to detect rare DIII hMAbs that were serotype specific and strongly neutralizing. Recently, de Alwis et al. reported that the majority of antibodies in human sera bound to intact virions, not monomeric E (de Alwis, et al., Identification of human neutralizing antibodies that bind to complex epitopes on dengue virions. Proc. Natl. Acad. Sci. U.S.A. 2012 May 8; 109(19):7439-44). They found that though abundant in human sera, cross-reactive antibodies did not contribute to neutralization and that type-specific antibodies were responsible for potent neutralization. These findings were confirmed with 3 hMAbs that were isolated by first screening for antibodies that bound to intact virions and then screening for a subset of antibodies that were potently neutralizing. They generated escape mutants and mapped the mutations to the quaternary epitopes containing contacts on two different E proteins in the hinge region between DI and DII.

Interestingly, while one of the predominant epitopes recognized by human serum antibodies appears to include the fusion loop and adjacent regions (Lai, et al., Antibodies to envelope glycoprotein of dengue virus during the natural course of infection are predominantly cross-reactive and recognize epitopes containing highly conserved residues at the fusion loop of domain II. J. Virol. 2008 July; 82(13): 6631-43; Lin, et al., Analysis of epitopes on dengue virus envelope protein recognized by monoclonal antibodies and polyclonal human sera by a high throughput assay. PLoS Negl. Trop. Dis. 2012 January; 6(1):e1447), one study reported that these fusion loop antibodies are nonneutralizing (Lai, et al., Antibodies to envelope glycoprotein of dengue virus during the natural course of infection are predominantly cross-reactive and recognize epitopes containing highly conserved residues at the fusion loop of domain II. J. Virol. 2008 July; 82(13):6631-43). He et al. tested the ability of patient sera to block binding of DENV serotype 2 (DENV-2) to Vero cells and reported that neutralization occurred primarily by blocking cell attachment, suggestive of a major role for antibodies targeting DIII (He, et al., Antibodies that block virus attachment to Vero cells are a major component of the human neutralizing antibody response against dengue virus type 2. J. Med. Virol. 1995 April; 45(4):451-61). In contrast, Wahala et al. subsequently reported that human antibodies directed toward epitopes other than DIII (presumably DI/III) are primarily responsible for neutralization (Wahala, et al., Dengue virus neutralization by human immune sera: role of envelope protein domain III-reactive antibody. Virology. 2009 Sep. 15; 392 (1):103-13).

Thus, multiple questions remain about the nature of the antibody balance, including which epitopes are most important for neutralization versus enhancement and whether these are distinct or overlapping epitopes. One of the conclusions to come out of the human studies is that the dominant human antibody response against the dengue virus surface proteins, membrane (prM and M) and envelope (E, soluble envelope protein, sE), is non-neutralizing and cross reactive against the four serotypes of dengue. These non-neutralizing, cross-reactive antibodies are the primary cause of the antibody dependent enhancement of disease. These studies with hMAbs emphasize the complexity of the human antibody response against DENV and highlight the importance of further examination of the roles of different epitopes in prM, in E protein DI/II (either the fusion loop or the hinge region), and in DIII and the mechanisms by which different antibodies neutralize DENV infection. For instance, an affected stage of viral entry—virus binding to the cell surface versus fusion between the viral envelope and endosomal membrane—has never been identified for any neutralizing hMAb.

Ongoing research is focused on potential vaccines to dengue viral infection. In 2015, Sanofi Pasteur was approved to release Dengvaxia, a dengue vaccine based on an attenuated yellow fever strain possessing the premembrane (PrM) and envelope (E) genes of four dengue virus serotypes, i.e. an attenuated tetravalent dengue vaccine. Prior work has shown yellow fever vaccine 17D (YF-17D) induces an efficient immune response against infection, which usually begins by around 10 days after vaccination in 95% of vaccine recipients and can last up to 35 years post-vaccination (Poland, et al., Persistence of neutralizing antibody 30-35 years after immunication with 17D yellow fever vaccine. Bull World Health Organ. 1981; 59(6):895-900; Monath, et al., Pathogenesis and pathophysiology of yellow fever. Adv Virus Res. 2003; 60:343-95; Niedrig, et al., Assessment of IgG antibodies against yellow fever virus after vaccination with 17D by different assays: neutralization test, haemagglutination inhibition test, immunofluorescence assay and ELISA. Trop Med Int Health. 1999; 4(12): 867-71). Studies suggests YF-17D infect dendritic cells and activate multiple Toll-like receptors, resulting in a strong immunogenic response (Muyanja, et al., Immune activation alters cellular and humoral responses to yellow fever 17D vaccine. J Clin Invest. 2014 Jul. 1; 124(7):3147-58; Querec, et al., Systems biology approach predicts immunogenicity of the yellow fever vaccine in humans. Nat Immunol. 2008; 10(1):116-25; Barba-Spaeth, Live attenuated yellow fever 17D infects human DCs and allows for presentation of endogenous and recombinant T cell epitopes. J Exp Med. 2005; 202(9):1179-84; Martins, et al., Activation/modulation of adaptive immunity emerges simultaneously after 17DD yellow fever first-time vaccination: is this the key to prevent severe adverse reactions following immunization? Clin Exp Immunol. 2007; 148(1):90-100; Mandl, et al., Distinctive TLF? Signaling, type I IFN production, and attenuated innate and adaptive immune responses to yellow fever virus in a primate reservoir host. J Immunol. 2011; 186(11):6406-16). Concerns regarding the possibility of vaccine components eliciting enhancing antibody responses, as opposed to protective responses, have been a major concern in designing and testing vaccines to protect against dengue infections. There is thus a need for a vaccine that may be effective against different serotypes and which does not enhance the course of the DENV infection. In fact, Dengvaxia was found to provide only partial protection, and was found to worsen disease symptoms in some individuals whom had no prior dengue viral exposure, resulting in some countries withdrawing the vaccine.

Numerous factors can affect vaccine responses, including genetic background, gender, age, and environmental conditions (Monath, et al., Comparative safety and immunogenicity of two yellow fever 17D vaccines (ARILVAX and YF-VAX) in a phase III multicenter, double-blind clinical trial. Am J Trop Me Hyg. 2002; 66(5):533-41; Monath, et al. Yellow fever 17D vaccine safety and immunogenicity in the elderly. Hum Vaccin. 2005; 1(5):207-214; Black, et al. BCG-induced increase in interferon-gamma response to mycobacterial antigens and efficacy of BCG vaccination in Malawi and the UK: two randomised controlled studies. Lancet. 2002; 359(9315):1393-1401). Studies of YFV vaccines suggest differential sensitization due to exposure to environmental mycobacteria can alter vaccine responsiveness (Lalor, et al. BCG vaccination induces different cytokine profiles following infant BCG vaccination in the UK and Malawi. J Infect Dis. 2011; 204(7):1075-1085). Of note, several vaccine candidates use the YF-17D backbone as a vector for presentation of antigens from DENV, Japanese encephalitis virus, West Nile virus, and HIV (Bonaldo, et al. Recombinant yellow fever vaccine virus 17D expressing simian immunodeficiency virus SIVmac239 gag induces SIV-specific CD8+ T-cell responses in rhesus macaques. J Virol. 2010; 84(7):3699-3706; Guy, et al. Preclinical and clinical development of YFV 17D-based chimeric vaccines against dengue, West Nile and Japanese encephalitis viruses. Vaccine. 2010; 28(3):632-649; Martins, et al. Immunogenicity of seven new recombinant yellow fever viruses 17D expressing fragments of SIVmac239 Gag, Nef, and Vif in Indian rhesus macaques. PLoS One. 2013; 8(1):e54434).

However, the present art has been unable to provide a neutralizing vaccine for dengue virus. Accordingly, the present invention satisfies this unmet need, providing a chimeric protein directed at the E protein fusion loop to neutralize Dengue virus infections, without regard to serotype.

SUMMARY OF THE INVENTION

In this work, broadly cross-reactive and neutralizing hMAbs were screened from three patients with distinct histories of DENV infection, and identified three similar hMAbs that mapped to the conserved epitope containing the E protein DII fusion loop. These hMAbs were broadly reactive, high affinity, and conformationally sensitive. With some exceptions, they showed broad but intermediate neutralization activity against all four DENV serotypes and also enhanced all four serotypes. Using a novel assay, these hMAbs were confirmed to inhibit intracellular virus fusion during entry, rather than cell binding, and mechanistic characterization of these hMAbs was determined (Costin, et al., Mechanistic study of broadly neutralizing human monoclonal antibodies against dengue virus that target the fusion loop. J Virol. 2013 January; 87(1):52-66).

Described here is a method of forming a chimeric protein, comprising the steps of providing a yellow fever virus 17-D envelope protein having SEQ ID No. 1; providing a dengue fever virus envelope protein selected from the group consisting of SEQ ID No. 2, SEQ ID No. 3, SEQ ID No. 4, or SEQ ID No. 5; and substituting one or more of amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of SEQ ID No. 1 with the corresponding amino acid of the selected dengue fever virus envelope protein to create a chimeric envelope protein.

Also described here is a method of creating a treatment composition, comprising the steps of providing a portion of an envelope protein from a flavivirus; providing a dengue fever virus envelope protein selecting from the group consisting of SEQ ID No. 2, SEQ ID No. 3, SEQ ID No. 4, or SEQ ID No. 5; substituting a portion of the envelope protein amino acids of the flavivirus with a the corresponding envelope protein amino acids of the selected dengue fever virus to create a chimeric envelope protein; providing a pharmaceutically acceptable excipient; and mixing the chimeric envelope protein and the excipient.

Further described here is a chimeric protein, comprising: an envelope protein comprised of yellow fever virus 17-D envelope protein having SEQ ID No. 1, wherein selected amino acids of the yellow fever virus 17-D envelope protein are substituted with corresponding amino acids of dengue fever virus envelope protein selected from the group consisting of SEQ ID No. 2, SEQ ID No. 3, SEQ ID No. 4, or SEQ ID No. 5.

Also described here is a composition for treatment of dengue fever virus, comprising: a chimeric envelope protein comprised of a flavivirus envelope protein, wherein selected amino acids of the flavivirus envelope protein are substituted with corresponding amino acids of dengue fever virus envelope protein selected from the group consisting of SEQ ID No. 2, SEQ ID No. 3, SEQ ID No. 4, or SEQ ID No. 5; and a pharmaceutically acceptable excipient.

BRIEF DESCRIPTION OF THE DRAWINGS

For a fuller understanding of the invention, reference should be made to the following detailed description, taken in conjunction with the accompanying drawings, in which:

FIG. 2 is an amino acid sequence alignment of DENV-1 to 4 E protein (DENV1E through DENV4E) and the yellow fever 17-D envelope protein.

DETAILED DESCRIPTION OF THE INVENTION

Figure 1:
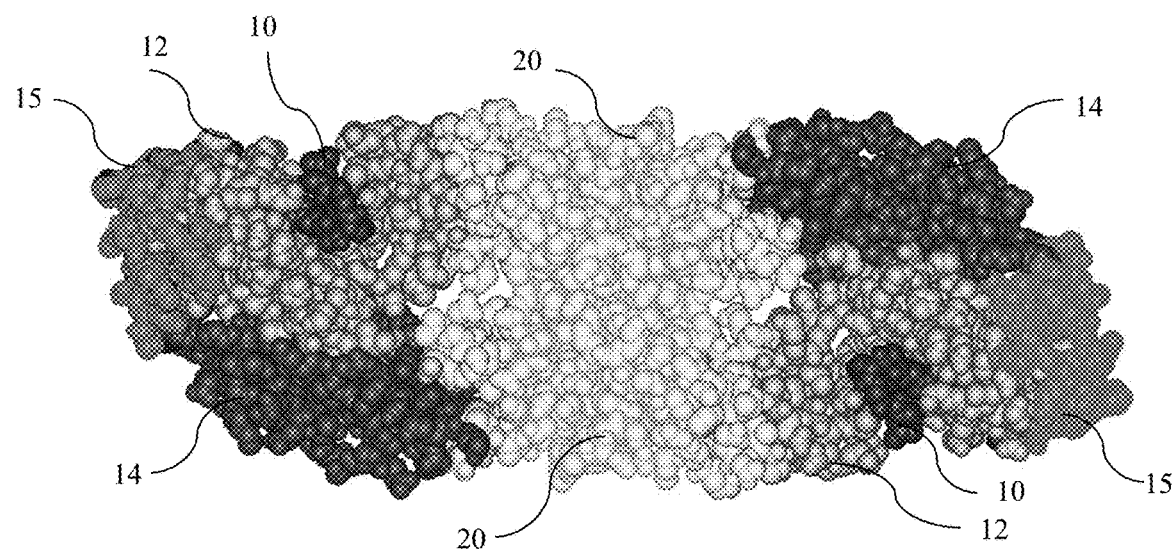
FIGS. 1(a) and (b) are molecular models showing the protein crystal structure of the DENV envelope protein and demonstrates the location of the fusion loop and 5 Å and 14 Å surrounding amino acids. The structure is shown from (a) a proximal view looking at the domains of the glycoprotein farthest from the viral capsid, and (b) a distal view looking at the glycoprotein domains adjacent to the viral capsid.

As used in this specification, the singular forms "a", "an", and "the" include plural reference unless the context clearly dictates otherwise. Thus, for example, a reference to "a microorganism" includes more than one such microorganism. A reference to "a cell" includes more than one such cell, and so forth. A reference to "a compound" includes more than one such compound.

As used herein, "about" means approximately or nearly and in the context of a numerical value or range set forth means±15% of the numerical.

As used herein "animal" means a multicellular, eukaryotic organism classified in the kingdom Animalia or Metazoa. The term includes, but is not limited to, mammals. Nonlimiting examples include rodents, mammals, aquatic mammals, domestic animals such as dogs and cats, farm animals such as sheep, pigs, cows and horses, and humans. Wherein the terms "animal" or the plural s are used, it is contemplated that it also applies to any animals.

As used herein the term "patient" is understood to include an animal, especially a mammal, and more especially a human that is receiving or intended to receive treatment. Additionally, as used herein "patient", means members of the animal kingdom, including mammals, such as but not limited to, primates including humans, gorillas and monkeys; rodents, such as mice, fish, reptiles and birds. The patient may be any animal requiring therapy, treatment, or prophylaxis. The term treatment, as used in this definition only, is intended to mean that regiment described is continued until the underlying disease is resolved, whereas therapy requires that the regiment alleviate one or more symptoms of the underlying disease. Prophylaxis means that regiment is undertaken to prevent a possible occurrence, such as where a pre-cancerous lesion is identified.

As used herein the term "suspectable" refers to a patient or individual who is at risk of contracting a Dengue viral infection. Examples of patients or individuals at particular risk of contracting a Dengue viral infection are those whom live in regions known to have endemic Dengue infection, regions where Dengue hosts are located, or patients or individuals whom are traveling to a region having endemic Dengue infection or a region possessing Dengue hosts.

As used herein the term "correlating" refers to an amino acid identified as having the same or similar location in a polyprotein as determined by a comparison of the polyproteins to identify sequence homology. For example, the presence and type of correlating amino acid can be determined for the flavivirus yellow fever virus (YFV) and dengue virus serotypes 1-4 using Table 1. Similar analysis can identify the correlating amino acids of envelope proteins for other flavivirus' such as West Nile Virus, St. Louis encephalitis, Japanese encephalitis, and Kunjin virus, in a similar fashion.

As used herein the term "concurrently" means sufficiently close in time to produce a combined effect. For example, concurrently may be simultaneously, or it may be two or more events occurring within a short time period before or after each other.

As used herein the term "administration" and variants thereof (e.g., "administering" a vaccine) in reference to a vaccine, or provaccine, of the invention means introducing the protein, glycoprotein, or a vaccine or prodrug variant of the vaccine into the system of the animal in need of vaccination. When the vaccine or prodrug variant thereof is provided in combination with one or more other active agents, "administration" and its variants are each understood to include concurrent and sequential introduction of the vaccine or prodrug thereof and other agents.

As used herein the term "therapeutically effective amount" as used herein means that amount of active compound or pharmaceutical agent that elicits the biological or medicinal response in a tissue, system, animal or human that is being sought by a researcher, veterinarian, medical doctor or other clinician, whether provided in a single dosing regimen or multiple dosing regimen. In reference to a vaccination of viral infection, an effective amount comprises an amount sufficient to induce an immune response that kills or inhibits the replication of the virus. In some embodiments, an effective amount is an amount sufficient to prevent viral capsid fusion, thereby preventing cellular infection. In some embodiments, an effective amount is an amount sufficient to prevent or delay occurrence and/or recurrence or a viral infection. An effective amount can be administered in one or more doses. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of immunoresponsiveness of the individual or patient; the bioavailability characteristics of the preparation administered; the dose regimen selected; the use of concomitant medication; and other relevant circumstances.

As used herein a "pharmaceutically acceptable" component is one that is suitable for use with humans and/or animals without undue adverse side effects (such as toxicity, irritation, and allergic response) commensurate with a reasonable benefit/risk ratio.

As used herein the term "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

As used herein the term "pharmaceutically acceptable carrier" is a carrier, such as a solvent, suspending agent or vehicle, for delivering the compound or compounds in question to the animal or human. The carrier may be liquid or solid and is selected with the planned manner of administration in mind. Liposomes, niosomes, and vesciles also act as a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The compounds of the present invention can be formulated as pharmaceutical compositions and administered to a patient, such as a human patient, in a variety of forms adapted to the chosen route of administration, e.g., orally or parenterally, by intravenous, intramuscular, topical, or subcutaneous routes.

The active components may be systemically administered, such as intravenously or intraperitoneally by infusion or injection. Solutions of the active compound or its salts can be prepared in water or other suitable solvent, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with several of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient presenting the previously sterile-filtered solutions.

Useful dosages of the vaccine or prodrug of the present invention can be determined by comparing their in vitro activity, and in vivo activity in animal models. Methods for the extrapolation of effective dosages in mice, and other animals, to humans are known to the art (U.S. Pat. No. 4,938,949 (Borch, et al.)).

As used herein, "viral infection" or "dengue infection" means a condition brought about by small particles containing RNA through internalization and replication in a host cell via sequestration of the host cellular machinery.

As used herein, "vaccination" means administering an antigen to a patient, to induce an immune response designed to limit viral infection.

As used herein, "dengue haemorrhagic fever", or "DHF", means a severe biological response to dengue viral infection, characterized by elevated fever, fatigue, mailaise, which progresses to include at least one of the following severe abdominal pain, persistent vomiting, cycling in temperature (from fever to hypothermia), hemorrhagic manifestations, altered mental status (irritability, confusion), bleeding under the skin, nosebleeds, acute hypotension (shock), weak pulse, pain in the muscles, bones, or joints, rashes on the skin, acute fever, sudden fever, and cold or clammy skin, restlessness. Complications from DHF include seizures, brain damage, thrombosis, heptoinjury, bronchioinjury, cardiac damage, shock, and death.

As used herein, "dengue shock syndrome", or "DSS", means endothelial dysfunction induced by cytokines and chemical mediators in response to dengue viral infection mediated by occurs. DSS can occur in concert with DHF, or separately, and can result from myocardial dysfunction and dehydration, which contribute to shock, and ultimately multiorgan failure.

The invention relates to a chimeric protein vaccine, and methods for vaccinating patients in need of preventative treatment for denuge viral infection using a chimeric protein. In some embodiments, the chimeric protein is used to produce a live attenuated vaccine, or a subunit vaccine that is not replicative. The chimeric protein is directed toward a flavivirus E protein comprising at least one dengue viral amino acid substitution adjacent to the E protein fusion loop. The flavirirus E protein antigen is optionally integrated into E protein vaccine construct derived from yellow fever virus (YFV), West Nile Virus, St. Louis encephalitis, Japanese encephalitis, and Kunjin virus.

Example 1

This chimeric E protein is a useful target to modify the yellow fever 17-D vaccine, one of the most successful vaccines ever developed, for use in dengue viral vaccination. The fusion loop was identified as a target from mechanistic experiments. These antibodies do not interfere with virus-cell binding, but do inhibit the ability of virus to fuse with liposomes. There is further defined their epitopes through binding experiments with a large panel of E protein mutants. Mutations in the E protein that prevent binding of these antibodies map to locations in and near to the fusion loop.

Figure 1B:
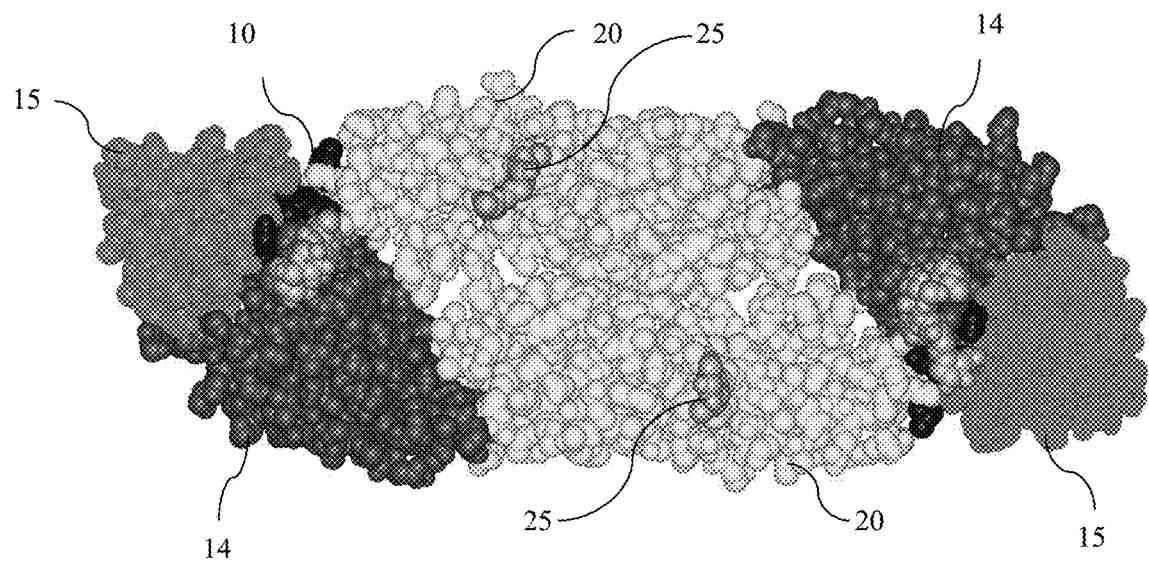

The chimeric protein is created by substituting amino acids of yellow fever virus (YFV), in particular YFV17D, envelope protein proximal to the domain II fusion loop. As used in this invention, amino acids "proximal to" the domain II fusion loop are those amino acids which are near the domain II fusion loop of the YFV envelope protein, shown in FIG. 1(a). In one embodiment, amino acids which are within 5 Å of the fusion loop are proximal to the fusion loop. In another embodiment, those amino acids which are within 14 Å of the fusion loop are proximal to the fusion loop are proximal to the fusion loop. Amino acids within 5 Å and 14 Å of the fusion loop are also shown in FIG. 1(b).

The fusion loop is a structural feature of flavivirus envelope proteins that is found on the tip of domain II and is responsible for direct interaction of the envelope (E) protein with the target cell lipid membrane. As shown in FIG. 2, the fusion loop is highly conserved in dengue and yellow fever viruses. The cysteine (C) at position 105 in the fusion loop forms a disulfide bond with the conserved cysteine (C) at position 74. This disulfide is important for the correct folding of the fusion loop. Amino acids within 5 Å and 14 Å of the fusion loop are important in YFV and DENV infection as well.

YFV 17D strain envelope protein has the following sequence, identified as SEQ ID No. 1:

AHCIGITDRDFIEGVHGGTWVSATLEQDKCVTVMAPDKPSLDISLETVAID
RPAEVRKVCYNAVLTHVKINDKCPSTGEAHLAEENEGDNACKRTYSDRGWG
NGCGLFGKGSIVACAKFTCAKSMSLFEVDQTKIQYVIRAQLHVGAKQENWN
TDIKTLKFDALSGSQEVEFIGYGKATLECQVQTAVDFGNSYIAEMETESWI
VDRQWAQDLTLPWQSGSGGVWREMHHLVEFEPPHAATIRVLALGNQEGSLK
TALTGAMRVTKDTNDNNLYKLHGGHVSCRVKLSALTLKGTSYKICTDKMFF
VKNPTDTGHGTVVMQVKVSKGAPCRIPVIVADDLTAAINKGILVTVNPIAS
TNDDEVLIEVNPPFGDSYIIVGRGDSRLTYQWHKEGSSIGKLFTQTMKGVE
RLAVMGDTAWDFSSAGGFFTSVGKGIHTVFGSAFQGLFGGLNWITKVIMGA
VLIWVGINTRNMTMSMSMILVGVIMMFLSLGVGA

DENV strain 1 envelope protein has the following sequence, identified as SEQ ID No. 2:

MRCVGIGSRDFVEGLSGATWVDVVLEHGSCVTTMAKDKPTLDIELLKTEVT
NPAVLRKLCIEAKISNTTTDSRCPTQGEATLVEEQDANFVCRRTFVDRGWG
NGCGLFGKGSLITCAKFKCVTKLEGKIVQYENLKYSVIVTVHTGDQHQVGN
ESTEHGTTATITPQAPTXEIQLTDYGALTLDCSPRTGLDFNEMVLLTMKEK
SWLVHKQWFLDLPLPWTSGASTSQETWNRQDLLVTFKTAHAKKQEVVVLGS
QEGAMHTALTGATEIQTSGTTTIFAGHLKCRLKMDKLTLKGMSYVMCTGSF
KLEKEVAETQHGTVLVQIKYEGTDAPCKIPFSTQDEKGVTQNGRLITANPI
VTDKEKPVNIEAEPPFGESYIVIGAGEKALKLSWFKKGSSIGKMFEATARG
ARRMAILGDTAWDFGSIGGVFTSVGKLVHQIFGTAYGVLFSGVSWTMKIGI
GVLLTWLGLNSRSTSLSMTCIAVGLVTLYLGVMVQA

DENV strain 2 envelope protein has the following sequence, identified as SEQ ID No. 3:

MRCIGISNRDFVEGVSGGSWVDIVLEHGSCVTTMAKNKPTLDFELIKTEAK
QPATLRKYCIEAKLTNTTTESRCPTQGEPSLNEEQDKRFVCKHSMVDRGWG
NGCGLFGKGGIVTCAMFTCKKNMEGKXVQPENLEYTIVITPHSGEEHAVGN
DTGKHGKEIKITPQSSITEAELTGYGTVTMECSPRTGLDFNEMVLLQMEXK
AWLVHRQWFLDLPLPWLPGADTQGSNWIQKETLVTFKNPHAKKQDVVVLGS
QEGAMHTALTGATEIQMSSGNLLFTGHLKCRLRMDKLQLKGMSYSMCTGKF
KXVKEIAETQHGTIVIRVQYEGDGSPCKIPFEIMDLEKRHVLGRLITVNPI
VTEKDSPVNIEAEPPFGDSYIIIGVEPGQLKLNWFKKGSSIGQMFETTMRG
AKRMAILGDTAWDFGSLGGVFTSIGKALHQVFGAIYGAAFSGVSWTMKILI
GVIITWIGMNSRSTSLSVSLVLVGVVTLYLGVMVQA

DENV strain 3 envelope protein has the following sequence, identified as SEQ ID No. 4:

MRCVGVGNRDFVEGLSGATWVDVVLEHGGCVTTMAKNKPTLDIELQKTEAT
QLATLRKLCIEGKITNITTDSRCPTQGEAXLPEEQDQNYVCKHTYVDRGWG
NGCGLFGKGSLVTCAKFQCLEPIEGKVVQYENLKYTVIITVHTGDQHQVGN
ETQGVTAEITPQASTTEAILPEYGTLGLECSPRTGLDFNEMILLTMKNKAW
MVHRQWFFDLPLPWTSGATTETPTWNRKELLVTFKNAHAKKQEVVVLGSQE
GAMHTALTGATEIQNSGGTSIFAGHLKCRLKMDKLELKGMSYAMCTNTFVL
KKEVSETQHGTILIKVEYKGEDXPCKIPFSTEDGQGKAHNGRLITANPVVT
KKEEPVNIEAEPPFGESNIVIGIGDNALKINWYKKGSSIGKMFEATARGAR
RMAILGDTAWDFGSVGGVLNSLGKMVHQIFGSAYTALFSGVSWVMKIGIGV
LLTWIGLNSKNTSMSFSCIAIGIITLYLGAVVQA

DENV strain 4 envelope protein has the following sequence, identified as SEQ ID No. 5:

MRCVGVGNRDFVEGVSGGAWVDLVLEHGGCVTTMAQGKPTLDFELTKTTAK
EVALLRTYCIEASISNITTATRCPTQGEPYLKEEQDQQYICRRDVVDRGWG
NGCGLFGKGGVVTCAKFSCSGKITGNLVQIENLEYTVVVTVHNGDTHAVGN
DTSNHGVTATITPRSPSVEVKLPDYGELTLDCEPRSGIDFNEMILMKMKKK
TWLVHKQWFLDLPLPWTAGADTSEVHWNYKERMVTFKVPHAKRQDVTVLGS
QEGAMHSALAGATEVDSGDGNHMFAGHLKCKVRMEKLRIKGMSYTMCSGKF
SIDKEMAETQHGTTVVKVKYEGAGAPCKVPIEIRDVNKEKVVGRVISSTPL
AENTNSVTNIELEPPFGDSYIVIGVGNSALTLHWFRKGSSIGKMFESTYRG
AKRMAILGETAWDFGSVGGLFTSLGKAVHQVFGSVYTTMFGGVSWMIRILI
GFLVLWIGTNSRNTSMAMTCIAVGGITLFLGFTVQA

All flaviviruses, including West Nile Virus, St Louis encephalitis, dengue, Japanese encephalitis, yellow fever and kunjin viruses share similar size, symmetry and appearance. Despite the fact that flaviviruses may use different process to enter a host cell, such as endocytotis (described for West Nile Virus and Kunjin Virus) and direct fusion of the cell (described for dengue and Encephalitis Virus), entry of all flaviviruses into the host-cell involves an interaction between the virus and a receptor of the cell.

An alignment of the YFV 17D strain envelope protein of and all four strains of DENV envelope protein is displayed in FIG. 2. As used in this invention a "corresponding amino acid" is defined as follows. FIG. 2 may be used to calculate which amino acids of the DENV envelope protein corresponds to the amino acid of the YFV envelope protein. For example, FIG. 2 shows that the first amino acid of YFV envelope protein, alanine, corresponds to the first amino acid of all four strains of DENV envelope protein, methionine. By way of a further example, FIG. 2 may also be used to calculate that the $160^{th}$ amino acid of the YFV envelope protein, lysine, corresponds to the following amino acids of the four strains of DENV envelope protein, as shown in Table 1.

Table 1. An illustration of the correlation between YFV envelop protein and the four Dengue viral serotype envelop proteins, showing the correlating position and amino acid located at that position.

| DENV strain | Amino acid position | Amino acid |
| --- | --- | --- |
| DENV1 | 163$^{rd}$ | Threonine |
| DENV2 | 163$^{rd}$ | Lysine |
| DENV3 | 161$^{st}$ | Glutamic Acid |
| DENV4 | 163$^{rd}$ | Threonine |

A similar amino acid alignment may be created by practitioners in the art with other flavivirus envelope proteins, for example with West Nile Virus, St. Louis encephalitis, Dengue Fever virus, Japanese encephalitis, and Kunjin virus envelope proteins. These amino acid alignments could be used to determine which amino acid of the flavivirus envelope protein corresponded to any of the four strains of DENV envelope protein.

Any or all of amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of YFV envelope protein, SEQ ID No. 1, may be substituted with the corresponding amino acid of the desired strain of DENV envelope (E) protein to create the chimeric protein of the invention, using either a consensus from the DENV serotype sequences or utilizing the amino acid sequence from the DENV-2 serotype. The substitutions are made herein using site-directed mutagenesis, however changes to the flavivirus backbone may be made according to methods known to practitioners in the art.

In site directed mutagenesis, substitution of the yellow fever virus envelope protein are performed to create the chimeric protein. A mutated primer sequence having base pairs matching the vaccine construct sequence flanking the mutation was constructed. Alternatively, for primers containing multiple mutations, the mutations are surrounded by base pairs matching the construct, and base pairs matching the construct flanking the outermost mutations. The vaccine construct, formed of the envelope protein from a flavivirus, is inserted into a bacterial plasmid using methods known in the art, such as chemical transfection or electroporation, and the bacterial plasmid harvested by DNA extraction procedures. The bacterial plasmid, containing the E gene, is annealed with the primers using polymerase chain reaction (PCR), the temperature of which is typically around 60° C., but can be altered based on homology of the primer to the construct and percentage of G-C versus A-T in the sequence. PCR extension is performed on the primer, using the vaccine construct as a template, thereby forming a vaccine strand containing the DENV substitutions. The template E DNA is then degraded, leaving only the remaining specifically mutated DNA strand.

Human anti-dengue antibodies (4.8A, D11Ckl, and 1.6D) do not show strong neutralization activity against yellow fever virus, indicating that the yellow fever virus E protein lacks the important amino acid sequences that are recognized by these antibodies. Because the fusion loops of dengue and yellow fever are identical, the important amino acid positions lie outside of the fusion loop. An amino acid sequence alignment of the dengue and yellow fever E proteins, seen in FIG. 2, shows the differences between dengue and yellow fever that are responsible for antibody recognition.

Exchange of these dengue specific amino acid sequences into the yellow fever E protein yields a chimeric E protein that is immunogenic and results in antibodies that recognize and neutralize dengue via the E protein. This prevents fusion of the viral particle with the cell membrane, thereby denying the virus access to the cell.

Example 2

Testing of the yellow fever virus envelope protin backbone showed the E protein tertiary and quaternary structure were sufficiently homologous to permit a neutralizing response when site-directed substitutions of DENV amino acids were placed into the YFV backbone. Research has shown that flavivirus E proteins share a very similar structure, with regions that are highly conserved over the phylum, such as the fusion protein (Zhang, et al., Structures and functions of the envelope glycoprotein in flavivrus infections. Viruses. 2017 November; 9(11):338). In fact, the structure of the flavivrus E protein contains a helical anchor, a transmembrane of two cationic helices, an eight-stranded β-barrel EI domain, a highly-conserved loop EII domain, and a globular EIII region containing anti-parallel β-stands, and some helices (Zhang, et al., Structures and functions of the envelope glycoprotein in flavivrus infections. Viruses. 2017 November; 9(11):338). Accordingly, site directed mutagenesis of West Nile Virus, St. Louis encephalitis, Dengue Fever virus, Japanese encephalitis, and Kunjin virus, E protein with amino acids from one of the four strains of DENV envelope proteins will result in a useful vaccine against DENV.

Briefly, this method makes use of a short mutant DNA primer that binds specifically to the region being changed, but contains one or a small number of specific base changes that will result in a coding change to substitute the new specifically desired amino acid, as discussed in Example 1. The bacterial plasmid with the E gene is replicated using PCR amplification to generate new full-length mutant DNA strands. Then the original DNA strand is degraded, leaving only the remaining specifically mutated DNA strand Example 3

With the goal of understanding the human antibody response in naturally occurring DENV infections, hMAbs were isolated from peripheral blood B cells obtained from patients with distinct histories of DENV infection. Three patients, 7B, 8C, and DA003, contracted DENV in geographically distinct regions, Myanmar, Jamaica, and Singapore, respectively.

The collection and use of human blood samples was approved by various institutional review boards. Three patients were identified as having recovered from DENV infection. Patient 7B had acquired DENV while traveling in Myanmar. Blood was drawn from this patient 2 years post-hospitalization, as previously described (Schieffelin, et al., Neutralizing and non-neutralizing monoclonal antibodies against dengue virus E protein derived from a naturally infected patient. Virol. J. 2010 Feb. 4; 7:28). Patient DA003 was hospitalized in Singapore and had blood drawn approximately 4 weeks post-recovery. As DENV IgG antibodies were detected, in addition to IgM antibodies, the patient was diagnosed with secondary dengue infection with low disease severity, since no hemoconcentration or bleeding was present. Patient 8C contracted DENV in Jamaica and had blood drawn approximately 3 months post-recovery. The patient had fever for 12 days, headache, retro-orbital pain, and blood in sputum on day 10. No information on the type of DENV antibodies present was available from this patient. For all patients, blood was drawn after informed written consent was obtained, and peripheral blood mononuclear cells (PBMCs) were isolated by Ficoll-Hypaque gradient centrifugation and viably frozen in liquid nitrogen. Cryopreserved PBMC samples were collected at different times post-recovery (approximately 2 years for 7B, 3 months for 8C, and 4 weeks for DA003).

The patient sera were tested by ELISA and neutralization assays to positively determine infection with DENV. B-cell cultures were screened for antibody production using ELISA as described previously (Schieffelin, et al., Neutralizing and non-neutralizing monoclonal antibodies against dengue virus E protein derived from a naturally infected patient. Virol. J. 2010 Feb. 4; 7:28; Robinson, et al. A novel enzyme-linked immunosorbent assay (ELISA) for the detection of antibodies to HIV-1 envelope glycoproteins based on immobilization of viral glycoproteins in microtiter wells coated with concanavalin A. J. Immunol. Methods. 1990 Aug. 28; 132(1):63-71). Briefly, 96-well plates (Costar; Corning, Corning, N.Y.) were coated with ConA at 25 µg/ml in 0.01 M HEPES (Gibco) for 1 h. The wells were washed (PBS containing 0.1% [vol/vol] Tween 20), and Triton X-100-solubilized DENV produced in serum-free medium was incubated for 1 h. All steps in this ELISA were performed at room temperature. After a wash step, unreacted ConA binding sites in the wells were blocked with RPMI 1640 medium and 10% (vol/vol) FBS for 30 min. Samples from B-cell cultures were transferred to assay plates and incubated for 1 h. The wells were again washed and incubated with peroxidase-conjugated goat anti-human IgG-gamma (Zymed, San Francisco, Calif.) or peroxidase-conjugated affinity-purified anti-mouse IgG (Rockland, Gilbertsville, Pa.) diluted 1:2,000 in PBS containing 0.5% (vol/vol) Tween 20, 10% (wt/vol) whey (BiPro, Le Sueur, Minn.), and 10% (vol/vol) FBS for 1 h. After a final wash step, color was developed with tetramethylbenzidine-peroxide (TMB)-$H_2O_2$ as the substrate for peroxidase. The reaction was stopped after 4 min by adding 1% (vol/vol) phosphoric acid, and color was read as the optical density (OD) at 450 nm.

Figure 3A:
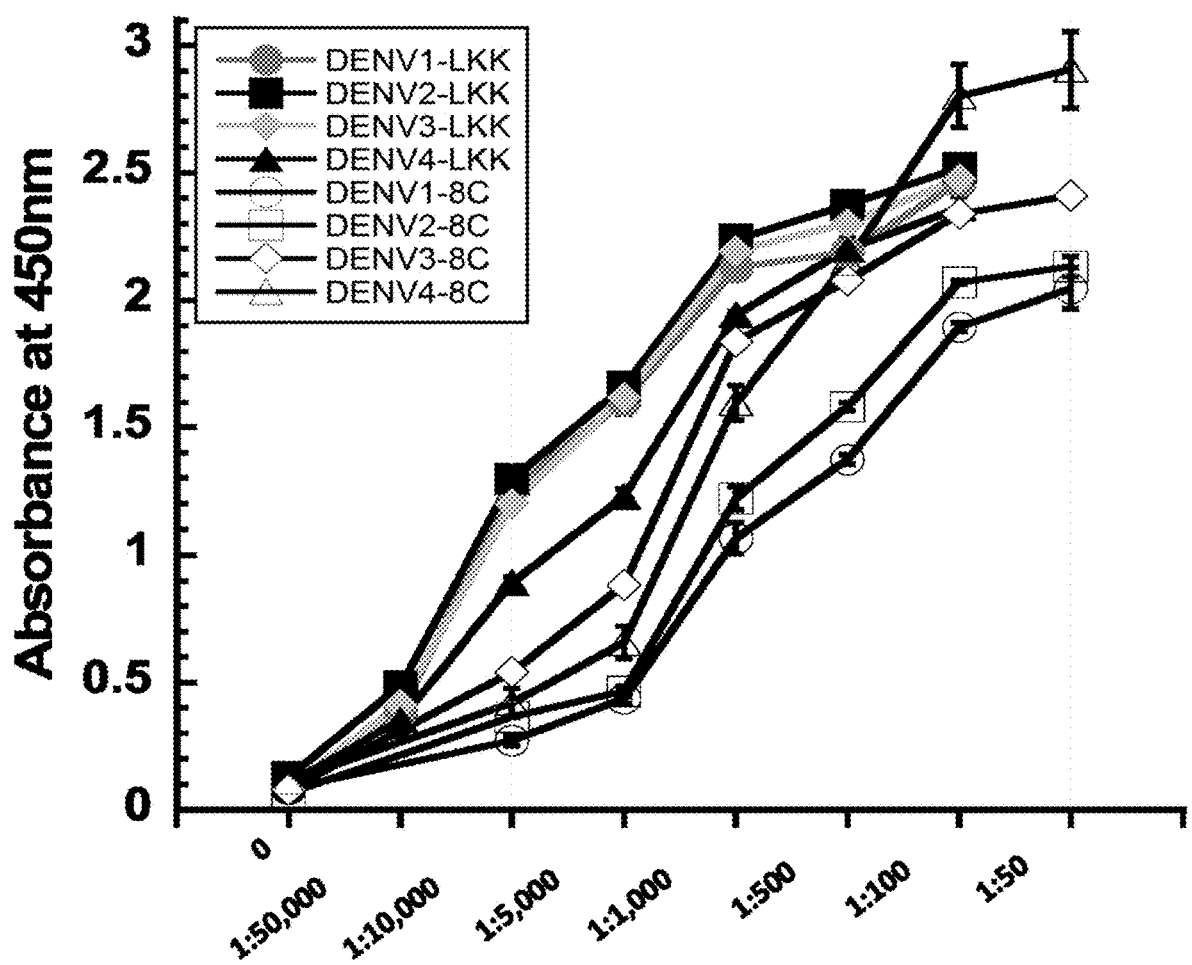
FIGS. 3(a) and (b) are graphs showing the results of ELISA assays with immobilized virus envelope glycoproteins. DENV-1, -2, -3, and -4 glycosylated antigens were captured on ConA-coated plates and (a) probed with dilutions of patient 8C and DA003 sera, or (b) dilutions of hMAbs D11C and 1.6D. The data points for (a) and (b) show the means of one experiment with three replicates. Error bars show standard deviations.

All three patients were confirmed seropositive to DENV antigens, as shown in FIG. 3(a) and reported previously for patient 7B (Schieffelin, et al., Neutralizing and non-neutralizing monoclonal antibodies against dengue virus E protein derived from a naturally infected patient. Virol. J. 2010 Feb. 4; 7:28).

From each patient, several hMAbs were produced, either by EBV transformation of B cells (7B and DA003) (Schieffelin, et al., Neutralizing and non-neutralizing monoclonal antibodies against dengue virus E protein derived from a naturally infected patient. Virol. J. 2010 Feb. 4; 7:28) or by memory B-cell stimulation, as discussed above, followed by molecular cloning (8C) (Pinna, et al., Clonal dissection of the human memory B-cell repertoire following infection and vaccination. Eur. J. Immunol. 2009 May; 39(5):1260-70; Liao, et al., High-throughput isolation of immunoglobulin genes from single human B cells and expression as monoclonal antibodies. J. Virol. Methods. 2009 June; 158(1-2):171-9).

hMAbs were produced using Epstein-Barr virus (EBV) transformation of B cells, as described previously (Schieffelin, et al., Neutralizing and non-neutralizing monoclonal antibodies against dengue virus E protein derived from a naturally infected patient. Virol. J. 2010 Feb. 4; 7:28; Robinson, et al. A novel enzyme-linked immunosorbent assay (ELISA) for the detection of antibodies to HIV-1 envelope glycoproteins based on immobilization of viral glycoproteins in microtiter wells coated with concanavalin A. J. Immunol. Methods. 1990 Aug. 28; 132(1):63-71; Robinson, et al., Identification of conserved and variant epitopes of human immunodeficiency virus type 1 (HIV-1) gp120 by human monoclonal antibodies produced by EBV-transformed cell lines. AIDS Res. Hum. Retrovir. 1990 May; 6(5):567-79; Xiang, et al., Characterization of CD4-induced epitopes on the HIV type 1 gp120 envelope glycoprotein recognized by neutralizing human monoclonal antibodies. AIDS Res. Hum. Retrovir. 2002 Nov. 1; 18(16):1207-17). Using this method, transformed clonal B cell lines were produced for hMAbs 4.8A (Schieffelin, et al., Neutralizing and non-neutralizing monoclonal antibodies against dengue virus E protein derived from a naturally infected patient. Virol. J. 2010 Feb. 4; 7:28) and D11C. Briefly, cryopreserved PBMCs were thawed, placed in culture, and inoculated with EBV (strain B95-8). The cells were resuspended in RPMI containing 20% (vol/vol) FBS, Primacin (InVivoGen, San Diego, Calif.), and 2 µg/ml CpG 2006 (Midland Certified Reagent Co., Midland, Tex.) and plated at $10^4$ cells per well in 96-well tissue culture plates. These plates had been previously seeded with approximately 50,000 irradiated mature macrophages per well derived from PBMCs of healthy blood donors that served as feeder cultures to promote outgrowth of transformed B cells. Antibody-positive wells containing viable cells were subcultured at several dilutions and rescreened by ELISA. Cell lines that continued to grow and produce antibody during several low-cell-density passages were finally cloned at limiting dilution. Definitively cloned cell lines were expanded to grow as suspension cultures in stationary 490-$cm^2$ roller bottle cultures (Corning, Corning, N.Y.) from which cell culture fluid was harvested weekly. hMAbs were purified from 1 to 2 liters of culture supernatant by protein A affinity chromatography. The IgG subclass and light-chain type of each antibody was determined by reactivity with mMAbs to the four heavy-chain subclasses (Southern Biotech, Birmingham, Ala.) and polyclonal goat antibodies to kappa and lambda chains by ELISA using established methods.

Alternatively, hMAbs were generated using transient stimulation of memory B cells as an alternative approach to EBV transformation (Pinna, et al., Clonal dissection of the human memory B-cell repertoire following infection and vaccination. Eur. J. Immunol. 2009 May; 39(5):1260-70). hMAb 1.6D was isolated using this method. Cryopreserved PBMCs were thawed and washed as described above and then resuspended in RPMI containing 20% (vol/vol) FBS, Primacin, 2.5 µg/ml R848, Toll-like receptor 7 (TLR7) and TLR8 agonist (InvivoGen, San Diego, Calif.), and 50 U/ml recombinant human interleukin-2 (Roche Diagnostics Corporation, Indianapolis, Ind.). After incubating for 3 days at 37° C. and 5% (vol/vol) $CO_2$, the cells were recounted and plated at 500 to $10^4$ cells per well in 96-well tissue culture plates containing feeder cells. To generate molecular clones of hMAbs, linear full-length Ig heavy- and light-chain gene expression cassettes were constructed as described previously (Liao, et al., High-throughput isolation of immunoglobulin genes from single human B cells and expression as monoclonal antibodies. J. Virol. Methods. 2009 June; 158 (1-2):171-9). Molecular clones were constructed for hMAbs 1.6D, from stimulated PBMCs, and D11C, from the transformed B-cell line. Briefly, RNA extracted from hMAb-positive B cells was reverse transcribed and cloned into gene expression cassettes. Purified PCR products of the paired Ig heavy- and light-chain gene expression cassettes were cotransfected into 80 to 90% confluent HEK-293T cells grown in 48-well tissue culture plates (300 ng of each chain per well) using Fugene Transfection Reagent (Roche Diagnostics Corporation, Indianapolis, Ind.) following the manufacturer's instructions. Transfection supernatants were tested for hMAb production against all four DENV serotypes by concanavalin A (ConA) ELISA. Positive cultures were seeded into 96-well plates in DMEM with 10% (vol/vol) FBS and 20 µg/ml Blasticidin S (InvivoGen) to ensure formation of stable hMAb-producing cell lines. Cultures were cloned by serial subculture at progressively lower cell densities in 96-well plates, with repeated antibody screening at each step.

To screen for hMAbs binding to glycosylated DENV proteins, an ELISA method, described previously, in which Triton X-100-solubilized DENV proteins were captured in ConA-coated wells of ELISA plates (Schieffelin, et al., Neutralizing and non-neutralizing monoclonal antibodies against dengue virus E protein derived from a naturally infected patient. Virol. J. 2010 Feb. 4; 7:28). This selection procedure likely biased identification toward cross-reactive hMAbs recognizing the E and prM proteins. Initial selection was done using DENV-2 (7B) or DENV-1 and -3 (8C and DA003). Based on ELISA reactivity to E proteins from all four DENV serotypes (for neutralizing activity, see below), 4.8A, D11C, and 1.6D were selected from patients 7B, DA003, and 8C, respectively.

Figure 3B:
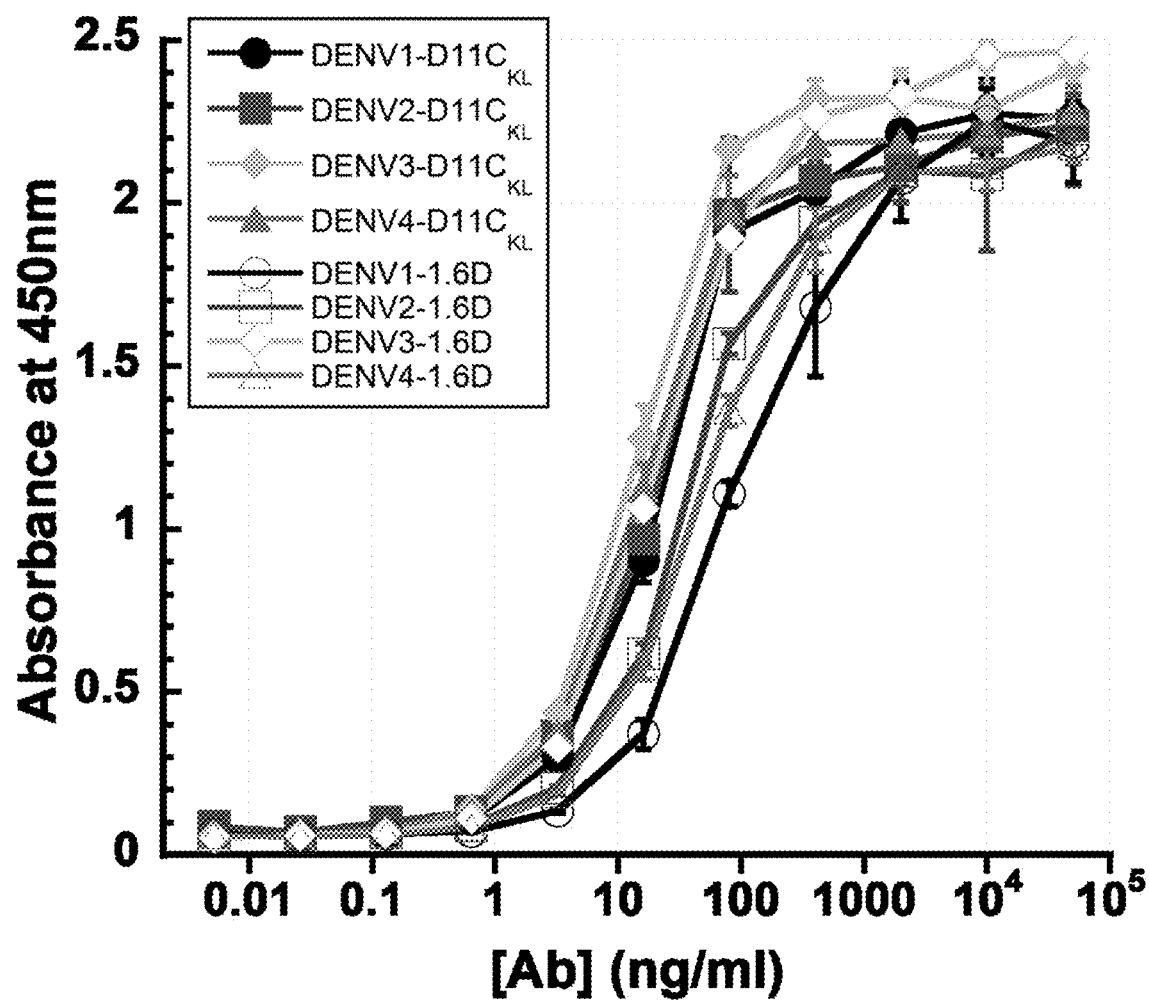

The broad reactivity is illustrated in FIG. 3(b) for hMAbs D11C and 1.6D and in Schieffelin et al. (Schieffelin, et al., Neutralizing and non-neutralizing monoclonal antibodies against dengue virus E protein derived from a naturally infected patient. Virol. J. 2010 Feb. 4; 7:28) for hMAb 4.8A. Because a number of different methods were used to isolate these antibodies, the percentage of the total repertoire the antibodies represented cannot be determined. However, as the antibodies were isolated from three out of three patients with different infection histories, it can be reasonably concluded that they are not uncommon. The three hMAbs were composed of IgG1 heavy chains and kappa light chains.

The hMAbs were subsequently tested to determine interaction with the different Dengue serotypes. *Macaca mulatta* kidney epithelial cell line LLC-MK$_2$ (American Type Culture Collection [ATCC], Manassas Va.), were grown in Dulbecco's modified Eagle medium (DMEM) containing 10% (vol/vol) fetal bovine serum (FBS), 2 mM Glutamax (Gibco, Carlsbad, Calif.), 100 U/ml penicillin G, 100 µg/ml streptomycin, and 0.25 µg/ml amphotericin B at 37° C. with 5% (vol/vol) CO$_2$. LLC-MK$_2$ cells were grown on no. 1.5 Gold Seal coverglass coverslips (Erie Scientific Company, Portsmouth, N.H.) placed in each well of a 6-well plate overnight to 80% confluence. Wells containing coverslips were infected with DENV in serum-free medium at a multiplicity of infection (MOI) of 0.002 for 1 h at 37° C. and aspirated; fresh culture medium was added, and the coverslips were incubated for 3 days at 37° C., with rocking.

Figure 4A:
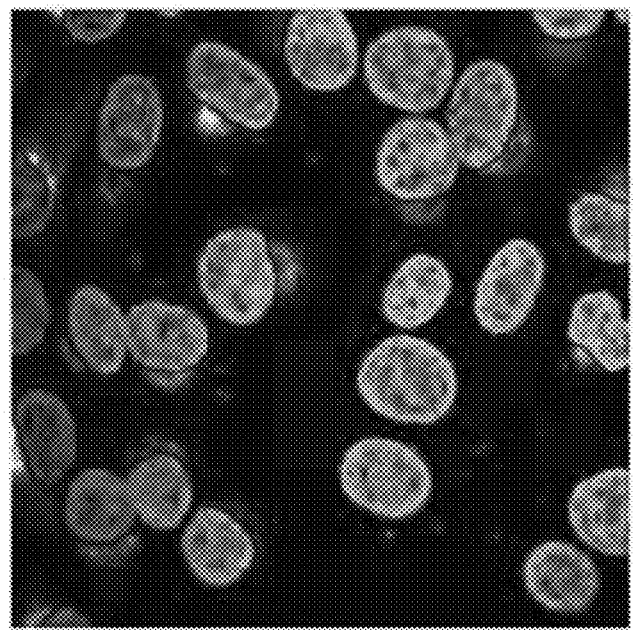
FIGS. 4(a) through (c) are microscopic images showing LLC-MK$_2$ cells infected with DENV-1 at an MOI of 0.002, probed with hMAbs (a) 4.8A, (b) D11C, and (c) 1.6D, and imaged by confocal microscopy. Nuclei were counterstained using Hoescht stain.
Figure 4B:
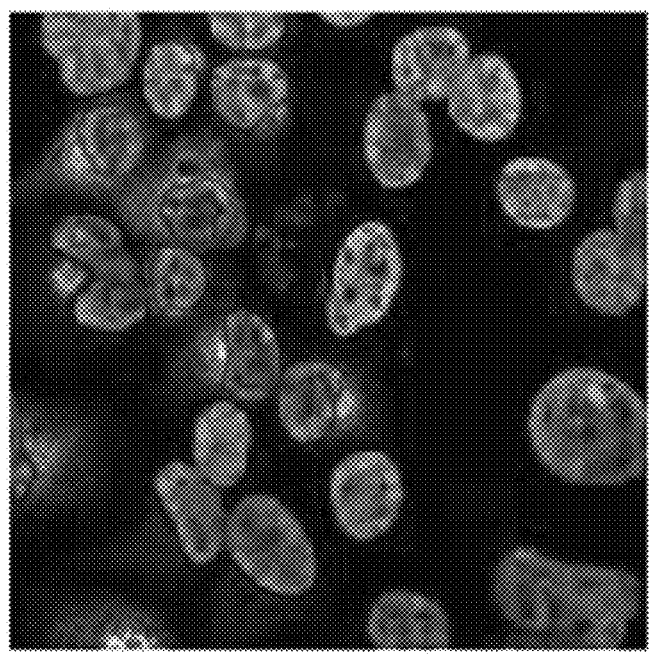
Figure 4C:
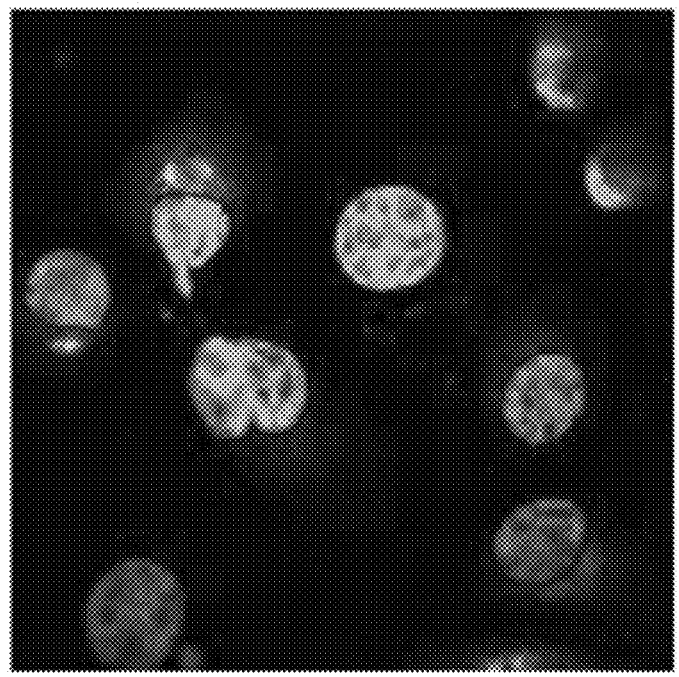
Figure 5A:
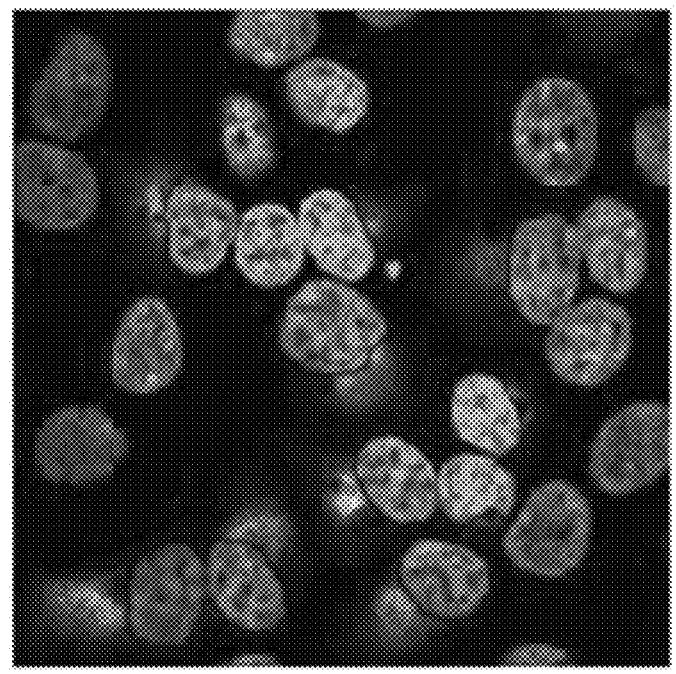
FIGS. 5(a) through (c) are microscopic images showing LLC-MK$_2$ cells infected with DENV-2 at an MOI of 0.002, probed with hMAbs (a) 4.8A, (b) D11C, and (c) 1.6D, and imaged by confocal microscopy. Nuclei were counterstained using Hoescht stain.
Figure 5B:
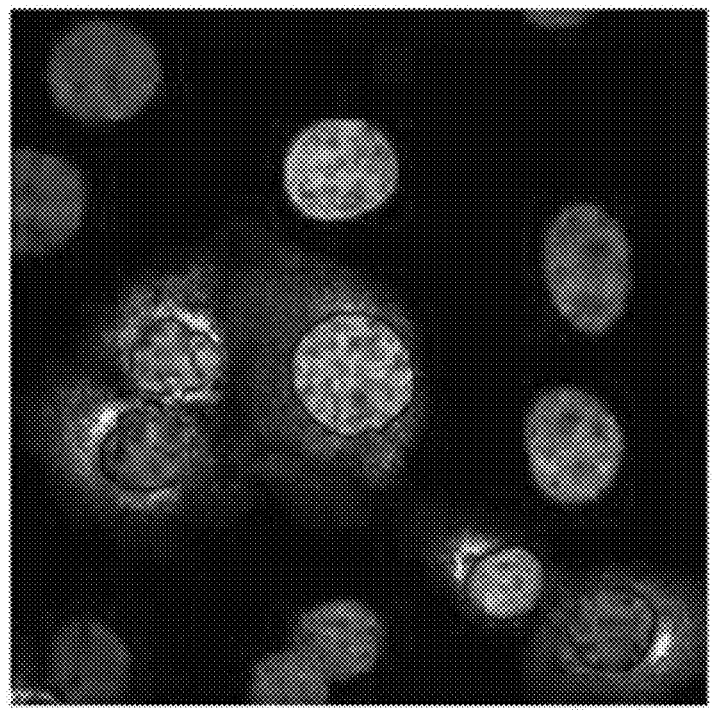
Figure 5C:
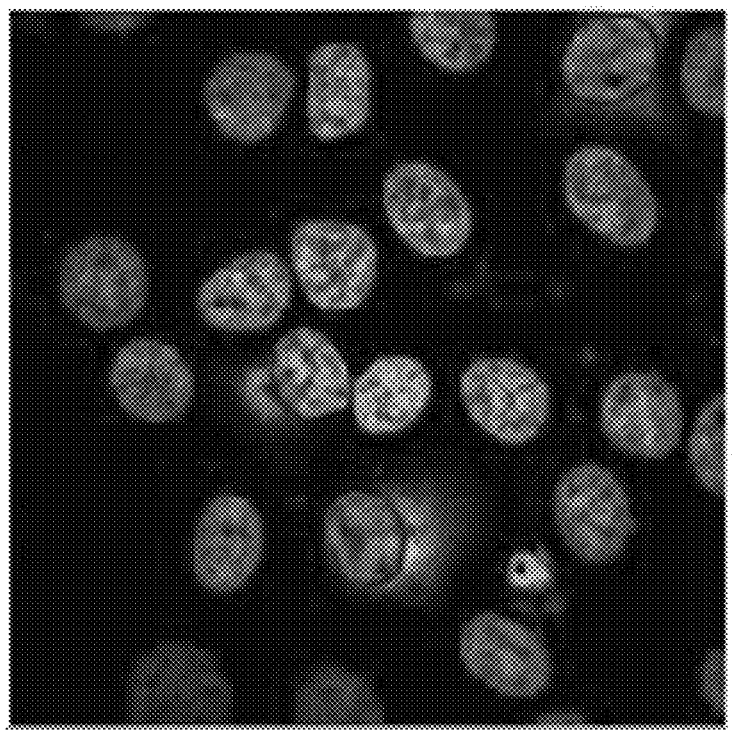
Figure 6A:
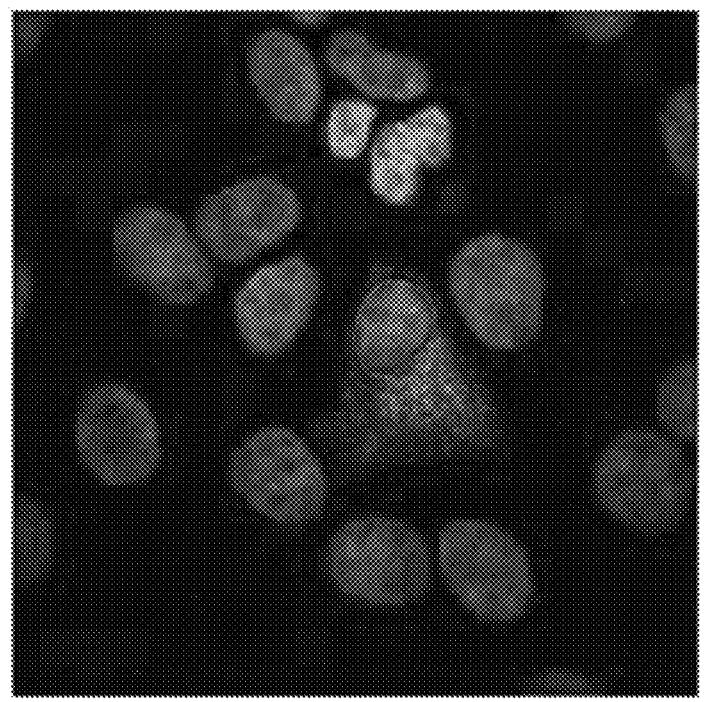
FIGS. 6(a) through (c) are microscopic images showing LLC-MK$_2$ cells infected with DENV-3 at an MOI of 0.002, probed with hMAbs (a) 4.8A, (b) D11C, and (c) 1.6D, and imaged by confocal microscopy. Nuclei were counterstained using Hoescht stain.
Figure 6B:
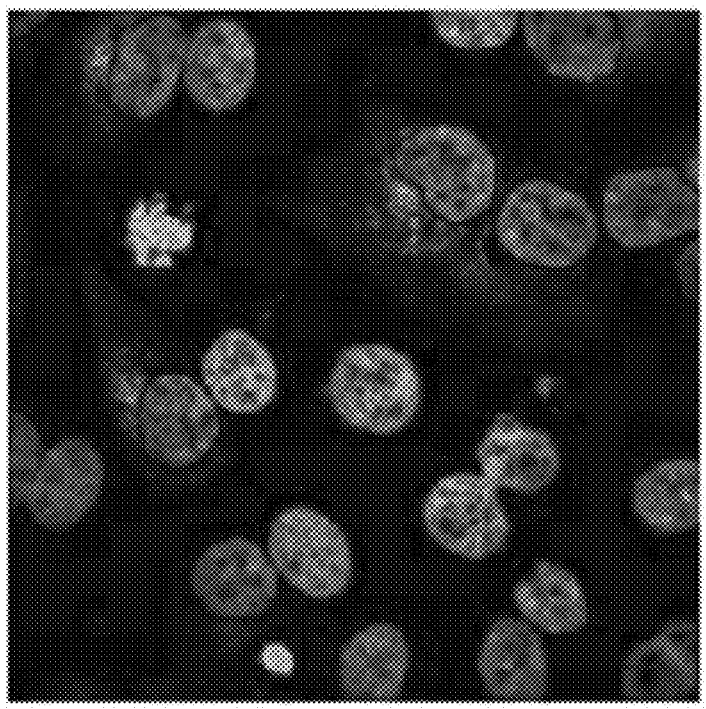
Figure 6C:
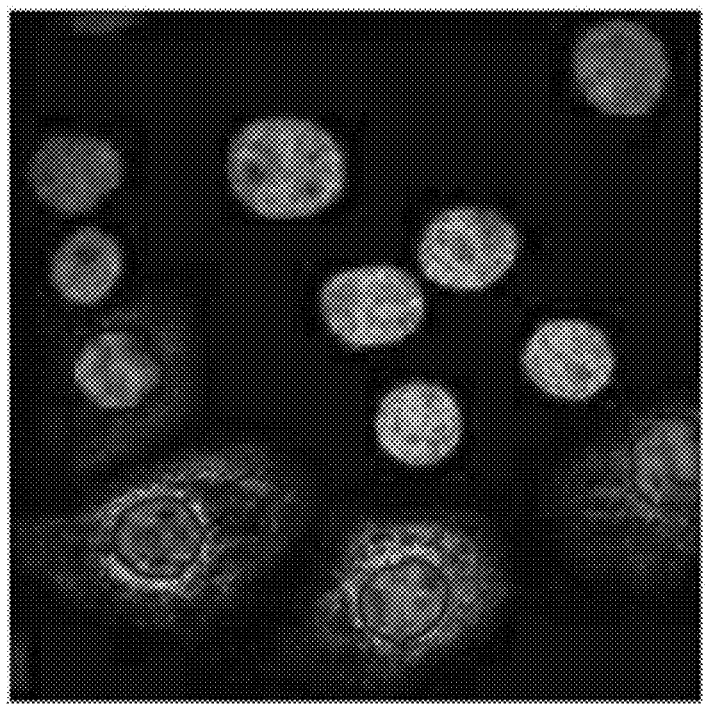
Figure 7A:
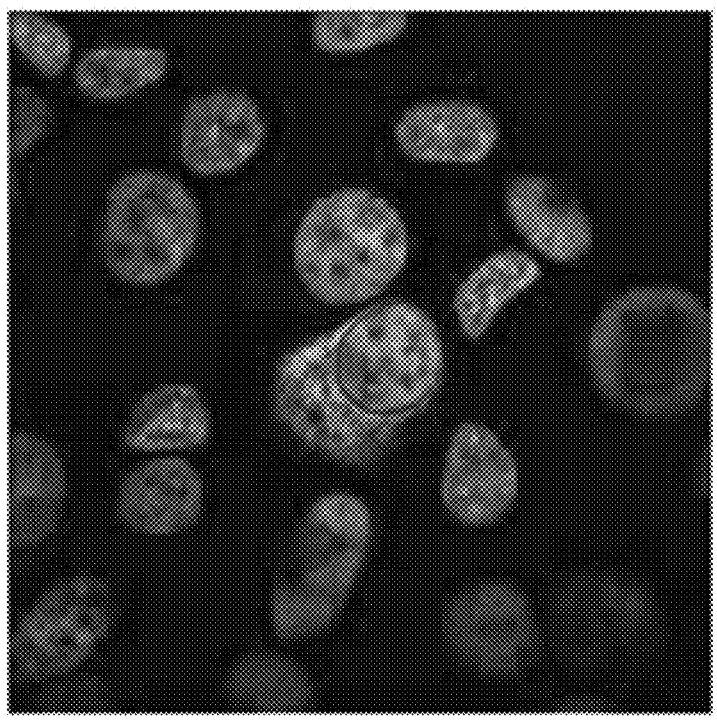
FIGS. 7(a) through (c) are microscopic images showing LLC-MK$_2$ cells infected with DENV-4 at an MOI of 0.002, probed with hMAbs (a) 4.8A, (b) D11C, and (c) 1.6D, and imaged by confocal microscopy. Nuclei were counterstained using Hoescht stain.
Figure 7B:
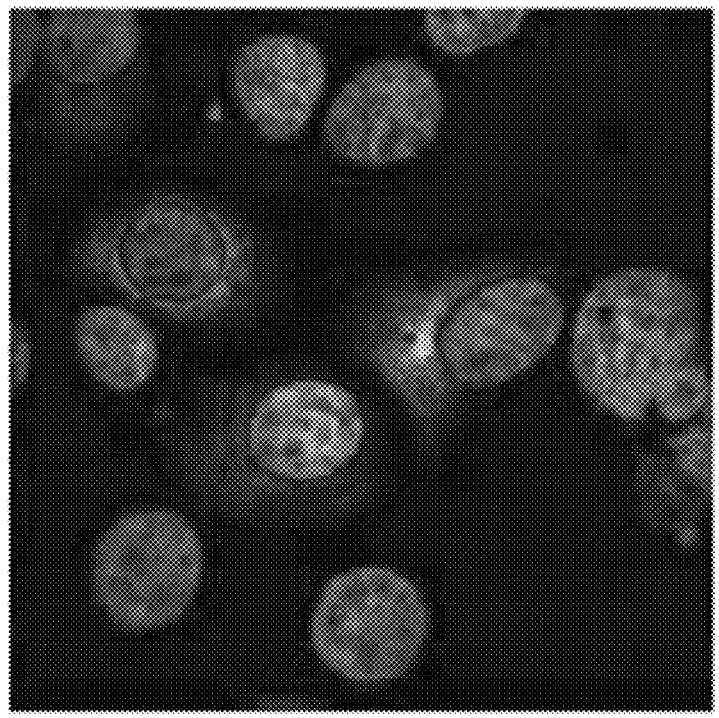
Figure 7C:
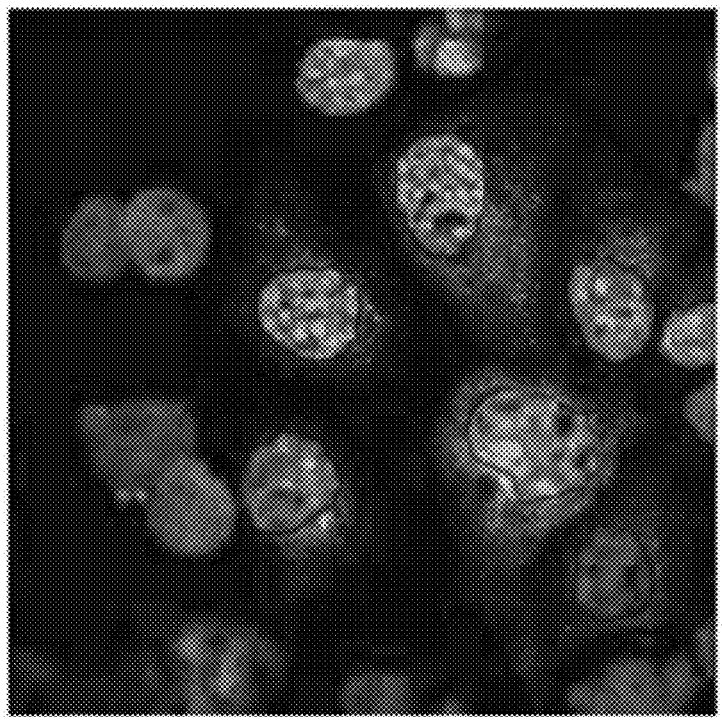

DENV-infected cells were imaged using confocal microscopy. Infected cultures were fixed with 10% (wt/vol) formalin overnight at 4° C., permeabilized with 70% (vol/vol) ethanol for 20 min, and rinsed with PBS prior to immunostaining. Virus proteins were detected using 1 µg/ml hMAb 4.8A, D11C, or 1.6D overnight at 4° C., followed by 2 µg/ml goat anti-human Alexa Fluor 488 (Invitrogen Corporation, Carlsbad, Calif.) for 4 h at room temperature. The cells were then counterstained with 2 µg/ml Hoechst stain (Cambrex, Walkersville, Md.) for 10 min at room temperature and washed with PBS. The coverslips were mounted on Fisherbrand Superfrost microscope slides (Fisher Scientific, Pittsburgh, Pa.) using Fluormount-G (Southern Biotech, Birmingham, Ala.) and visualized on an Olympus FV1000 Confocal Microscope System.

hMAbs 4.8A, D11C, and 1.6D were found to bind to DENV antigens expressed in DENV-1-, -2-, -3-, or -4-infected monkey epithelial LLC-MK$_2$ cells, using immunofluorescence assays. All three hMAbs exhibited a characteristic crescent-shaped perinuclear staining against all four DENV serotypes under fluorescence confocal microscopy. LLC-MK2 cells infected with DENV-1 exhibited low immunogenicity, directed around the nucleus, for serotypes 1 and 2 as seen by antibodies directed against DEN-1 and -2, as seen in FIGS. 4(a) and (c). Interestingly, antibodies directed against DENV-3 showed a higher immunogenicity than even DENV-1, as seen in FIG. 4(b). DENV-2 infected cells had higher signal intensity than DENV-1 infected cells, but shared similar staining patterns, with DENV-3 serotypes having higher antibody reactivity, seen in FIGS. 5(a) through (c). DENV-3 and -4 infected cells both showed moderate reactivity to DENV-2 and -3, and stronger reactivity toward DENV-1, as seen in FIGS. 6(a) through (c) and 7(a) through (c). No staining was observed in uninfected cells. The low virus MOI (0.002) used allowed a clear distinction between staining of virus-infected versus non-infected cells.

Studies on the human antibody response show that it is broadly neutralizing and potentially protective against all DENV serotypes have been poorly examined. Several other classes of DENV-neutralizing hMAbs are primarily serotype specific, including hMAbs that target E protein DIII (Dejnirattisai, et al., Cross-reacting antibodies enhance dengue virus infection in humans. Science. 2010 May 7; 328(5979): 745-8; Beltramello, et al., The human immune response to Dengue virus is dominated by highly cross-reactive antibodies endowed with neutralizing and enhancing activity. Cell Host Microbe. 2010 Sep. 16; 8(3):271-83; de Alwis, et al., In-depth analysis of the antibody response of individuals exposed to primary dengue virus infection. PLoS Negl. Trop. Dis. 2011 June; 5(6):e1188) and hMAbs that recognize quaternary epitopes between two E proteins (de Alwis, et al., Identification of human neutralizing antibodies that bind to complex epitopes on dengue virions. Proc. Natl. Acad. Sci. U.S.A. 2012 May 8; 109(19):7439-44; Teoh, et al., The structural basis for serotype-specific neutralization of dengue virus by a human antibody. Sci. Transl. Med. 4 2012 Jun. 20; 4(139):139ra83. doi:10.1126/scitranslmed.3003888). The results established the mechanism of action of broadly neutralizing antibodies produced in three human dengue patients. Though the hMAbs were isolated from patients from different countries and diverse ethnic backgrounds, with different infecting viruses, and at different times post-recovery, similar broadly neutralizing hMAbs were produced, suggesting that the target of these hMAbs is a common epitope that plays an important role in DENV infectivity.

Example 4

To confirm that the hMAbs recognize DENV E protein, Western blots were prepared using gradient-purified DENV-2 particles under reducing and nonreducing conditions and probed the blot strips with equal amounts (5 µg/ml) of hMAbs 4.8A, D11C, and 1.6D. Purified DENV-2; DENV-2 sE, produced as described previously (Modis, et al., A ligand-binding pocket in the dengue virus envelope glycoprotein. Proc. Natl. Acad. Sci. U.S.A. 2003 Jun. 10; 100(12):6986-91; Cuzzubbo, et al., Use of recombinant envelope proteins for serological diagnosis of Dengue virus infection in an immunochromatographic assay. Clin. Diagn. Lab. Immunol. 2001 November; 8(6): 1150-5) (Hawaii Biotech Inc., Aiea, Hi.); DENV-2 E sDI/II; and DENV-2 E sDIII (Meridian Life Science, Saco, Me.) were subjected to SDS-PAGE using 4 to 15% (wt/vol) or 15% (wt/vol) Tris-HCl polyacrylamide preparative gels for purified DENV-2 and soluble recombinant proteins, respectively (Bio-Rad, Hercules Calif.). Unless otherwise specified, samples were electrophoresed under non-reducing conditions in 25 mM Tris, 192 mM glycine, 3.5 mM SDS (Sigma-Aldrich, St. Louis, Mo.) and loaded in a buffer containing 0.7% (wt/vol) SDS. The reduced samples were loaded in a buffer containing 0.005% (wt/vol) SDS and 40 mM dithiothreitol (DTT). A Precision Plus protein Kaleidoscope ladder was used as a standard (Bio-Rad, Hercules, Calif.). Proteins were transferred to Amersham Hybond-LFP polyvinylidene difluoride (PVDF) membranes (GE Healthcare, Piscataway N.J.) in 25 mM Tris, 192 mM glycine, and 20% (vol/vol) methanol (Fisher, Pittsburgh Pa.), and membrane strips were blocked in 3% (wt/vol) bovine serum albumin (BSA) (Sigma-Aldrich, St. Louis, Mo.), 0.1% (vol/vol) Tween 20 in PBS and then probed overnight at 4° C. with 5 μg/ml of hMAbs 4.8A, D11C, and 1.6D; mMAbs 3H5.1 (Millipore, Billerica Mass.) specific for DENV-2 E DIII and 4G2 specific for DENV E DI/II; or 30% (vol/vol) cell culture supernatant mMAb D2-C2 specific for DENV-2 and -4 capsid protein (Liao, et al., High-throughput isolation of immunoglobulin genes from single human B cells and expression as monoclonal antibodies. J. Virol. Methods. 2009 June; 158(1-2):171-9) diluted in blocking buffer. The membrane strips were then incubated with Alexa Fluor 488-conjugated goat anti-human or anti-mouse antibody (Invitrogen, Carlsbad, Calif.) diluted in 0.1% (vol/vol) Tween 20 in PBS for 4 h at room temperature and rinsed in 0.1% (vol/vol) Tween 20 in PBS prior to scanning with a Typhoon Trio Variable Mode Imager (GE Healthcare, Piscataway N.J.). Photomultiplier tube (PMT) voltage settings used for detecting antibody binding on blot strips ranged from 220 V to 562 V depending on the primary-antibody-secondary-antibody combination. Increasing the PMT voltage increases the signal level, but not the signal-to-noise ratio. The PMT voltage values used for visualizing the individual blots are indicated in the figure legends.

Figure 8A:
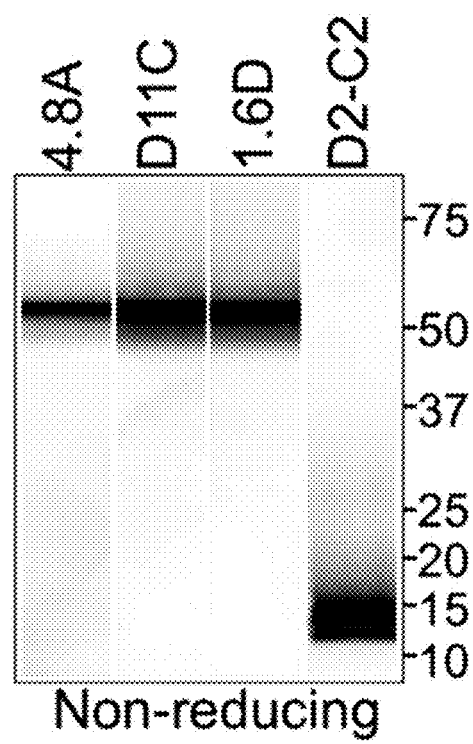
FIGS. 8(a) through (c) are blots showing antibody recognition of the E protein. Western blots were prepared with gradient-purified DENV-2 particles, and blots were probed with gMAbs 4.8A, D11C, and 1.6D or anti-DENV capsid mMAb D2-C2 (Puttikhunt, et al., Production and characterization of anti-dengue capsid antibodies suggesting the N terminus region covering the first 20 amino acids of dengue virus capsid protein is predominantly immunogenic in mice. Arch. Virol. 2009; 154(8):1211-21) under (a) nonreducing conditions or (b) reducing conditions. Binding of hMAbs to DENV-2 proteins on the blot strips was detected at a PMT voltage of 400 V. Protein standards are indicated by kilodaltons. (c) Western blots were prepared with DENV-2 sE, and blot strips were probed with hMAbs 4.8A, D11C, 1.6D, and control mMAbs 4G2 and 3H5.1 under nonreducing conditions. Binding of hMAbs and mMAbs to DENV-2 sE on the blot strips was detected at a PMT voltage of 220 V.
Figure 8B:
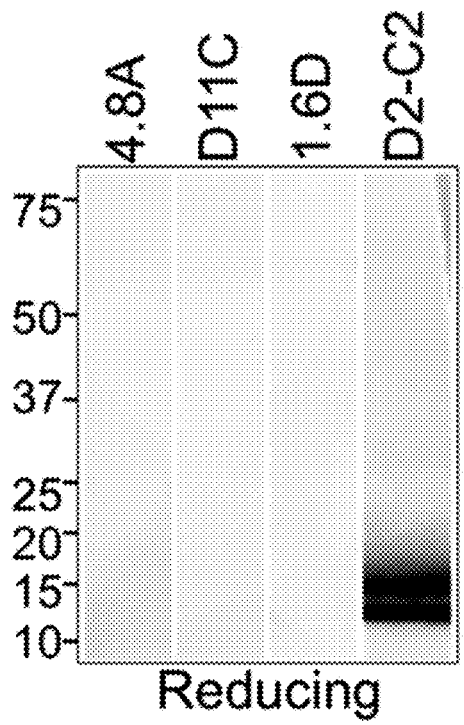
Figure 8C:
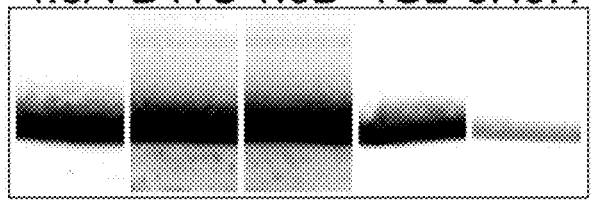

All three hMAbs recognized a 52-kDa band consistent with the size of DENV-2 E protein in non-reduced samples, seen in FIG. 8(a). No other bands were observed. The 52-kDa band was not present in reduced samples, seen in FIG. 8(b), indicating that all three hMAbs bound to epitopes dependent on disulfide bonds. As a control, an anti-DENV capsid mMAb, D2-C2 (Liao, et al., High-throughput isolation of immunoglobulin genes from single human B cells and expression as monoclonal antibodies. J. Virol. Methods. 2009 June; 158(1-2):171-9), recognized bands consistent with the size of DENV-2 capsid protein in both reduced and non-reduced samples. To confirm that the hMAbs bound specifically to E protein, Western blots were prepared under non-reducing conditions using recombinant DENV-2 sE, which contains the ectodomain of the E protein, and reacted blot strips with hMAbs 4.8A, D11C, and 1.6D, along with mMAbs 4G2 (Gentry, et al., Identification of distinct antigenic determinants on dengue-2 virus using monoclonal antibodies. Am. J. Trop. Med. Hyg. 1982 May; 31(3 Pt 1):548-55; Henchal, et al., Epitopic analysis of antigenic determinants on the surface of dengue-2 virions using monoclonal antibodies. Am. J. Trop. Med. Hyg. 1985 January; 34(1):162-9) and 3H5.1 (Sukupolvi-Petty, et al., Type- and subcomplex-specific neutralizing antibodies against domain III of dengue virus type 2 envelope protein recognize adjacent epitopes. J. Virol. 2007 December; 81(23):12816-26) as controls. A band consistent with the size of sE was observed for all hMAbs that was identical to the size of the bands recognized by the two control mMAbs specific for DENV E protein, as seen in FIG. 8(c).

To determine how tightly hMAbs 4.8A, D11C, and 1.6D bound to sE, biolayer interferometry binding assays were performed with hMAbs coupled to IgG binding sensors. Real-time competition assays between purified hMAb 1.6D and purified DENV-2 sE were performed using biolayer interferometry with an Octet QK system (Fortebio, Menlo Park, Calif.). To determine whether the hMAbs recognized overlapping or nonoverlapping sites, hMAb 1.6D was analyzed for competition with itself, as well as with mMAbs 4G2 and 3H5.1. Anti-HIV hMAb 1.7B was used as a negative control. Twenty-five micrograms per milliliter of hMAb 1.6D diluted in kinetics buffer containing 1 mM phosphate, 15 mM NaCl, 0.002% (vol/vol) Tween 20, 0.005% (wt/vol) sodium azide, 0.1 mg/ml (wt/vol) BSA, pH 7.4, in PBS was coupled with AHC biosensors (Fortebio, Menlo Park, Calif.). Unbound hMAb 1.6D was removed from the surfaces of the sensors by incubation in kinetics buffer. sE was preincubated with hMAb or mMAbs at a 1:1 molar ratio. hMAb 1.6D-coupled AHC sensors were then incubated with 50 nM sE, either prebound to antibodies or in kinetics buffer only. Association of sE with the hMAb 1.6D-coupled sensor was measured by light interference.

After removing unbound hMAbs, different concentrations of DENV-1, -2, -3, or -4 sE were incubated with the antibodies. Binding of the sE proteins to the hMAbs on the surfaces of the probes was measured by the change in interference from light reflected from the surface of the probe. After binding, the probes were placed in a solution without sE protein to similarly measure sE-hMAb dissociation. Antibody on and off rates and equilibrium dissociation constants were calculated assuming a 1:1 binding ratio. As expected from patient serum and the hMAb ELISA results, all three of the hMAbs bound to all four serotypes of DENV equally well, with equilibrium dissociation constants ($K_D$s) in the $10^{-9}$ to $10^{-10}$ M range, as seen in Table 2.

TABLE 2

Equilibrium dissociation constants of hMAbs 4.8A, D11C, and 1.6D bound to DENV-1, -2, -3, and -4 sE.

| DENV sE bound | Equilibrium $K_D$ (M) (mean ± SD) of hMAb: | | |
|---|---|---|---|
| | 4.8A | D11C | 1.6D |
| DENV-1 sE | $1.2 \times 10^{-9} \pm 1.6 \times 10^{-9}$ | $1.4 \times 10^{-10} \pm 1.2 \times 10^{-10}$ | $1.5 \times 10^{-10} \pm 5.0 \times 10^{-11}$ |
| DENV-2 sE | $1.3 \times 10^{-9} \pm 1.1 \times 10^{-9}$ | $1.2 \times 10^{-10} \pm 9.4 \times 10^{-11}$ | $3.5 \times 10^{-10} \pm 4.5 \times 10^{-10}$ |
| DENV-3 sE | $7.4 \times 10^{-10} \pm 7.7 \times 10^{-10}$ | $6.2 \times 10^{-10} \pm 3.2 \times 10^{-10}$ | $1.8 \times 10^{-10} \pm 8.0 \times 10^{-11}$ |
| DENV-4 sE | $7.6 \times 10^{-10} \pm 5.4 \times 10^{-10}$ | $2.9 \times 10^{-10} \pm 1.5 \times 10^{-10}$ | $2.4 \times 10^{-10} \pm 5.6 \times 10^{-11}$ |

The hMAbs reported here can individually block the binding of an mMAb recognizing the fusion loop, confirming that they share overlapping epitopes. However, mMAb prebound to E could not block binding by the hMAbs, indicating that the particular mMAb used either has a lower affinity than the hMAbs or that hMAbs bind to the fusion loop differently, in a manner that allows the hMAbs to displace the mMAb.

Antibodies directed against virus surface proteins are predicted to inhibit an early entry step into target cells. DENV enters through receptor-mediated endocytosis, where the E glycoprotein binds to a cellular receptor on the plasma membrane, followed by endocytosis and fusion of the viral and cellular membranes in the low-pH environment of endocytic vesicles, allowing the viral genome to enter target cells. To determine the details of the mechanism of neutralization, the effects of the antibodies were explored on different stages of viral entry.

The fusogenic activity of dengue virions toward liposomes was characterized using a novel high-throughput plate reader assay, a version of an assay described previously (Zaitseva, et al., Dengue virus ensures its fusion in late endosomes using compartment-specific lipids. PLoS Pathog. 2010 Oct. 7; 6(10):e1001131). Viral particles were labeled with the fluorescent lipid DiD (Vybrant cell-labeling kit; Molecular Probes, Eugene, Oreg.) in a self-quenching concentration, as described previously (Zaitseva, et al., Dengue virus ensures its fusion in late endosomes using compartment-specific lipids. PLoS Pathog. 2010 Oct. 7; 6(10): e1001131). Large unilamellar liposomes 100 nm in diameter were formed by an extrusion technique from the 1:1 (mol/mol) mixture of 1,2-dioleoyl-sn-glycero-3-phosphocholine (PC) and 1,2-dioleoyl-sn-glycero-3-phospho-(1'-rac-glycerol) (PG) (Avanti Polar Lipids, Alabaster, Ala.). DiD-labeled viral particles (~$10^5$ infectious units) in PBS without calcium and magnesium, pH 7.5, were incubated with different concentrations of the antibodies for 1 h at room temperature in a total volume of 50 µl. Virions preincubated with antibodies were then mixed in the wells of 96-well plates (3 wells for each condition) with acidified liposome-containing buffer (final concentration of PC and PG, 30 µM, pH 5.5). After 10 min of coincubation of virions and liposomes at acidic pH, the fluorescence was recorded at excitation and emission wavelengths of 630 and 665 nm. At the end of each recording (10 min of incubation at 22° C.), Triton X-100 was added to a final concentration of 0.1% (vol/vol) to fully dequench the DiD. The efficiency of fusion is presented as the difference between fluorescence intensities measured after 10 min of coincubation of labeled virions with liposomes at pH 5.5 and at pH 7.5 normalized to the difference between fluorescence intensities measured for fully dequenched DiD and at pH 7.5. In control experiments, dengue virions were inactivated by an application of a histidine-modifying reagent, diethylpyrocarbonate (DEPC) (Sigma, St. Louis, Mo.) (2 mM; 15 min; room temperature).

DENV-2 virions were labeled with DiD as described above. Virus-endosome fusion events were detected as an increase in cell fluorescence upon DiD dilution (Zaitseva, et al., Dengue virus ensures its fusion in late endosomes using compartment-specific lipids. PLoS Pathog. 2010 Oct. 7; 6(10):e1001131). MA104 cells (ATCC; ~$10^3$ cells/well) were grown overnight in 96-well microtiter plates (Ibidi, Verona, Wis.). The cells were then incubated for 30 min at 11° C., followed by 5 min at 37° C. with $10^4$ DiD-labeled infectious DENV-2 particles that had been preincubated with hMAbs in 100 µl of serum-free ADMEM for 1 h at room temperature. Unbound DENV-2 and hMAbs were removed by washing twice with 400 µl of serum-free ADMEM, and the cells were incubated for an additional 25 min at 37° C. For each well, images of 5 randomly chosen fields of view using a Zeiss Observer Z1 were captured (oil immersion objective; 40×; Carl Zeiss Microscopy, LLC, Thornwood, N.Y.) and generated maximum-intensity z projections based on 15 z-slices of 0.5 µm each for the subsequent analysis. The projections of the cells were analyzed using ImageJ software to subtract the background and threshold using the software's Triangle algorithm. For each condition, fluorescence intensities were averaged in 15 fields (5 fields for each of 3 wells). The data are presented as the mean and standard deviation of the mean for the averaged intensities (n=3) normalized to the averaged intensities measured for the cells incubated with DENV-2 in the absence of hMAbs.

After taking the images for the above-mentioned analysis, the effects of the hMAbs were examined on the total number of cell-associated virions using a novel assay that measured dequenching of DiD incorporated into unfused viral envelopes. MA104 cells incubated without DENV-2, with DENV-2 and 10 µg/ml of heparan sulfate, or with DENV-2 and 100 µg/ml of hMAb 4.8A, D11C, or 1.6D were lysed by a 15-min incubation with 0.1% (vol/vol) Triton X-100 at 37° C. The lysates were cleared by a 5-min centrifugation at 14,000×g, and 80 µl of each supernatant was mixed with 1,920 µl of a 20 mM HEPES, 150 mM NaCl, pH 7.5, buffer. Using a Fluoromax 4 Horiba Jobin Yvon spectrophotometer (Horiba Scientific, Edison, N.J.), the emission fluorescence was measured at 665 nm using an excitation wavelength of 600 nm. The data are presented as the mean and standard deviation of the mean of three independent experiments normalized to the fluorescence intensity measured for DENV-2-infected cells in the absence of hMAbs.

Figure 9:
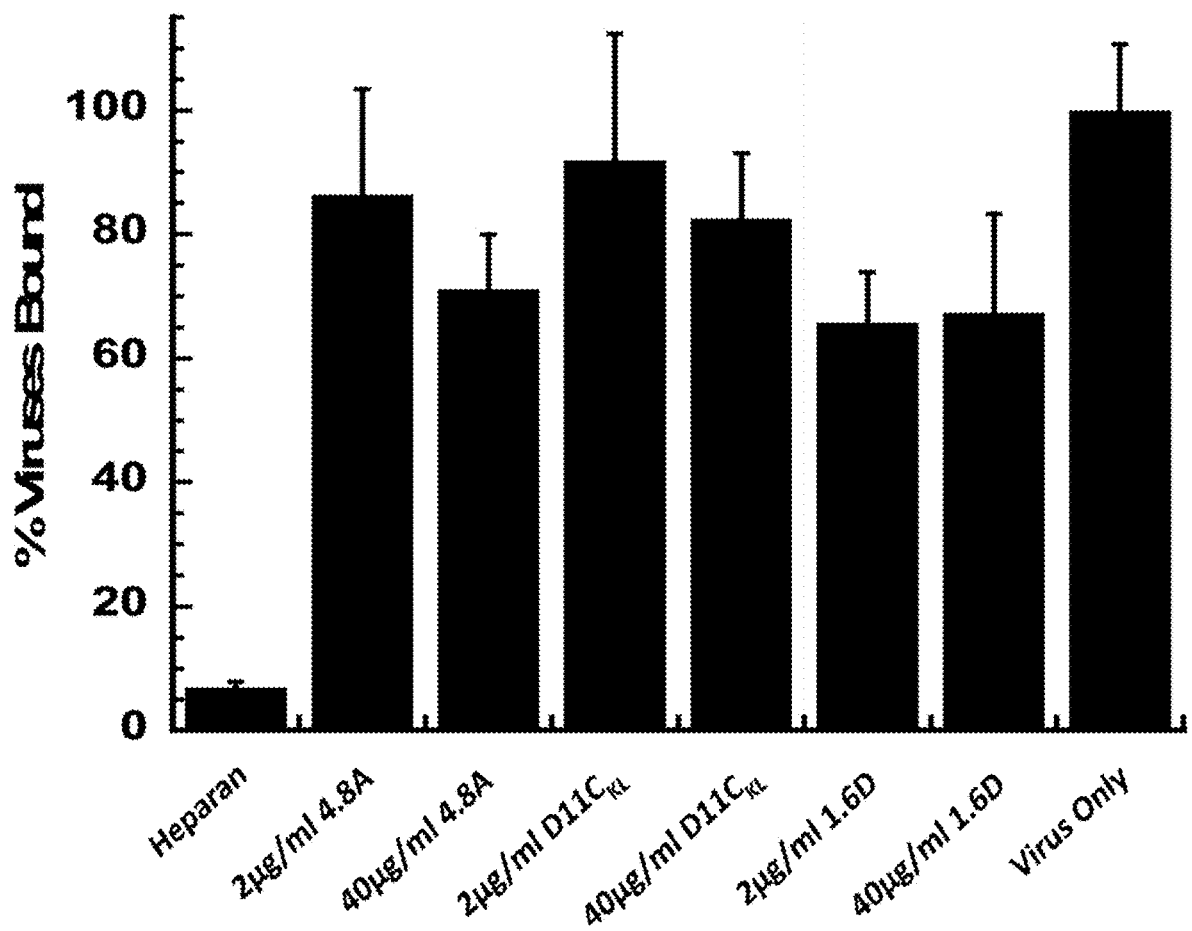
FIG. 9 is a graph showing the results from virus-cell binding inhibition assays performed in the presence of low-concentration and high-concentration monoclonal antibodies from DENV infected patients. Each data point is the mean of three replicates. The error bars indicate standard deviations.
Figure 10:
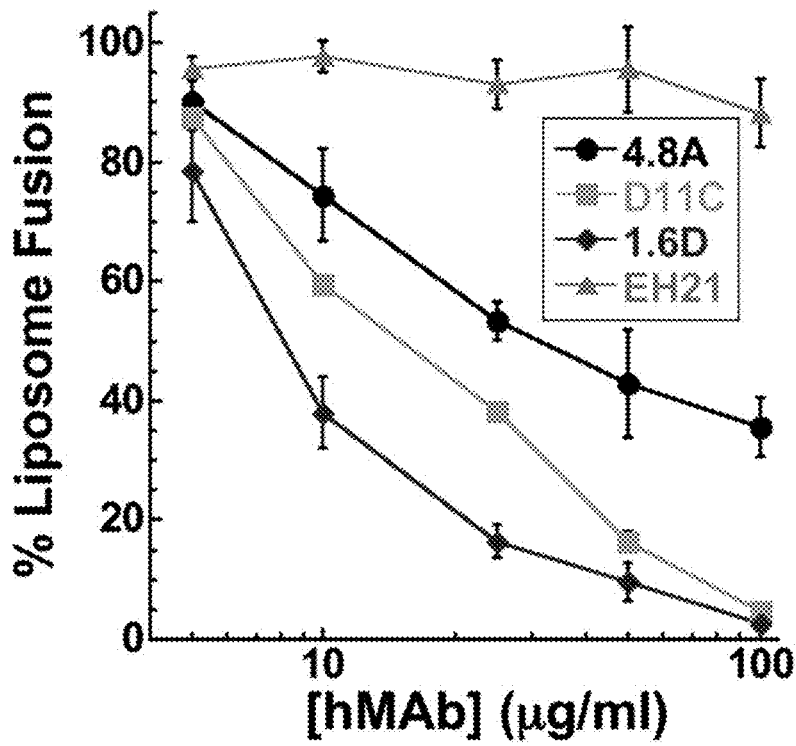
FIG. 10 is a graph showing viral liposome fusion. Low-pH-activated virus-liposome fusion was measured using fluorescently labeled DENV-2 incubated with hMAbs 4.8A, D11C, and 1.6D. The fluorescence signal was normalized to the signal generated in the absence of hMAbs to calculate percent liposome fusion. EH21 is an irrelevant anti-HIV hMAb. Each data point is the mean of three replicates. The error bars indicate standard deviations.
Figure 11A:
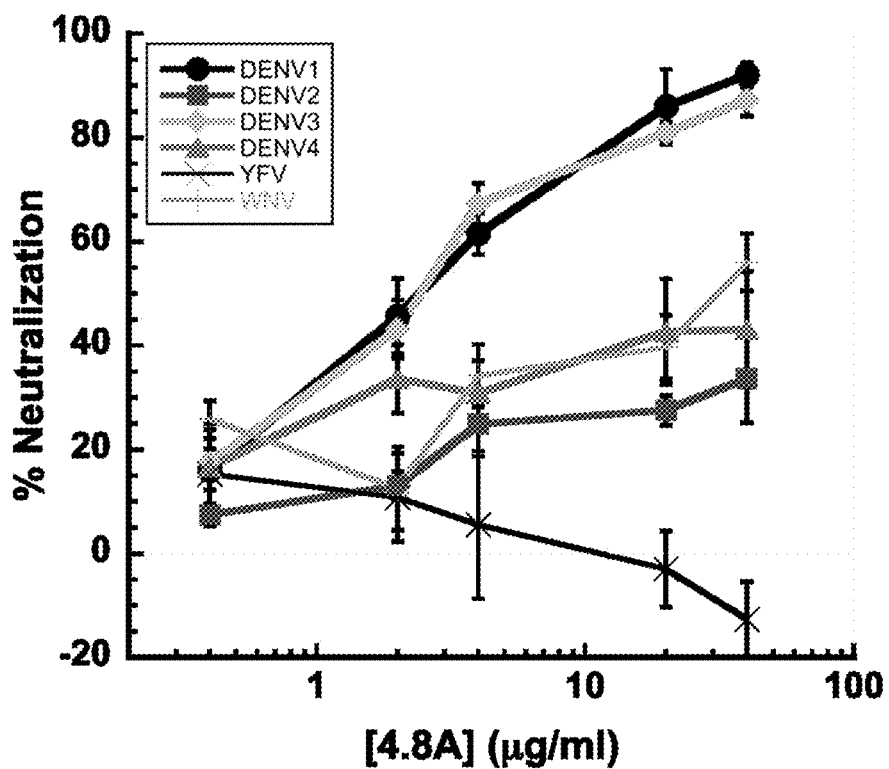
FIGS. 11(a) through (c) are graphs showing antigen neutralizing activity. Focus-forming-unit reduction neutralization assays were performed by incubating DENV-1, -2, -3, and -4 with serial dilutions of (a) hMAb 4.8A, (b) hMAb D11C, (c) hMAb 1.6D prior to infecting monolayers of LLC-MK2 cells. IC$_{50}$ (in µg/ml) were determined graphically and were as follows: hMAb 4.8A with DENV-1, 2.1±1.1, DENV-2, >40, DENV-3, 2.4±0.1, and DENV-4, >40; for hMAb D11C with DENV-1, 1.5±0.1, DENV-2, 1.0±0.4, DENV-3, 10.2±0.8, and DENV-4, 1.6±0.6; and for hMAb 1.6D with DENV-1, 1.5±1.1, DENV-2, 0.2±0.0, DENV-3, 0.5±0.1, and DENV-4, 2.7±0.8. The pooled data points show the means of at least two independent experiments with three replicates each. The error bars indicate standard deviations.
Figure 11B:
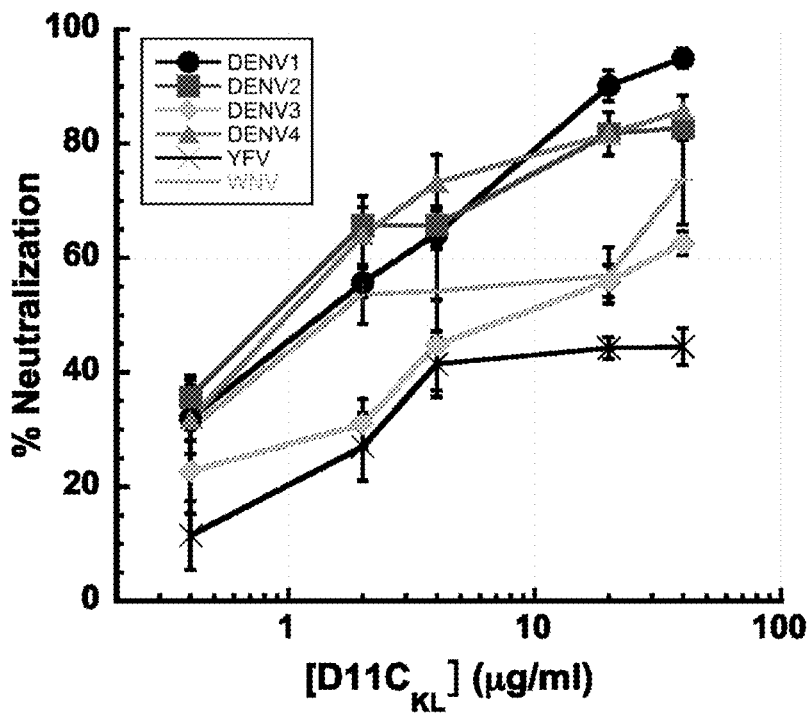
Figure 11C:
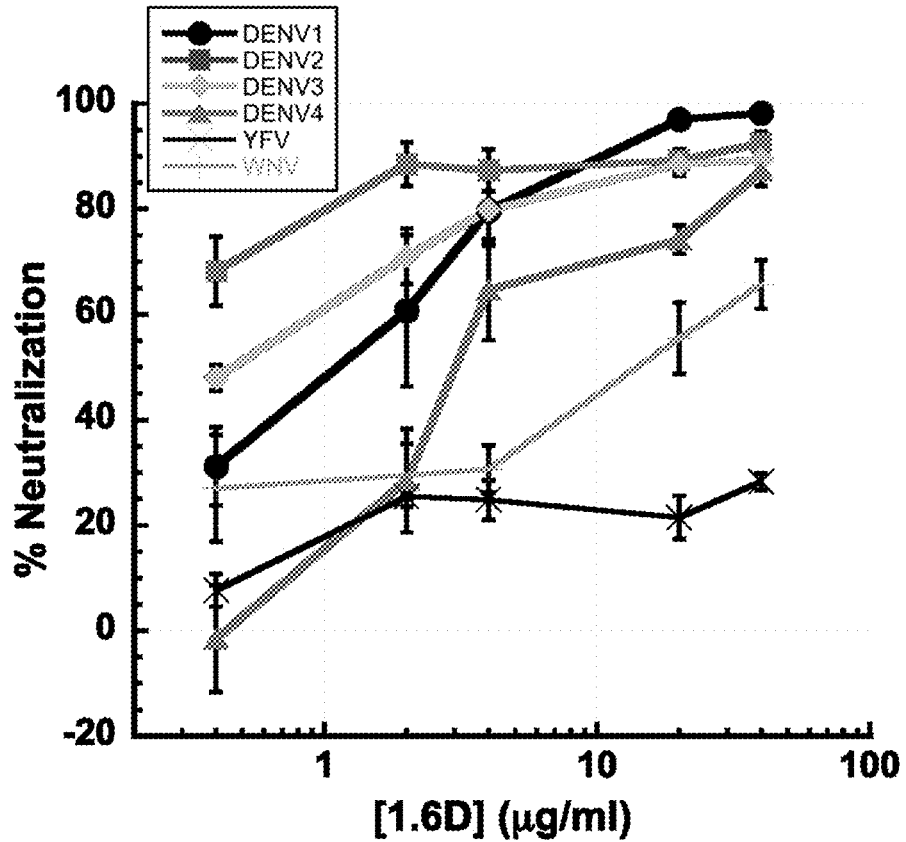

To investigate whether hMAbs could inhibit DENV-2 fusion, an assay that measures fusogenic activity of DENV particles toward liposomes was used (Zaitseva, et al., Dengue virus ensures its fusion in late endosomes using compartment-specific lipids. PLoS Pathog. 2010 Oct. 7; 6(10): e1001131; Cockburn, et al., Structural insights into the neutralization mechanism of a higher primate antibody against dengue virus. EMBO J. 2012 Feb. 1; 31(3):767-79). Initial tests showed a sharp decrease in viral fusion with MA104 cells when treated with high concentrations of DENV-2 antibodies, whereas DENV-1 antibodies did not show an appreciable effect on infection, as seen in FIG. 9. Use of heparin resulted in strong viral binding inhibition, as noted previously (Thaisomboonsuk, et al., Characterization of dengue-2 virus binding to surfaces of mammalian and insect cells. Am J Trop Med Hyg. 2005 April; 72(4):375-83) DENV-2 particles labeled with a self-quenching concentration of a fluorescent lipid, DiD, were pretreated with hMAbs prior to coincubation with liposomes at acidic pH. Lipid mixing between labeled viral and unlabeled liposomal membranes was monitored as an increase in fluorescence, reflecting DiD dilution. As expected, no increase in the fluorescence, and thus no lipid mixing, was observed for virions inactivated by a histidine-modifying reagent, diethylpyrocarbonate (Zaitseva, et al., Dengue virus ensures its fusion in late endosomes using compartment-specific lipids. PLoS Pathog. 2010 Oct. 7; 6(10):e1001131). In contrast to the negative-control anti-HIV gp120 hMAb EH21, all three anti-DENV E hMAbs strongly inhibited virus-liposome fusion in a dose-dependent manner, as seen in FIG. 10. The relative fusion-inhibiting activities of the hMAbs, with 1.6D being the most potent and 4.8A the least potent, corresponded to their relative neutralization activities, as seen in FIGS. 11(a) through (c).

With the goal of determining the mechanism of neutralization, using a novel assay, DENV binding to target cells was uncoupled from fusion. It was discovered that the neutralization activity of the hMAbs correlated with inhibition of fusion rather than virus-cell binding.

A common theme among different structural classes of enveloped virus fusion proteins is the existence of an internal or N-terminal hydrophobic fusion loop or fusion peptide. Neutralizing antibodies directed against these fusion regions have been well described in other virus systems, including closely related flaviviruses (Cherrier, et al., Structural basis for the preferential recognition of immature flaviviruses by a fusion-loop antibody. EMBO J. 2009 Oct. 21; 28(20):3269-76), more distantly related alphaviruses (Hammar, et al., Prefusion rearrangements resulting in fusion peptide exposure in Semliki forest virus. J. Biol. Chem. 2003 Feb. 28; 278(9):7189-98), and unrelated orthomyxoviruses (Hashem, et al., Universal antibodies against the highly conserved influenza fusion peptide cross-neutralize several subtypes of influenza A virus. Biochem. Biophys. Res. Commun. 2010 Dec. 10; 403(2):247-51). The results are consistent with those of a recent study that identified two other broadly neutralizing hMAbs from a single patient that target DENV DI/II and whose binding to WNV DI/II was ablated when residues in the fusion loop were altered, suggesting that these antibodies may also bind to the DENV fusion loop (Beltramello, et al., The human immune response to Dengue virus is dominated by highly cross-reactive antibodies endowed with neutralizing and enhancing activity. Cell Host Microbe. 2010 Sep. 16; 8(3): 271-83). Importantly, reports focusing on polyclonal antibody fractions from DENV patient-derived serum have shown that the predominant fraction of the broadly neutralizing activity targets DI/II and specifically the fusion loop, consistent with the hMAb results (Lai, et al., Antibodies to envelope glycoprotein of dengue virus during the natural course of infection are predominantly cross-reactive and recognize epitopes containing highly conserved residues at the fusion loop of domain II. J. Virol. 2008 July; 82(13): 6631-43; Lin, et al., Analysis of epitopes on dengue virus envelope protein recognized by monoclonal antibodies and polyclonal human sera by a high throughput assay. PLoS Negl. Trop. Dis. 2012 January; 6(1):e1447; Wahala, et al., Dengue virus neutralization by human immune sera: role of envelope protein domain III-reactive antibody. Virology. 2009 Sep. 15; 392(1):103-13). Broadly neutralizing chimpanzee MAbs and mMAbs targeting the DENV fusion loop have been described previously (Gentry, et al., Identification of distinct antigenic determinants on dengue-2 virus using monoclonal antibodies. Am. J. Trop. Med. Hyg. 1982 May; 31(3 Pt 1):548-55; Henchal, et al., Epitopic analysis of antigenic determinants on the surface of dengue-2 virions using monoclonal antibodies. Am. J. Trop. Med. Hyg. 1985 January; 34(1):162-9; Goncalvez, et al., Monoclonal antibody-mediated enhancement of dengue virus infection in vitro and in vivo and strategies for prevention. Proc. Natl. Acad. Sci. U.S.A. 2007 May 29; 104(22):9422-7).

Figure 12:
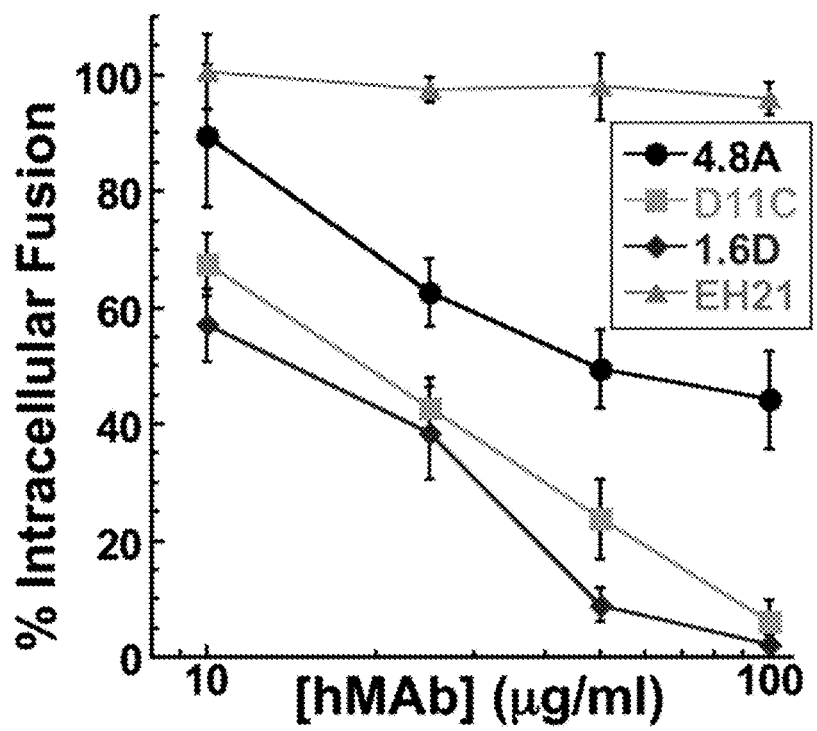
FIG. 12 is a graph showing intracellular fusion of DiD-labeled DENV-2 within endosomes leads to dequenching of DiD. Confluent monolayers of MA104 cells were infected with equivalent amounts of DENV-2 preincubated with or without 100 µg/ml hMAbs, as indicated. Intracellular structures at the site of fusion events fluoresce red. Cells were counterstained with DAPI to visualize nuclei and fusion levels quantified after incubation of DENV-2 with different concentrations of hMAbs. Fluorescence levels were normalized to those of virus-only controls. Each data point is the mean of three replicates. The error bars indicate standard deviations.

Since virus-liposome fusion relies on random collisions between virions and liposomes rather than on E-mediated virion-liposome binding, the ability of hMAbs 4.8A, D11C and 1.6D to inhibit fusion between virions and liposomes suggested that viral entry in vivo might also be inhibited at the fusion stage of the entry. To test this hypothesis, the effects of the antibodies on intracellular fusion of DENV-2 and on the prefusion stages of viral entry into rhesus macaque kidney epithelial (MA104) cells was directly examined. For DENV-2 labeled with DiD at a self-quenching concentration, fusion events along the endocytic pathway dilute DiD and thus lead to an increase in fluorescence signal (Zaitseva, et al., Dengue virus ensures its fusion in late endosomes using compartment-specific lipids. PLoS Pathog. 2010 Oct. 7; 6(10):e1001131; Ayala-Nunez, et al., Monitoring virus entry into living cells using DiD-labeled dengue virus particles. Methods. 2011 October; 55(2):137-43. doi: 10.1016/j.ymeth.2011.07.009. Epub 2011 Aug. 10; van der Schaar, et al., Characterization of the early events in dengue virus cell entry by biochemical assays and single-virus tracking. J. Virol. 2007 November; 81(21):12019-28. Epub 2007 Aug. 29). The efficiency of intracellular fusion was quantified by measuring cell fluorescence with a novel microtiter plate version of the assay described previously (Zaitseva, et al., Dengue virus ensures its fusion in late endosomes using compartment-specific lipids. PLoS Pathog. 2010 Oct. 7; 6(10):e1001131). Virions were preincubated with the antibodies and then applied to the cells at 11° C. for 30 min to permit binding while holding the virions in a temperature-arrested state. The temperature was then raised to 37° C. to allow uptake and fusion of the virions. After the first 5 min of incubation at 37° C., unbound virions and antibodies were removed by rinsing and, after 25 additional minutes, assayed intracellular fusion by fluorescence microscopy, and the results quantified, as seen in FIG. 12. Fusion of DiD-labeled virus within endosomes leads to dequenching of DiD and the appearance of brightly fluorescent intracellular structures. Cells were counterstained with DAPI (4',6-diamidino-2-phenylindole) to visualize the nuclei. All three anti-DENV hMAbs inhibited intracellular fusion in a dose-dependent manner, seen in FIG. 12, corresponding to their relative inhibiting activities in viral neutralization and virus-liposome fusion assays (1.6D was the most potent and 4.8A the least potent), as seen in FIGS. 11(a) through (c) and 10. In contrast, a control anti-HIV gp120 hMAb, EH21, did not inhibit intracellular fusion. These results suggest that 4.8A, D11C, and 1.6D directly interfere with the structural transitions required for the virus to fuse to the endosomal membrane.

Figure 13:
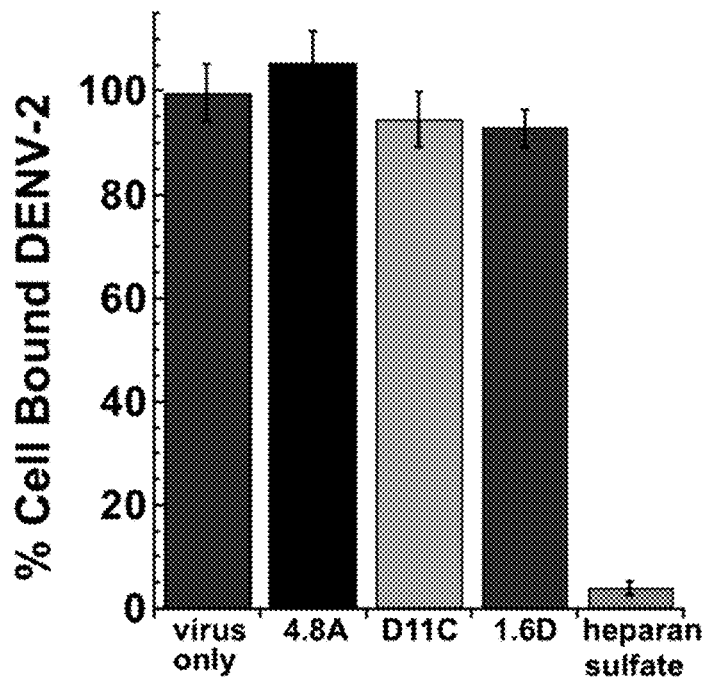
FIG. 13 is a graph showing total fluorescence of all bound DENV-2 was quantified by fully dequenching the cells. DENV-2 was incubated with 100 µg/ml of each hMAb. Fluorescence levels were normalized to those of virus-only controls. Heparan sulfate at 10 µg/ml, a known inhibitor of DENV binding, was used as a positive control for binding inhibition. Each data point is the mean of three replicates. The error bars indicate standard deviations.

For virions to reach endosomes and fuse, they must first bind to the cell surface and undergo internalization. In order to test whether the formed hMAbs inhibited virus-cell binding, the total number of virions associated with cells must be evaluated, including (i) cell surface-bound virions, (ii) internalized but yet unfused virions, and, finally, (iii) fused virions. Note that when fusion was measured after a 30-min incubation at 37° C., fused virions represented only a small fraction of all cell-associated virions (van der Schaar, et al., Characterization of the early events in dengue virus cell entry by biochemical assays and single-virus tracking. J. Virol. 2007 November; 81(21):12019-28. Epub 2007 Aug. 29) and only fused virions were dequenched. After measuring the intracellular fusion efficiency, the cells were lysed and fully dequenched the DiD probe in all unfused virions, using Triton X-100 to disrupt the viral membranes. The level of unquenched DiD fluorescence was therefore proportional to the total number of cell-associated virions and thus can be used to evaluate the effects of different reagents on virus-cell binding, seen in FIG. 13. As expected, heparan sulfate (10 µg/ml), which inhibits DENV binding to cells (Chen, et al., Dengue virus infectivity depends on envelope protein binding to target cell heparan sulfate. Nat. Med. 1997 August; 3(8):866-71), dramatically lowered the numbers of cell-associated virions, and consequently, the DiD fluorescence of cell lysates. Preincubation of virions with high concentrations of the hMAbs (100 µg/ml, sufficient to profoundly inhibit intracellular fusion) had no effect on cell lysate DiD fluorescence intensity, indicating that these antibodies do not appreciably affect virus-cell binding. These findings demonstrate that hMAbs 4.8A, D11C, and 1.6D block viral infection downstream of virus-cell binding at the stage of virus-endosome fusion.

Interestingly, hMAb 4.8A did not completely suppress DENV-2 fusion even at very high concentrations, correlating with the observed neutralization activity of this hMAb against DENV-2. The inability of some antibodies to completely neutralize infection and fusion has been previously reported (Cockburn, et al., Structural insights into the neutralization mechanism of a higher primate antibody against dengue virus. EMBO J. 2012 Feb. 1; 31(3):767-79; Dowd, et al., A dynamic landscape for antibody binding modulates antibody-mediated neutralization of West Nile virus. PLoS Pathog. 2011 June; 7(6):e1002111; Thompson, et al., A therapeutic antibody against West Nile virus neutralizes infection by blocking fusion within endosomes. PLoS Pathog. 2009 May; 5(5):e1000453; Vogt, et al., Human monoclonal antibodies against West Nile virus induced by natural infection neutralize at a postattachment step. J. Virol. 2009 July; 83(13):6494-507), suggesting that even at saturation these antibodies only partially neutralize the fusogenic activity of each E protein. Alternatively, the epitopes at some of the viral surface E proteins may be inaccessible, reflecting the heterogeneity of virions and/or E protein chemical environments. For all three hMAbs, inhibition of lipid mixing required somewhat higher concentrations of hMAbs than virus neutralization. This could reflect different conditions (in the neutralization assay, $10^2$ infectious units were used versus $10^5$ and $10^4$ infectious units in liposome and intracellular fusion assays, respectively). This difference may also indicate that for DENV, as for several other viruses (Chernomordik, et al., Protein-lipid interplay in fusion and fission of biological membranes. Annu. Rev. Biochem. 2003; 72:175-207; Cohen, et al., The energetics of membrane fusion from binding, through hemifusion, pore formation, and pore enlargement. J. Membr. Biol. 2004 May 1; 199(1):1-14), early stages of viral fusion (detected as lipid mixing in the assay) require fewer functional fusion proteins and thus are more difficult to inhibit than opening of a fusion pore large enough to release viral RNA, a prerequisite for viral infection. As a result, at neutralizing concentrations of the antibodies, virions may still have enough functional (i.e., not antibody bound) fusion proteins to mediate lipid mixing.

Taken together, the results show that hMAbs 4.8A, D11C, and 1.6D neutralize infection by inhibiting E protein-mediated membrane fusion rather than prefusion stages of viral entry.

Example 5

Neutralizing antibodies were analyzed in patient sera using focus-forming-unit reduction neutralization assays in monkey epithelial LLC-MK$_2$ cells in which serial dilutions of patient sera were incubated with DENV-1, -2, -3, or -4.

Figure 14:
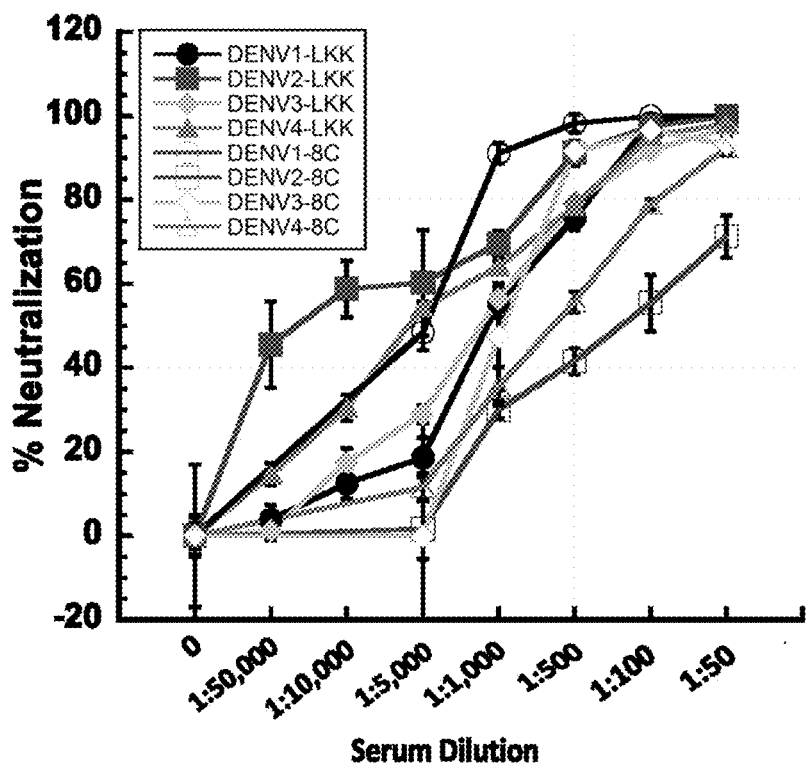
FIG. 14 is a graph showing antigen neutralizing activity. Focus-forming-unit reduction neutralization assays were performed by incubating DENV-1, -2, -3, and -4 with serial dilutions of sera from patients 8C and DA003 prior to infecting monolayers of LLC-MK2 cells. The pooled data points show the means of at least two independent experiments with three replicates each. The error bars indicate standard deviations.
Figure 15A:
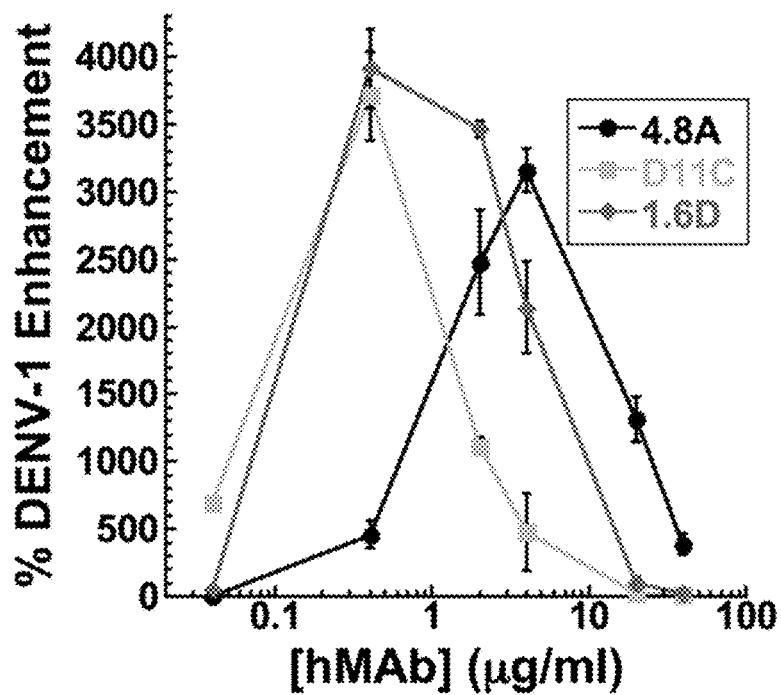
FIG. 15(a) through (d) shows the viral uptake results from enhancement assays performed in the presence of monoclonal antibodies from DENV infected patients. Enhanced infection of Fc receptor-bearing K562 cells was measured by DENV-specific qRT-PCR following infection with (a) DENV-1, (b) DENV-2, (c) DENV-3, and (d) DENV-4 in the presence of hMAbs 4.8A, D11C, and 1.6D. Each data point is the mean of three replicates. The error bars indicate standard deviations.
Figure 15B:
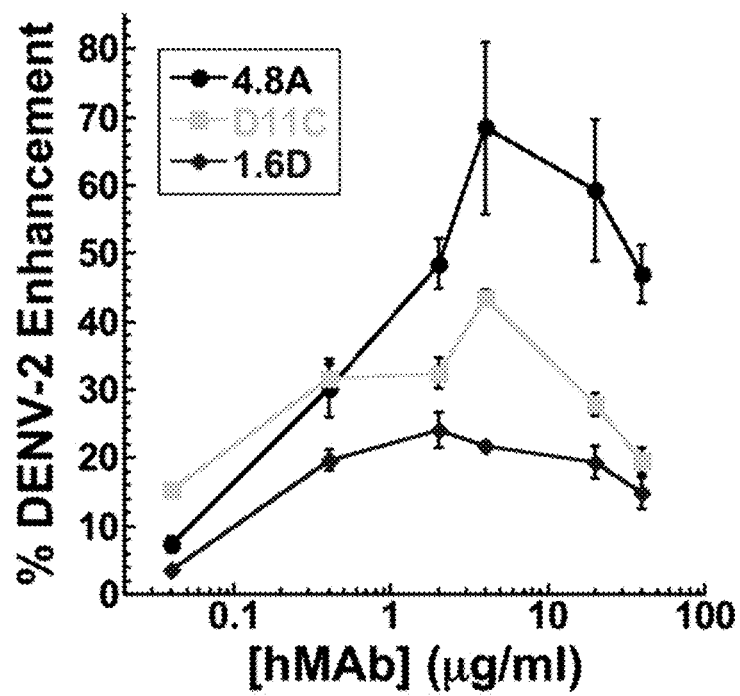
Figure 15C:
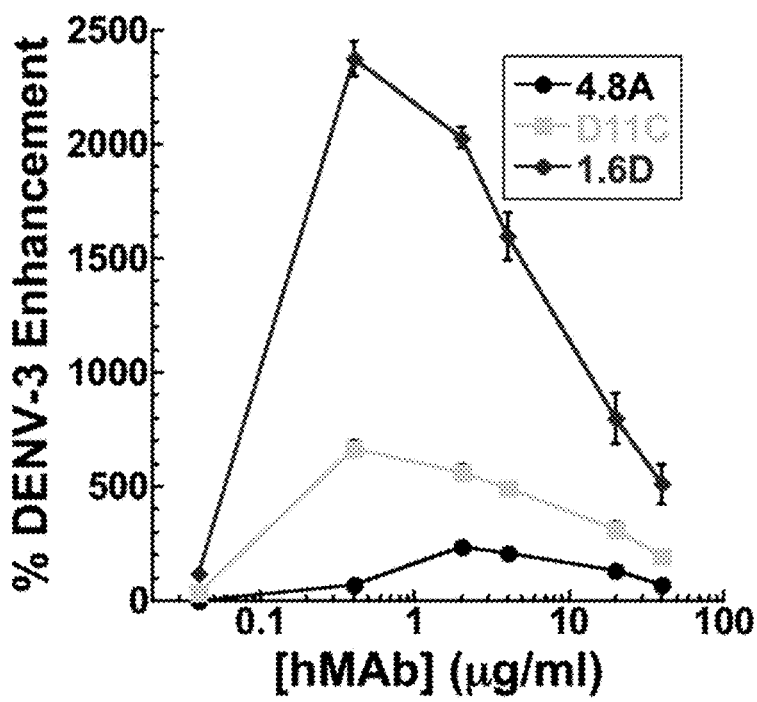
Figure 15D:
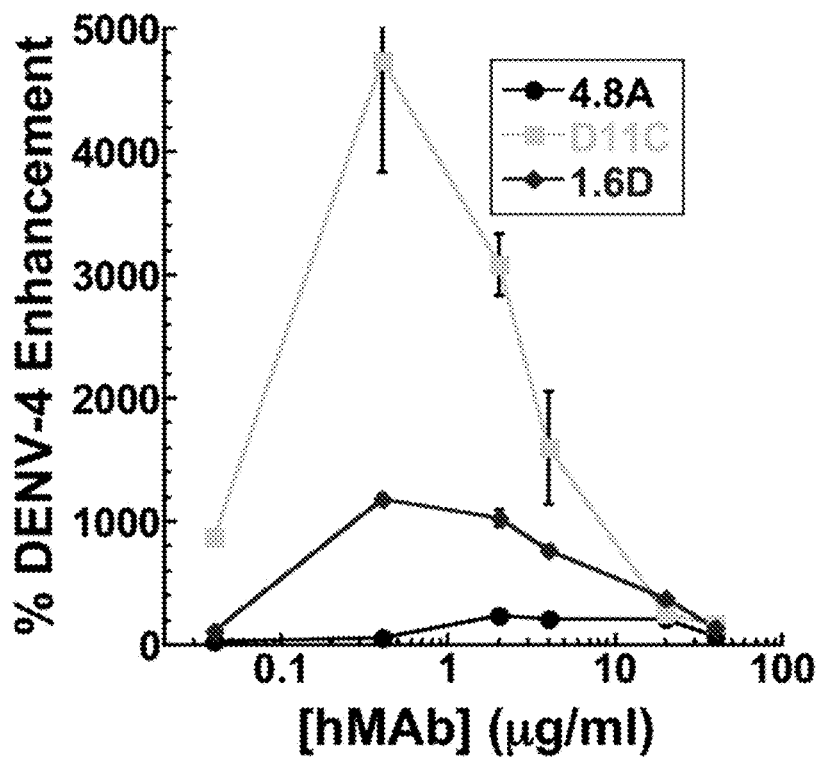
Figure 16:
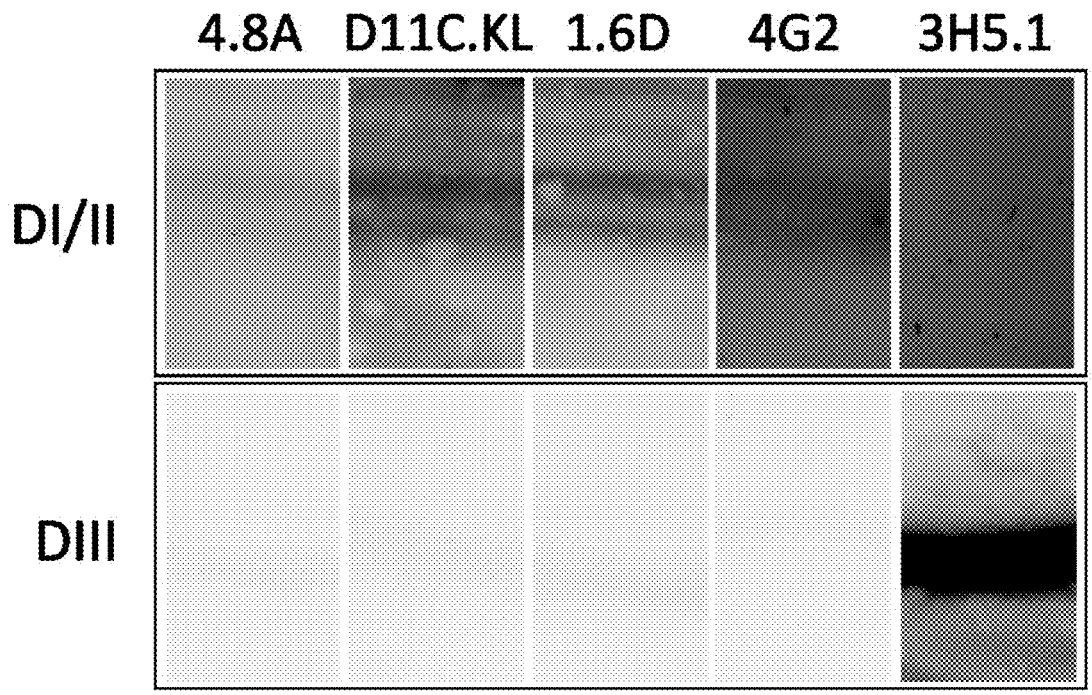
FIG. 16 is a blot showing coarse-level epitope mapping. Western blots were prepared with DENV-2 sDI/II and sDIII, and blot strips were probed with 5 µg/ml of hMAbs 4.8A, D11C, 1.6D, and control mMAbs 4G2 and 3H5.1 under nonreducing conditions. Binding of antibodies to sDI/II on the blot strips was detected at a PMT voltage of 475 V or 562 V for hMAbs and mMAbs, respectively, whereas binding of both hMAbs and mMAbs to sDIII on blot strips was detected at a PMT voltage of 420 V.

Sera from patients 8C and DA003 neutralized all four serotypes, as seen in FIG. 14. Serum from patient 7B was previously reported to strongly neutralize DENV-1 and -3 and weakly neutralize DENV-2 and -4 (Schieffelin, et al., Neutralizing and non-neutralizing monoclonal antibodies against dengue virus E protein derived from a naturally infected patient. Virol. J. 2010 Feb. 4; 7:28). To characterize the neutralizing activities of the hMAbs derived from the subjects, neutralization assays were performed with each hMAb, seen in FIGS. 11(a) through (c). All three hMAbs neutralized DENV-1 through -4 to some extent in a dose-dependent manner. Some of the hMAbs were stronger neutralizers than others, whereas some neutralized specific serotypes more strongly than others. For example, the IC$_{50}$s of hMAbs D11C and 1.6D were 1 µg/ml or below, as seen in FIGS. 11(b) and (c), whereas hMAb 4.8A did not reach 50% inhibition of infectivity against DENV-2 or DENV-4 over the hMAb concentrations tested, seen in FIG. 11(a). The observed neutralization activity of hMAb 4.8A was consistent with patient 7B serum activity (Schieffelin, et al., Neutralizing and non-neutralizing monoclonal antibodies against dengue virus E protein derived from a naturally infected patient. Virol. J. 2010 Feb. 4; 7:28). Additionally, D11C neutralized DENV-1, -2, and -4 more strongly than DENV-3, seen in FIG. 11(b). HMAb 1.6D neutralized DENV-1 through -4 with similar activity, as seen in FIG. 11(c).

To determine the neutralization potential of the hMAbs against other flaviviruses, neutralization assays using yellow fever virus (YF-17D) and YF-17D pseudotyped with West Nile virus E glycoprotein were performed, seen in FIGS. 11(a) through (c). The hMAbs neutralized WNV to some extent but did not appreciably neutralize yellow fever virus.

The DENV fusion loop is highly conserved, so it is not clear why hMAb 4.8A inhibited DENV-2 and -4 less strongly than DENV-1 and -3 nor why hMAb D11C inhibited DENV-3 less strongly. Additionally, other flaviviruses with nearly identical fusion loop sequences are not inhibited effectively, with hMAbs 4.8A, D11C, and 1.6D achieving only an intermediate level of neutralization against WNV and very poor neutralization against yellow fever virus. It is likely that the fusion loop region may be oriented differently or have altered accessibility in different viruses, (Dowd, et al., A dynamic landscape for antibody binding modulates antibody-mediated neutralization of West Nile virus. PLoS Pathog. 2011 June; 7(6):e1002111) necessitating the neutralizing antibodies to target amino acids adjacent to the fusion loop. These hMAbs bind to E under native conditions but do not bind denatured and reduced E protein, seen in FIG. 8(a), suggesting that disulfide bridges preserve a structural conformation of the epitopes. Additional nonconserved, fusion loop-adjacent residues may also contribute to antibody binding. Such residues could have a cumulative effect on binding energetics that is not detected when individual residues are mutated in isolation. These potential additional contact residues might be on the same E protein or part of an adjacent E protein on the virus surface. Binding to recombinant sE monomers and dissociated E protein in ELISAs and Western blots is not identical to binding the E proteins as they are arranged on the surface of a virion. E protein dimers are located in distinct symmetry positions on assembled viruses, and steric hindrance may alter the binding of antibodies to these positions, similar to observations with binding to WNV (Pierson, et al., The stoichiometry of antibody-mediated neutralization and enhancement of West Nile virus infection. Cell Host Microbe. 2007 Apr. 19; 1(2):135-45).

Example 6

At certain concentrations and with the proper Fc domain, all anti-DENV antibodies have the potential to mediate antibody-dependent enhancement in Fc receptor-bearing cells in vitro. For neutralizing antibodies, this enhancement effect decreases as the antibody concentration increases due to the antibody's ability to completely coat the virus and effectively neutralize it. However, for nonneutralizing antibodies, the enhancement potential remains high even at high antibody concentrations (Schieffelin, et al., Neutralizing and non-neutralizing monoclonal antibodies against dengue virus E protein derived from a naturally infected patient. Virol. J. 2010 Feb. 4; 7:28). To determine the antibody-dependent enhancement potential- through antibody-mediated cellular uprake of viral particles- of the three hMAbs, each of the four DENV serotypes were incubated with increasing concentrations of hMAbs 4.8A, D11C, and 1.6D and infected the Fc receptor II-bearing human macrophage-like cell line K562. Subsequent viral replication was measured by DENV-specific qRT-PCR. In the absence of antibodies that could serve to mediate DENV infection, K562 cells were more permissive to DENV-2 infection than to DENV-1, -3, and -4. As a result, normalized enhancements were typically lower for DENV-2 than for the other 3 serotypes. Each antibody displayed a similar general trend, as seen in FIGS. 15(a) through (d), with a peak enhancement of infection at antibody concentrations of 0.4 to 4 µg/ml, followed by neutralization, resulting in reduced infection at increasing antibody concentrations.

The DENV fusion loop is highly conserved, so it is not clear why hMAb 4.8A inhibited DENV-2 and -4 less strongly than DENV-1 and -3 nor why hMAb D11C inhibited DENV-3 less strongly. Additionally, other flaviviruses with nearly identical fusion loop sequences are not inhibited effectively, with hMAbs 4.8A, D11C, and 1.6D achieving only an intermediate level of neutralization against WNV and very poor neutralization against yellow fever virus. It is possible that the fusion loop region may be oriented differently or have altered accessibility in different viruses (Dowd, et al., A dynamic landscape for antibody binding modulates antibody-mediated neutralization of West Nile virus. PLoS Pathog. 2011 June; 7(6):e1002111). These hMAbs bind to E under native conditions but do not bind denatured and reduced E protein, as seen in FIGS. 8(a) and (b), suggesting that disulfide bridges preserve a structural conformation of the epitopes. Additional nonconserved, fusion loop-adjacent residues may also contribute to antibody binding. Such residues could have a cumulative effect on binding energetics that is not detected when individual residues are mutated in isolation. These potential additional contact residues might be on the same E protein or part of an adjacent E protein on the virus surface, as antibodies may extend across two E proteins found on a viral particle's surface. Binding to recombinant sE monomers and dissociated E protein in ELISAs and Western blots is not identical to binding the E proteins as they are arranged on the surface of a virion. E protein dimers are located in distinct symmetry positions on assembled viruses, and steric hindrance may alter the binding of antibodies to these positions, similar to observations with binding to WNV (Pierson, et al., The stoichiometry of antibody-mediated neutralization and enhancement of West Nile virus infection. Cell Host Microbe. 2007 Apr. 19; 1(2):135-45).

While the neutralization activities reported here are lower than those of some recently described hMAbs (Dejnirattisai, et al., Cross-reacting antibodies enhance dengue virus infection in humans. Science. 2010 May 7; 328(5979):745-8; Beltramello, et al., The human immune response to Dengue virus is dominated by highly cross-reactive antibodies endowed with neutralizing and enhancing activity. Cell Host Microbe. 2010 Sep. 16; 8(3):271-83; de Alwis, et al., In-depth analysis of the antibody response of individuals exposed to primary dengue virus infection. PLoS Negl. Trop. Dis. 2011 June; 5(6):e1188), it is difficult to compare neutralization potencies between assay systems in different laboratories, as the potency can vary depending on the specific assay used, the serotype and strain of virus, the target cell line, and the incubation conditions of the assay (Roehrig, et al., Guidelines for plaque-reduction neutralization testing of human antibodies to dengue viruses. Viral Immunol. 2008 June; 21(2):123-32; Thomas, et al., Dengue plaque reduction neutralization test (PRNT) in primary and secondary dengue virus infections: how alterations in assay conditions impact performance. Am. J. Trop. Med. Hyg. 2009 November; 81(5):825-33. doi: 10.4269/ajtmh.2009.08-0625). Despite difficulties comparing methodologies, neutralization potency alone offers an incomplete view of the human antibody response. Given this work, and the work of others, there appears to be a wide spectrum of hMAb responses directed against the DENV surface proteins, ranging from potently neutralizing, serotype-specific antibodies to nonneutralizing, cross-reactive antibodies, and many hMAbs falling between these two extremes (Schieffelin, et al., Neutralizing and non-neutralizing monoclonal antibodies against dengue virus E protein derived from a naturally infected patient. Virol. J. 2010 Feb. 4; 7:28; Dejnirattisai, et al., Cross-reacting antibodies enhance dengue virus infection in humans. Science. 2010 May 7; 328(5979):745-8; Beltramello, et al., The human immune response to Dengue virus is dominated by highly cross-reactive antibodies endowed with neutralizing and enhancing activity. Cell Host Microbe. 2010 Sep. 16; 8(3):271-83; de Alwis, et al., In-depth analysis of the antibody response of individuals exposed to primary dengue virus infection. PLoS Negl. Trop. Dis. 2011 June; 5(6):e1188; de Alwis, et al., Identification of human neutralizing antibodies that bind to complex epitopes on dengue virions. Proc. Natl. Acad. Sci. U.S.A. 2012 May 8; 109(19):7439-44). However, by targeting critical neutralizing epitopes located on endogensouly folded E proteins, namely those found adjacent to the fusion loop at 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of YFV, or corresponding amino acids of other flaviviruses, vaccines stimulate neutralizing antibodies.

Figure 17:
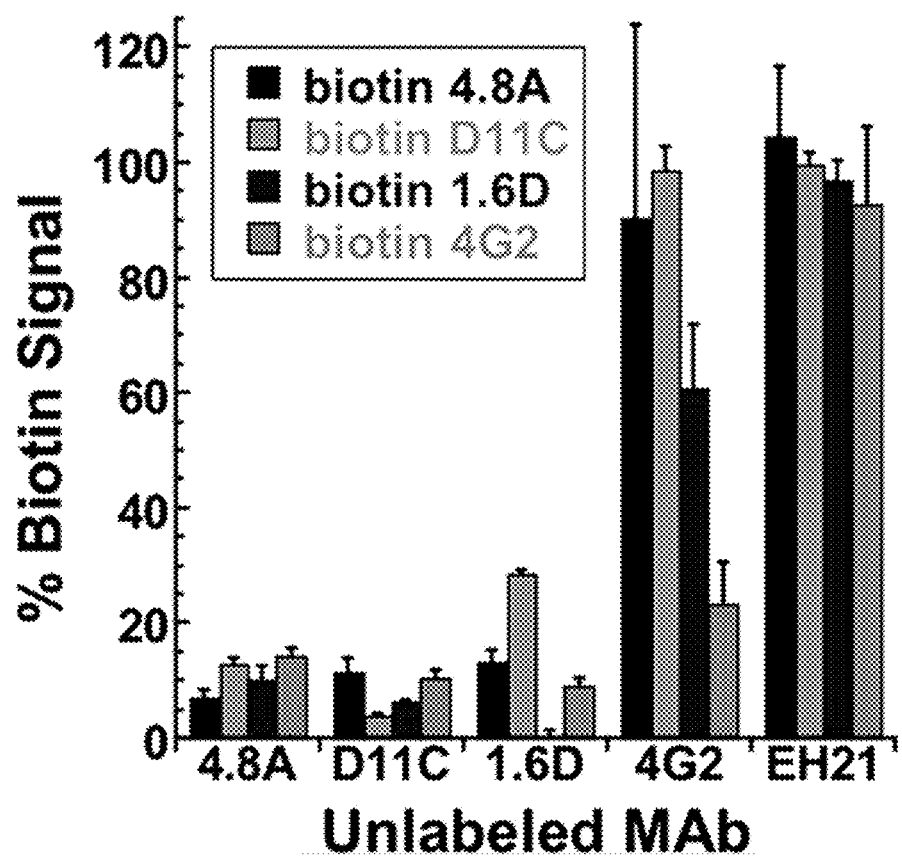
FIG. 17 is a graph showing competition ELISA, used to determine whether hMAbs 4.8A, D11C, and 1.6D and mMAb 4G2 recognized overlapping epitopes on DENV-1 E protein. HMAb EH21 against HIV-1 ENV was used as a negative control. Unlabeled antibodies (shown on the x axis) were added to DENV-1 E protein-coated wells. Upon removal of unbound antibodies, the wells were probed with biotinylated antibodies as shown.

Using vesicular stomatitis virus mMAbs, Bachmann et al. demonstrated that in vivo protection was independent of immunoglobulin subclass, avidity, and in vitro neutralization activity and that above a minimal avidity threshold ($>2\times10^7$ $M^{-1}$), protection depended simply on a minimum serum concentration (Bachmann, et al., The role of antibody concentration and avidity in antiviral protection. Science. 1997 Jun. 27; 276(5321):2024-7). For therapeutic or protective purposes, whether it would be preferable to have multiple serotype-specific, highly neutralizing anti-DENV hMAbs or a single cross-reactive and moderately neutralizing hMAb is currently unknown.

Example 7

To determine which E protein domain(s) hMAbs 4.8A, D11C, and 1.6D interacted with, recombinant DENV-2 E proteins sDI/II and sDIII were subjected to SDS-PAGE under nonreducing conditions and probed with equal amounts of hMAbs 4.8A, D11C, and 1.6D and control mMAbs 3H5.1 (specific for DENV-2 E DIII) or 4G2 (specific for DENV E DII fusion loop). hMAbs 4.8A, D11C, and 1.6D interacted specifically with sDI/II and not with sDIII, as seen in FIG. 16.

To determine whether hMAbs 4.8A, D11C, and 1.6D bound to overlapping epitopes on E protein, an ELISA binding competition assay were used, as previously reported (Schieffelin, et al., Neutralizing and non-neutralizing monoclonal antibodies against dengue virus E protein derived from a naturally infected patient. Virol. J. 2010 Feb. 4; 7:28). Unlabeled hMAbs 4.8A, D11C, 1.6D, and EH21 (an anti-HIV-1 gp120 antibody) and mMAb 4G2 (which binds to the DENV fusion loop) were incubated with DENV-1 antigen bound in ConA-coated plates. Biotinylated antibodies were then added to wells containing prebound unlabeled antibodies. If the labeled and unlabeled antibodies bound to the same epitope or overlapping epitopes, then the labeled antibody would not bind, resulting in a low signal upon development with streptavidin-conjugated enzyme. Biotinylated hMAbs 4.8A, D11C, and 1.6D were unable to bind to wells containing any of their unlabeled counterparts, as seen in FIG. 17. In addition, mMAb 4G2, which binds to the fusion loop, was unable to bind in the presence of hMAb 4.8A, D11C, or 1.6D. These results suggest that the three hMAbs and 4G2 share overlapping epitopes. Of note, when wells preincubated with unlabeled mMAb 4G2 were incubated with labeled hMAbs, the hMAbs were able to displace mMAb 4G2 to some extent. This result could suggest that the hMAbs and mMAb 4G2 bind to different epitopes. However, the results could also arise if hMAbs 4.8A, D11C, and 1.6D bind to the same E protein epitope as mMAb 4G2 but with higher affinities (as is further suggested by experiments described below). As a validation of the competition assay, the negative-control hMAb EH21 did not compete for binding with either the hMAbs or mMAb 4G2.

Figure 18:
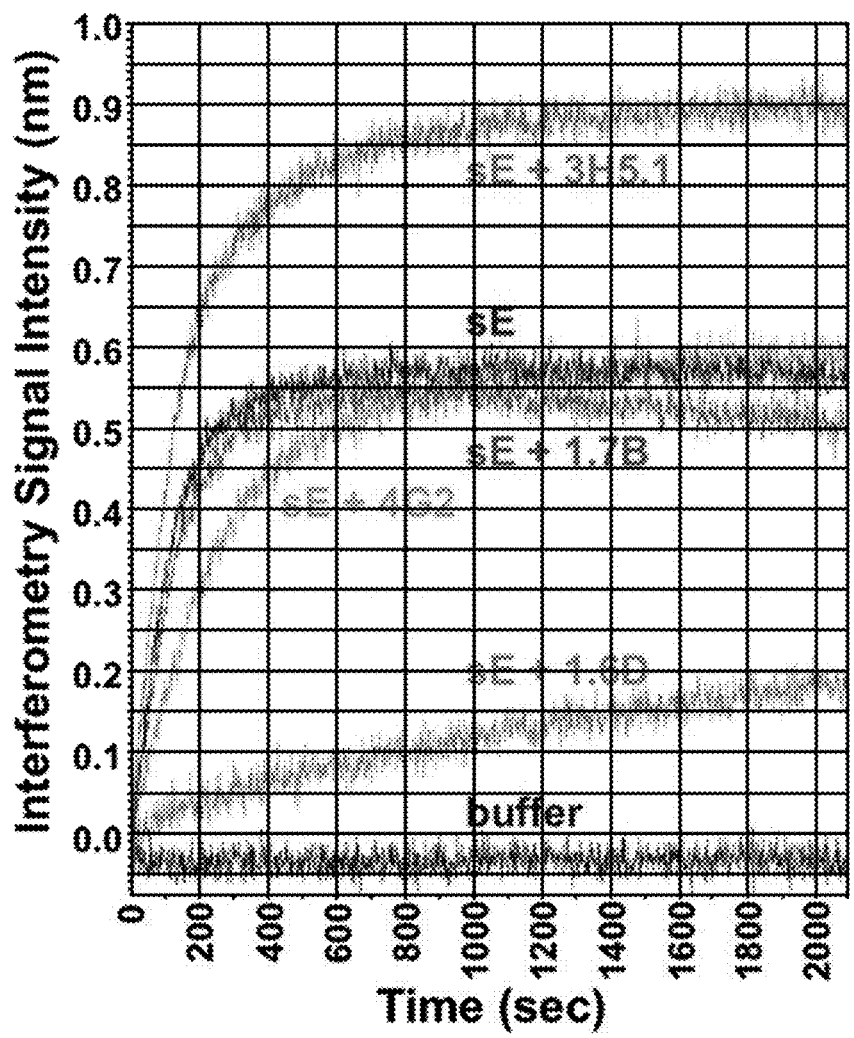
FIG. 18 is a graph showing antibody binding competition was measured using biolayer interferometry. Biosensor probes were coupled to hMAb 1.6D and subsequently incubated with either DENV-2 sE alone or sE complexed with hMAb 1.6D or control anti-HIV 1.7B or with mMAb 4G2 or 3H5.1.

To further investigate the relative binding affinities of hMAbs to their epitopes, hMAb 1.6D were chosen for additional studies in an antibody binding competition biolayer interferometry assay. hMAb 1.6D was coupled to human IgG binding sensors. After removing unbound hMAb 1.6D, DENV-2 sE that had been preincubated at a 1:1 molar ratio was applied with hMAb 1.6D, mMAb 4G2 or 3H5.1, or medium only to the sensors. As before, binding of the sE protein to the hMAbs on the surfaces of the probes was measured by the change in interference from light reflected from the surface of the probe. The magnitude of the signal was indicative of the thickness of the antibody-sE complexes. It was anticipated that if an antibody effectively competed for binding to the hMAb 1.6D epitope, sE precomplexed with that particular antibody would not be able to bind to the hMAb 1.6D-coated sensor. In contrast, if a particular antibody bound to a different epitope on sE, the sE-antibody complex would be able to bind to the hMAb 1.6D-coated sensor. As expected, DENV-2 sE bound to the hMAb 1.6D-coated sensor, generating a signal proportional to the thickness of the antibody on the sensor plus the sE protein, as seen in FIG. 18. When sE was precomplexed with hMAb 1.6D prior to addition (sE plus 1.6D), sE binding to hMAb 1.6D captured on the sensor was profoundly reduced, indicating that hMAb 1.6D can compete very effectively with itself for binding. When mMAb 3H5.1, which binds to DIII, was precomplexed with sE, the sE-3H5.1 complex bound to the hMAb 1.6D-coated sensor, resulting in an increased signal due to the increased thickness of the probe-coupled complex, which consisted of sE plus two antibodies. As a control, when an irrelevant anti-HIV hMAb (1.7B) was added to sE, the binding signal was equivalent to that of sE alone. When mMAb 4G2 was precomplexed with sE, sE bound to the hMAb 1.6D-coated sensor; however, the thickness of the complex was indicative of only sE binding to the sensor with no additional antibody. This result is likely due to effective competition of hMAb 1.6D with the mMAb 4G2 binding epitope, consistent with competition by ELISA, seen in FIG. 17. The antibody binding competition biolayer interferometry assay further established that hMAbs bound to epitopes on the E protein fusion loop and suggested that these hMAbs may have higher affinities than similar mMAbs.

Figure 19:
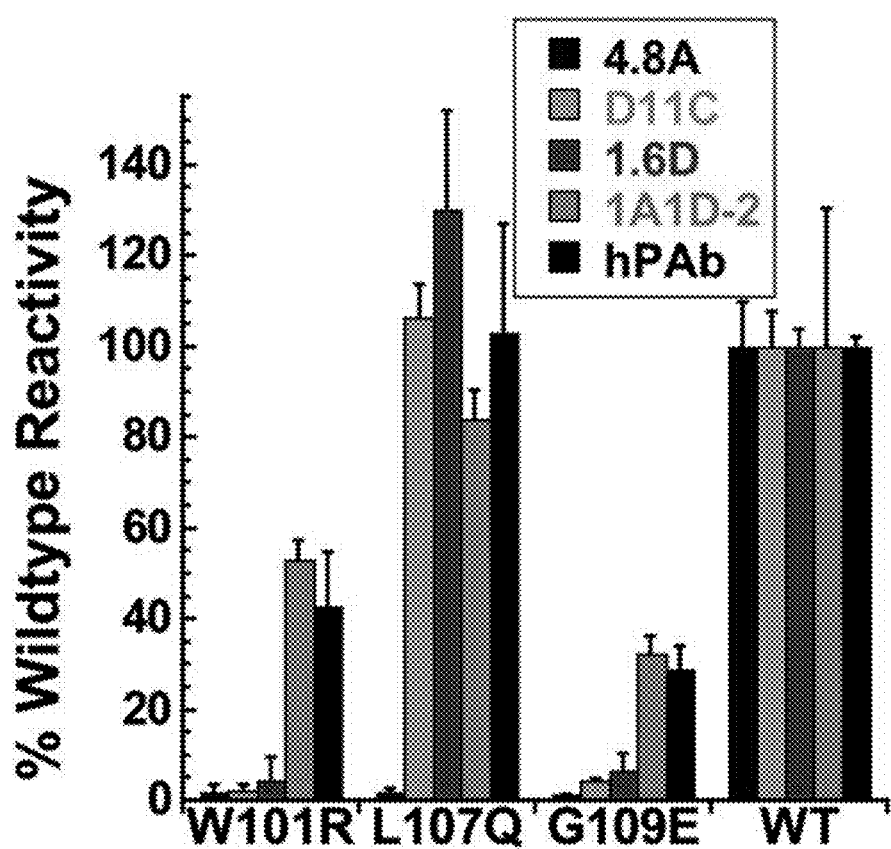
FIG. 19 is a graph showing molecular-level epitope mapping. Cells expressing DENV E mutants were fixed and immunostained with the indicated antibodies. Clones with reactivities of <25% relative to wild-type (WT) DENV-3 E were identified as critical for hMAb binding. The reactivities of mutant clones containing each critical residue with hMAbs 4.8A, D11C, and 1.6D and the control mMAb 1A1D-2 and human polyclonal serum (hPAb) are shown. The experiments were repeated three times, and standard deviations of quadruplicate wells are shown.

To more precisely define the epitopes for hMAbs 4.8A, D11C, and 1.6D, a library of DENV-3 E point mutants was screened to identify mutations that reduce hMAb binding. Three residues, W101, L107, and G109, that when mutated significantly reduced 4.8A, D11C, or 1.6D binding compared to wild-type E protein were identified, as seen in FIG. 19. Illustrations of the crystal protein structure of the DENV envelope protein outline the E protein fusion loop 10, surrounded by adjacent AA domain 12, located within 5 Å of fusion loop of DENV-3 E protein. These residues were located directly within the fusion loop (residues 98 to 109) and mapped in close proximity on the structure of the E protein, seen in FIG. 1(a). As seen in the images, the adjacent AA domain 12 is surrounded distally from the center of the glycoprotein by DENV-3 E protein DI motif 14 and DENV-3 E protein DIII motif 15, and proximally to the center of the glycoprotein by DENV-3 E protein DII motif 20, as seen in FIGS. 1(a) and (b).

Each E protein mutant reacted to a human polyclonal serum and the conformation-dependent mMAb 1A1D-2 that targets a different epitope (Lok, et al., Binding of a neutralizing antibody to dengue virus alters the arrangement of surface glycoproteins. Nat. Struct. Mol. Biol. 2008 March; 15(3):312-7), confirming that each clone was expressed and was not simply globally misfolded. hMAb 4.8A binding was reduced by mutations at any of the three positions, while D11C and 1.6D binding was reduced by mutations at only W101 or G109. These data suggest that 4.8A, D11C, and 1.6D have overlapping but distinct epitopes in the fusion loop, consistent with their ability to compete with each other and with a fusion loop mMAb.

This study focused on the portion of the human antibody response that is broadly neutralizing and potentially protective against all DENV serotypes. Several other classes of DENV-neutralizing hMAbs are primarily serotype specific, including hMAbs that target E protein DIII (Dejnirattisai, et al., Cross-reacting antibodies enhance dengue virus infection in humans. Science. 2010 May 7; 328(5979):745-8; Beltramello, et al., The human immune response to Dengue virus is dominated by highly cross-reactive antibodies endowed with neutralizing and enhancing activity. Cell Host Microbe. 2010 Sep. 16; 8(3):271-83; de Alwis, et al., In-depth analysis of the antibody response of individuals exposed to primary dengue virus infection. PLoS Negl. Trop. Dis. 2011 June; 5(6):e1188) and hMAbs that recognize quaternary epitopes between two E proteins (de Alwis, et al., Identification of human neutralizing antibodies that bind to complex epitopes on dengue virions. Proc. Natl. Acad. Sci. U.S.A. 2012 May 8; 109(19):7439-44; Teoh, et al., The structural basis for serotype-specific neutralization of dengue virus by a human antibody. Sci. Transl. Med. 4 2012 Jun. 20; 4(139):139ra83). The mechanism of action of broadly neutralizing antibodies produced in three human dengue patients was established. Though the hMAbs were isolated from patients from different countries and diverse ethnic backgrounds, with different infecting viruses, and at different times postrecovery, similar broadly neutralizing hMAbs were produced, suggesting that the target of these hMAbs is a common epitope that plays an important role in DENV infectivity. With the goal of determining the mechanism of neutralization, using a novel assay, DENV binding was uncoupled to target cells from fusion and found that the neutralization activity of the hMAbs correlated with inhibition of fusion rather than virus-cell binding. The binding of the hMAbs to the highly conserved fusion loop region in DII of the E glycoprotein was then mapped.

With the goal of determining the mechanism of neutralization, using a novel assay, DENV binding to target cells was uncoupled from fusion. It was discovered that the neutralization activity of the hMAbs correlated with inhibition of fusion rather than virus-cell binding.

Immunological studies have shown that responses to dengue infection results in antibody activity that is substantially stronger for E protein than for other flavivirus proteins (Lai, et al., Antibodies to envelope glycoprotein of dengue virus during the natural course of infection are predominantly cross-reactive and recognize epitopes containing highly conserved residues at the fusion loop of domain II. J. Virol. 2008 July; 82(13):6631-43). E proteins are arranged anti-parallel in a herringbone isosahedral-like structure, which has been attributed to difficulties in using the E protein as a vaccine target due to different epitope presentations on the viral surface (Dowd, et al., A dynamic landscape for antibody binding modulates antibody-mediated neutralization of West Nile virus. PLoS Pathog. 2011 June; 7(6):e1002111). However, flaviviruses exist in a dynamic state, fluctuating between different exterior conformations as particles move on the viral particle, a state called "breathing" (Dowd, et al., A dynamic landscape for antibody binding modulates antibody-mediated neutralization of West Nile virus. PLoS Pathog. 2011 June; 7(6):e1002111). With all the complexities of flaviviruses, as well as complexities of the E protein, most neutralizing antibodies for flaviviruses have been found directed to the E protein, at all 3 domains (Dowd, et al., A dynamic landscape for antibody binding modulates antibody-mediated neutralization of West Nile virus. PLoS Pathog. 2011 June; 7(6):e1002111), and of these, most cross-reactive antibodies were found directed toward the fusion loop and were typically non-neutralizing in dengue-infected patients (Lai, et al., Antibodies to envelope glycoprotein of dengue virus during the natural course of infection are predominantly cross-reactive and recognize epitopes containing highly conserved residues at the fusion loop of domain II. J. Virol. 2008 July; 82(13):6631-43). E domain II is responsible for flavivirus group and serotype cross reactive epitopes (Lai, et al., Antibodies to envelope glycoprotein of dengue virus during the natural course of infection are predominantly cross-reactive and recognize epitopes containing highly conserved residues at the fusion loop of domain II. J. Virol. 2008 July; 82(13):6631-43) whereas studies of neutralizing epitopes show a preference for targeting E proteins domain III (Lin, et al., Analysis of epitopes on dengue virus envelope protein recognized by monoclonal antibodies and polyclonal human sera by a high throughput assay. PLoS Negl. Trop. Dis. 2012 January; 6(1):e1447), but that such neutralizing activities are typically serotype-specific (Wahala, et al., Dengue virus neutralization by human immune sera: role of envelope protein domain III-reactive antibody. Virology. 2009 Sep. 15; 392(1):103-13). For neutralization, virions must be bound by multiple antibodies to reach a neutralizing threshold, typically around 30 antibodies per virial particle, and is controlled by antibody avidity toward the epitope and steric constraints at accessing the epitope. (Dowd, et al., A dynamic landscape for antibody binding modulates antibody-mediated neutralization of West Nile virus. PLoS Pathog. 2011 June; 7(6):e1002111). Further, neutralization was found to be time- and temperature-dependent, and occurs more rapidly in dengue virus than some other flaviviruses, like West Nile Virus. (Dowd, et al., A dynamic landscape for antibody binding modulates antibody-mediated neutralization of West Nile virus. PLoS Pathog. 2011 June; 7(6):e1002111). Epitopes found on domain II, but outside the fusion loop, show less specificity to changes (Lai, et al., Antibodies to envelope glycoprotein of dengue virus during the natural course of infection are predominantly cross-reactive and recognize epitopes containing highly conserved residues at the fusion loop of domain II. J. Virol. 2008 July; 82(13):6631-43). Accordingly, vaccines targeting areas adjacent to the fusion loop permit access to serotype-conserved E protein regions, that are not sterically hindered.

A common theme among different structural classes of enveloped virus fusion proteins is the existence of an internal or N-terminal hydrophobic fusion loop or fusion peptide. Neutralizing antibodies directed against these fusion regions have been well described in other virus systems, including closely related flaviviruses (Cherrier, et al., Structural basis for the preferential recognition of immature flaviviruses by a fusion-loop antibody. EMBO J. 2009 Oct. 21; 28(20):3269-76), more distantly related alphaviruses (Hammar, et al., Prefusion rearrangements resulting in fusion peptide exposure in Semliki forest virus. J. Biol. Chem. 2003 Feb. 28; 278(9):7189-98), and unrelated orthomyxoviruses (Hashem, et al., Universal antibodies against the highly conserved influenza fusion peptide cross-neutralize several subtypes of influenza A virus. Biochem. Biophys. Res. Commun. 2010 Dec. 10; 403(2):247-51). The results are consistent with those of a recent study that identified two other broadly neutralizing hMAbs from a single patient that target DENV DI/II and whose binding to WNV DI/II was ablated when residues in the fusion loop were altered, suggesting that these antibodies may also bind to the DENV fusion loop (Beltramello, et al., The human immune response to Dengue virus is dominated by highly cross-reactive antibodies endowed with neutralizing and enhancing activity. Cell Host Microbe. 2010 Sep. 16; 8(3):271-83). Importantly, reports focusing on polyclonal antibody fractions from DENV patient-derived serum have shown that the predominant fraction of the broadly neutralizing activity targets DI/II and specifically the fusion loop, consistent with the hMAb results (Lai, et al., Antibodies to envelope glycoprotein of dengue virus during the natural course of infection are predominantly cross-reactive and recognize epitopes containing highly conserved residues at the fusion loop of domain II. J. Virol. 2008 July; 82(13):6631-43; Lin, et al., Analysis of epitopes on dengue virus envelope protein recognized by monoclonal antibodies and polyclonal human sera by a high throughput assay. PLoS Negl. Trop. Dis. 2012 January; 6(1):e1447; Wahala, et al., Dengue virus neutralization by human immune sera: role of envelope protein domain III-reactive antibody. Virology. 2009 Sep. 15; 392(1):103-13). Broadly neutralizing chimpanzee MAbs and mMAbs targeting the DENV fusion loop have been described previously (Gentry, et al., Identification of distinct antigenic determinants on dengue-2 virus using monoclonal antibodies. Am. J. Trop. Med. Hyg. 1982 May; 31(3 Pt 1):548-55; Henchal, et al., Epitopic analysis of antigenic determinants on the surface of dengue-2 virions using monoclonal antibodies. Am. J. Trop. Med. Hyg. 1985 January; 34(1):162-9; Goncalvez, et al., Monoclonal antibody-mediated enhancement of dengue virus infection in vitro and in vivo and strategies for prevention. Proc. Natl. Acad. Sci. U.S.A. 2007 May 29; 104(22):9422-7).

The finding that hMAbs recognizing the fusion loop inhibit the fusion stage of DENV entry into mammalian cells is consistent with earlier reports that a chimpanzee MAb against the fusion loop inhibits fusion between mosquito cells mediated by cell surface-bound dengue virions (Goncalvez, et al., Epitope determinants of a chimpanzee Fab antibody that efficiently cross-neutralizes dengue type 1 and type 2 viruses map to inside and in close proximity to fusion loop of the dengue type 2 virus envelope glycoprotein. J. Virol. 2004 December; 78(23):12919-28). The hMAbs reported here can individually block the binding of an mMAb recognizing the fusion loop, confirming that they share overlapping epitopes. However, mMAb prebound to E could not block binding by the hMAbs, indicating that the particular mMAb used either has a lower affinity than the hMAbs or that hMAbs bind to the fusion loop differently, in a manner that allows the hMAbs to displace the mMAb.

The DENV fusion loop is highly conserved, so it is not clear why hMAb 4.8A inhibited DENV-2 and -4 less strongly than DENV-1 and -3 nor why hMAb D11C inhibited DENV-3 less strongly. Additionally, other flaviviruses with nearly identical fusion loop sequences are not inhibited effectively, with hMAbs 4.8A, D11C, and 1.6D achieving only an intermediate level of neutralization against WNV and very poor neutralization against yellow fever virus. It is possible that the fusion loop region may be oriented differently or have altered accessibility in different viruses (Dowd, et al., A dynamic landscape for antibody binding modulates antibody-mediated neutralization of West Nile virus. PLoS Pathog. 2011 June; 7(6):e1002111). These hMAbs bind to E under native conditions but do not bind denatured and reduced E protein, as seen in FIG. 8(a), suggesting that disulfide bridges preserve a structural conformation of the epitopes. Additional nonconserved, fusion loop-adjacent residues may also contribute to antibody binding. Such residues could have a cumulative effect on binding energetics that is not detected when individual residues are mutated in isolation. These potential additional contact residues might be on the same E protein or part of an adjacent E protein on the virus surface. Binding to recombinant sE monomers and dissociated E protein in ELISAs and Western blots is not identical to binding the E proteins as they are arranged on the surface of a virion. E protein dimers are located in distinct symmetry positions on assembled viruses, and steric hindrance may alter the binding of antibodies to these positions, similar to observations with binding to WNV (Pierson, et al., The stoichiometry of antibody-mediated neutralization and enhancement of West Nile virus infection. Cell Host Microbe. 2007 Apr. 19; 1(2):135-45).

However, the use of amino acids adjacent to the fusion loop permits antibodies that target the DENV viral particles. Further, it is assumed highly neutralizing antibodies that tightly bind the viral epitope with outcompete any lesser neutralizing antibodies.

Both antibody-virus binding (Dowd, et al., A dynamic landscape for antibody binding modulates antibody-mediated neutralization of West Nile virus. PLoS Pathog. 2011 June; 7(6):e1002111) and virus-cell binding (Zaitseva, et al., Dengue virus ensures its fusion in late endosomes using compartment-specific lipids. PLoS Pathog. 2010 Oct. 7; 6(10):e1001131) can be ineffective at 4° C., the temperature that is often used in binding assays (van der Schaar, et al., Characterization of the early events in dengue virus cell entry by biochemical assays and single-virus tracking. J. Virol. 2007 November; 81(21):12019-28; Thaisomboonsuk, et al., Characterization of dengue-2 virus binding to surfaces of mammalian and insect cells. Am. J. Trop. Med. Hyg. 2005 April; 72(4):375-83). Thus, while the virus-cell binding assay based on measuring DiD fluorescence can be used to quantify binding at different temperatures, the efficiency of virus binding was measured at physiological temperature. Note that, like other virus-cell binding assays (Thaisomboonsuk, et al., Characterization of dengue-2 virus binding to surfaces of mammalian and insect cells. Am. J. Trop. Med. Hyg. 2005 April; 72(4):375-83; Watterson, et al., Residues in domain III of the dengue virus envelope glycoprotein involved in cell-surface glycosaminoglycan binding. J. Gen. Virol. 2012 January; 93(Pt 1):72-82), the assay does not distinguish between potential nonproductive, nonspecific binding to the cell surface and specific, productive binding between virions and a yet unidentified specific cell surface receptor for DENV, the identity of which is under debate (see, Hidari K I, Suzuki T. 2011. Dengue virus receptor. Trop. Med. Health. 2011 December; 39(4 Suppl): 37-43). The hMAbs were tested to determine if the antibodies might neutralize virus by inhibiting specific virus-receptor binding. It was estimated that to be undetectable within the margin of error of the data, any putative specific binding would represent only a small fraction of total binding. Additionally, the hMAbs would need to inhibit only this specific binding and not the nonspecific binding, and only this specific binding would allow productive viral entry and infection. While the possibility that the hMAbs block viral entry and infection by blocking unknown specific virus-receptor binding yet causing no changes in total virus-cell binding cannot be excluded, the conclusion that hMAbs block entry at the fusion stage rather than at the virus-cell binding stage is the most likely interpretation of the data. The liposome fusion assay results also support this conclusion.

Broadly neutralizing hMAbs can potentially be used in the development of therapeutic treatments. Most previous work in this area has focused on the use of mMAbs (Sukupolvi-Petty, et al., Structure and function analysis of therapeutic monoclonal antibodies against dengue virus type 2. J. Virol. 2010 September; 84(18):9227-39). The present study has shown that, for binding to E, an anti-DENV hMAb can outcompete an mMAb with a similar epitope. This observation is not surprising, since human antibodies tend to have longer variable regions than mouse antibodies (Johnson, et al., Preferred CDRH3 lengths for antibodies with defined specificities. Int. Immunol. 1998 December; 10(12): 1801-5; Schroeder, Similarity and divergence in the development and expression of the mouse and human antibody repertoires. Dev. Comp. Immunol. 2006; 30(1-2):119-35). When used therapeutically in patients, hMAbs are also much less likely to provoke an immune response, which can even be directed against the antigenically distinct variable regions in humanized mMAbs, where the heavy- and light-chain constant regions have been replaced with human sequences (Hwang, et al., Immunogenicity of engineered antibodies. Methods. 2005 May; 36(1):3-10). A recent study using a mouse model of lethal DENV infection showed that hMAbs protected mice after exposure to DENV, highlighting the important role that hMAbs can play in the development of DENV therapeutics (Beltramello, et al., The human immune response to Dengue virus is dominated by highly cross-reactive antibodies endowed with neutralizing and enhancing activity. Cell Host Microbe. 2010 Sep. 16; 8(3):271-83).

While the neutralization activities reported here are lower than those of some recently described hMAbs (Dejnirattisai, et al., Cross-reacting antibodies enhance dengue virus infection in humans. Science. 2010 May 7; 328(5979):745-8; Beltramello, et al., The human immune response to Dengue virus is dominated by highly cross-reactive antibodies endowed with neutralizing and enhancing activity. Cell Host Microbe. 2010 Sep. 16; 8(3):271-83; de Alwis, et al., In-depth analysis of the antibody response of individuals exposed to primary dengue virus infection. PLoS Negl. Trop. Dis. 2011 June; 5(6):e1188), it is difficult to compare neutralization potencies between assay systems in different laboratories, as the potency can vary depending on the specific assay used, the serotype and strain of virus, the target cell line, and the incubation conditions of the assay (Roehrig, et al., Guidelines for plaque-reduction neutralization testing of human antibodies to dengue viruses. Viral Immunol. 2008 June; 21(2):123-32; Thomas, et al., Dengue plaque reduction neutralization test (PRNT) in primary and secondary dengue virus infections: how alterations in assay conditions impact performance. Am. J. Trop. Med. Hyg. 2009 November; 81(5):825-33).

Despite difficulties comparing methodologies, neutralization potency alone offers an incomplete view of the human antibody response. Given this work, and the work of others, there appears to be a wide spectrum of hMAb responses directed against the DENV surface proteins, ranging from potently neutralizing, serotype-specific antibodies to non-neutralizing, cross-reactive antibodies, and many hMAbs falling between these two extremes (Schieffelin, et al., Neutralizing and non-neutralizing monoclonal antibodies against dengue virus E protein derived from a naturally infected patient. Virol. J. 2010 Feb. 4; 7:28; Dejnirattisai, et al., Cross-reacting antibodies enhance dengue virus infection in humans. Science. 2010 May 7; 328(5979):745-8; Beltramello, et al., The human immune response to Dengue virus is dominated by highly cross-reactive antibodies endowed with neutralizing and enhancing activity. Cell Host Microbe. 2010 Sep. 16; 8(3):271-83; de Alwis, et al., In-depth analysis of the antibody response of individuals exposed to primary dengue virus infection. PLoS Negl. Trop. Dis. 2011 June; 5(6):e1188; de Alwis, et al., Identification of human neutralizing antibodies that bind to complex epitopes on dengue virions. Proc. Natl. Acad. Sci. U.S.A. 2012 May 8; 109(19):7439-44). Using vesicular stomatitis virus mMAbs, Bachmann et al. demonstrated that in vivo protection was independent of immunoglobulin subclass, avidity, and in vitro neutralization activity and that above a minimal avidity threshold ($>2\times10^7$ $M^{-1}$), protection depended simply on a minimum serum concentration (Bachmann, et al., The role of antibody concentration and avidity in antiviral protection. Science. 1997 Jun. 27; 276(5321): 2024-7). For therapeutic or protective purposes, whether it would be preferable to have multiple serotype-specific, highly neutralizing anti-DENV hMAbs or a single cross-reactive and moderately neutralizing hMAb is currently unknown. However, the approach herein shows a single, multiple-serotype neutralizing antibody is generated from dengue viral vaccines directed toward the fusion loop, and targeting amino acids located adjacent to the fusion loop. The work does note that it is possible to generate multiple vaccines, each directed to a serotype, and such work can be performed by one of skill in the art utilizing this disclosure.

The extent to which the virus preparations used for the neutralization assays contain mature, immature, or partially mature particles has not characterized. Thus, it is unknown if hMAbs 4.8A, D11C, and 1.6D neutralize infectivity by preferentially binding to completely mature, partially mature, or completely immature virions. A previous study suggested a structural basis for the preferential binding of fusion loop antibodies to the partially exposed fusion loop region on immature flaviviruses (Cherrier, et al., Structural basis for the preferential recognition of immature flaviviruses by a fusion-loop antibody. EMBO J. 2009 Oct. 21; 28(20):3269-76), but differences between the mMAb used in that study, which bound to the be loop in addition to the fusion loop, and the hMAbs make it difficult to speculate on the role of mature versus immature virion structure in the results.

One of the most striking outcomes of other recent studies of hMAbs against DENV is the discovery that the response is dominated by broadly reactive but nonneutralizing antibodies directed against prM and E that serve only to enhance DENV infection in macrophages and other Fc receptor-bearing cells (Schieffelin, et al., Neutralizing and non-neutralizing monoclonal antibodies against dengue virus E protein derived from a naturally infected patient. Virol. J. 2010 Feb. 4; 7:28; Dejnirattisai, et al., Cross-reacting antibodies enhance dengue virus infection in humans. Science. 2010 May 7; 328(5979):745-8; Beltramello, et al., The human immune response to Dengue virus is dominated by highly cross-reactive antibodies endowed with neutralizing and enhancing activity. Cell Host Microbe. 2010 Sep. 16; 8(3):271-83; de Alwis, et al., In-depth analysis of the antibody response of individuals exposed to primary dengue virus infection. PLoS Negl. Trop. Dis. 2011 June; 5(6): e1188). The majority, if not all, of DENV vaccine candidates approaching or in clinical trials contain full-length DENV prM and E proteins (Beckett, et al., Evaluation of a prototype dengue-1 DNA vaccine in a phase 1 clinical trial. Vaccine. 2011 Jan. 29; 29(5):960-8; Durbin, et al., Dengue vaccine candidates in development. Curr. Topics Microbiol. Immunol. 2010; 338:129-43; Guirakhoo, et al., Live attenuated chimeric yellow fever dengue type 2 (ChimeriVax-DEN2) vaccine: phase I clinical trial for safety and immunogenicity: effect of yellow fever pre-immunity in induction of cross neutralizing antibody responses to all 4 dengue serotypes. Hum. Vaccin. 2006 March-April; 2(2):60-7; Guy, et al., Development of Sanofi Pasteur tetravalent dengue vaccine. Hum. Vaccin. 2010 Sep. 16; 6(9)).

Full-length DENV prM and E proteins, whether expressed as part of an attenuated DENV strain or expressed in another manner, may induce a broadly reactive and primarily nonneutralizing antibody response. Although both neutralizing and nonneutralizing antibodies can enhance infection, large numbers of broadly reactive nonneutralizing antibodies could shift the response in favor of enhancement, which may result in an increased risk of severe disease in vaccine recipients. However, if immunogens that present the fusion loop in the proper context can be developed, a broadly reactive neutralizing response might be possible for a DENV vaccine. The enhancing activity induced by such an immunogen might be reduced compared to full-length prM and E.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of an odor-neutralizing sheath, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

SEQUENCE LISTING

<160> NUMBER OF SEQ ID NOS: 5

<210> SEQ ID NO 1
<211> LENGTH: 493
<212> TYPE: PRT
<213> ORGANISM: Flavivirus yellow fever virus

<400> SEQUENCE: 1

```
Ala His Cys Ile Gly Ile Thr Asp Arg Asp Phe Ile Glu Gly Val His
1               5                   10                  15

Gly Gly Thr Trp Val Ser Ala Thr Leu Glu Gln Asp Lys Cys Val Thr
            20                  25                  30

Val Met Ala Pro Asp Lys Pro Ser Leu Asp Ile Ser Leu Glu Thr Val
        35                  40                  45

Ala Ile Asp Arg Pro Ala Glu Val Arg Lys Val Cys Tyr Asn Ala Val
    50                  55                  60

Leu Thr His Val Lys Ile Asn Asp Lys Cys Pro Ser Thr Gly Glu Ala
65                  70                  75                  80

His Leu Ala Glu Glu Asn Glu Gly Asp Asn Ala Cys Lys Arg Thr Tyr
                85                  90                  95

Ser Asp Arg Gly Trp Gly Asn Gly Cys Gly Leu Phe Gly Lys Gly Ser
            100                 105                 110

Ile Val Ala Cys Ala Lys Phe Thr Cys Ala Lys Ser Met Ser Leu Phe
        115                 120                 125

Glu Val Asp Gln Thr Lys Ile Gln Tyr Val Ile Arg Ala Gln Leu His
    130                 135                 140

Val Gly Ala Lys Gln Glu Asn Trp Asn Thr Asp Ile Lys Thr Leu Lys
145                 150                 155                 160

Phe Asp Ala Leu Ser Gly Ser Gln Glu Val Glu Phe Ile Gly Tyr Gly
                165                 170                 175

Lys Ala Thr Leu Glu Cys Gln Val Gln Thr Ala Val Asp Phe Gly Asn
            180                 185                 190

Ser Tyr Ile Ala Glu Met Glu Thr Glu Ser Trp Ile Val Asp Arg Gln
        195                 200                 205

Trp Ala Gln Asp Leu Thr Leu Pro Trp Gln Ser Gly Ser Gly Gly Val
    210                 215                 220

Trp Arg Glu Met His His Leu Val Glu Phe Glu Pro Pro His Ala Ala
225                 230                 235                 240

Thr Ile Arg Val Leu Ala Leu Gly Asn Gln Glu Gly Ser Leu Lys Thr
                245                 250                 255

Ala Leu Thr Gly Ala Met Arg Val Thr Lys Asp Thr Asn Asp Asn Asn
            260                 265                 270

Leu Tyr Lys Leu His Gly Gly His Val Ser Cys Arg Val Lys Leu Ser
        275                 280                 285

Ala Leu Thr Leu Lys Gly Thr Ser Tyr Lys Ile Cys Thr Asp Lys Met
    290                 295                 300

Phe Phe Val Lys Asn Pro Thr Asp Thr Gly His Gly Thr Val Val Met
305                 310                 315                 320

Gln Val Lys Val Ser Lys Gly Ala Pro Cys Arg Ile Pro Val Ile Val
                325                 330                 335

Ala Asp Asp Leu Thr Ala Ala Ile Asn Lys Gly Ile Leu Val Thr Val
            340                 345                 350

Asn Pro Ile Ala Ser Thr Asn Asp Asp Glu Val Leu Ile Glu Val Asn
        355                 360                 365
```

```
Pro Pro Phe Gly Asp Ser Tyr Ile Ile Val Gly Arg Gly Asp Ser Arg
    370                 375                 380

Leu Thr Tyr Gln Trp His Lys Glu Gly Ser Ser Ile Gly Lys Leu Phe
385                 390                 395                 400

Thr Gln Thr Met Lys Gly Val Glu Arg Leu Ala Val Met Gly Asp Thr
                405                 410                 415

Ala Trp Asp Phe Ser Ser Ala Gly Gly Phe Phe Thr Ser Val Gly Lys
            420                 425                 430

Gly Ile His Thr Val Phe Gly Ser Ala Phe Gln Gly Leu Phe Gly Gly
        435                 440                 445

Leu Asn Trp Ile Thr Lys Val Ile Met Gly Ala Val Leu Ile Trp Val
450                 455                 460

Gly Ile Asn Thr Arg Asn Met Thr Met Ser Met Ser Met Ile Leu Val
465                 470                 475                 480

Gly Val Ile Met Met Phe Leu Ser Leu Gly Val Gly Ala
                485                 490

<210> SEQ ID NO 2
<211> LENGTH: 495
<212> TYPE: PRT
<213> ORGANISM: Flavivirus dengue virus
<220> FEATURE:
<221> NAME/KEY: misc_feature
<222> LOCATION: (171)..(171)
<223> OTHER INFORMATION: Xaa can be any naturally occurring amino acid

<400> S

-continued

```
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Ile Lys Tyr Glu Gly Thr Asp Ala Pro Cys Lys Ile Pro
                325                 330                 335

Phe Ser Thr Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Ile Gly Ala Gly Glu
    370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Val
            420                 425                 430

Gly Lys Leu Val His Gln Ile Phe Gly Thr Ala Tyr Gly Val Leu Phe
        435                 440                 445

Ser Gly Val Ser Trp Thr Met Lys Ile Gly Ile Gly Val Leu Leu Thr
    450                 455                 460

Trp Leu Gly Leu Asn Ser Arg Ser Thr Ser Leu Ser Met Thr Cys Ile
465                 470                 475                 480

Ala Val Gly Leu Val Thr Leu Tyr Leu Gly Val Met Val Gln Ala
                485                 490                 495
```

```
<210> SEQ ID NO 3
<211> LENGTH: 494
<212> TYPE: PRT
<213> ORGANISM: Flavivirus dengue virus
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid

<400> SEQUENCE: 3

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

```
Glu Ala Lys Gln Pro Ala Thr Leu Arg Lys Tyr Cys Ile Glu Ala Lys
    50                  55                  60
Leu Thr Asn Thr Thr Thr Glu Ser Arg Cys Pro Thr Gln Gly Glu Pro
65                  70                  75                  80
Ser Leu Asn Glu Glu Gln Asp Lys Arg Phe Val Cys Lys His Ser Met
                85                  90                  95
Val Asp Arg Gly Trp Gly Asn Gly Cys Gly Leu Phe Gly Lys Gly Gly
            100                 105                 110
Ile Val Thr Cys Ala Met Phe Thr Cys Lys Lys Asn Met Glu Gly Lys
            115                 120                 125
Xaa Val Gln Pro Glu Asn Leu Glu Tyr Thr Ile Val Ile Thr Pro His
    130                 135                 140
Ser Gly Glu Glu His Ala Val Gly Asn Asp Thr Gly Lys His Gly Lys
145                 150                 155                 160
Glu Ile Lys Ile Thr Pro Gln Ser Ser Ile Thr Glu Ala Glu Leu Thr
                165                 170                 175
Gly Tyr Gly Thr Val Thr Met Glu Cys Ser Pro Arg Thr Gly Leu Asp
            180                 185                 190
Phe Glu Met Val Leu Leu Gln Met Glu Xaa Lys Ala Trp Leu Val His
            195                 200                 205
Arg Gln Trp Phe Leu Asp Leu Pro Leu Pro Trp Leu Pro Gly Ala Asp
    210                 215                 220
Thr Gln Gly Ser Asn Trp Ile Gln Lys Glu Thr Leu Val Thr Phe Lys
225                 230                 235                 240
Asn Pro His Ala Lys Lys Gln Asp Val Val Leu Gly Ser Gln Glu
                245                 250                 255
Gly Ala Met His Thr Ala Leu Thr Gly Ala Thr Glu Ile Gln Met Ser
            260                 265                 270
Ser Gly Asn Leu Leu Phe Thr Gly His Leu Lys Cys Arg Leu Arg Met
    275                 280                 285
Asp Lys Leu Gln Leu Lys Gly Met Ser Tyr Ser Met Cys Thr Gly Lys
    290                 295                 300
Phe Lys Xaa Val Lys Glu Ile Ala Glu Thr Gln His Gly Thr Ile Val
305                 310                 315                 320
Ile Arg Val Gln Tyr Glu Gly Asp Gly Ser Pro Cys Lys Ile Pro Phe
            325                 330                 335
Glu Ile Met Asp Leu Glu Lys Arg His Val Leu Gly Arg Leu Ile Thr
            340                 345                 350
Val Asn Pro Ile Val Thr Glu Lys Asp Ser Pro Val Asn Ile Glu Ala
    355                 360                 365
Glu Pro Pro Phe Gly Asp Ser Tyr Ile Ile Gly Val Glu Pro Gly
    370                 375                 380
Gln Leu Lys Leu Asn Trp Phe Lys Lys Gly Ser Ser Ile Gly Gln Met
385                 390                 395                 400
Phe Glu Thr Thr Met Arg Gly Ala Lys Arg Met Ala Ile Leu Gly Asp
            405                 410                 415
Thr Ala Trp Asp Phe Gly Ser Leu Gly Gly Val Phe Thr Ser Ile Gly
            420                 425                 430
Lys Ala Leu His Gln Val Phe Gly Ala Ile Tyr Gly Ala Ala Phe Ser
            435                 440                 445
Gly Val Ser Trp Thr Met Lys Ile Leu Ile Gly Val Ile Ile Thr Trp
450                 455                 460
Ile Gly Met Asn Ser Arg Ser Thr Ser Leu Ser Val Ser Leu Val Leu
```

```
                465                 470                 475                 480
Val Gly Val Val Thr Leu Tyr Leu Gly Val Met Val Gln Ala
                    485                 490

<210> SEQ ID NO 4
<211> LENGTH: 493
<212> TYPE: PRT
<213> ORGANISM: Flavivirus dengue virus
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid

<400> SEQUENCE: 4

Met Arg Cys Val Gly Val Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Xaa Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
        115                 120                 125

Val Val Gln Tyr Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Pro Gln Ala Ser Thr Thr Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Leu Gly Ser Gln Glu Gly
                245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
        275                 280                 285

Lys Leu Glu Leu Lys Gly Met Ser Tyr Ala Met Cys Thr Asn Thr Phe
    290                 295                 300

Val Leu Lys Lys Glu Val Ser Glu Thr Gln His Gly Thr Ile Leu Ile
```

```
            305                 310                 315                 320
Lys Val Glu Tyr Lys Gly Glu Asp Xaa Pro Cys Lys Ile Pro Phe Ser
                325                 330                 335

Thr Glu Asp Gly Gln Gly Lys Ala His Asn Gly Arg Leu Ile Thr Ala
                340                 345                 350

Asn Pro Val Val Thr Lys Lys Glu Pro Val Asn Ile Glu Ala Glu
                355                 360                 365

Pro Pro Phe Gly Glu Ser Asn Ile Val Ile Gly Ile Gly Asp Asn Ala
370                 375                 380

Leu Lys Ile Asn Trp Tyr Lys Lys Gly Ser Ser Ile Gly Lys Met Phe
385                 390                 395                 400

Glu Ala Thr Ala Arg Gly Ala Arg Arg Met Ala Ile Leu Gly Asp Thr
                405                 410                 415

Ala Trp Asp Phe Gly Ser Val Gly Gly Val Leu Asn Ser Leu Gly Lys
                420                 425                 430

Met Val His Gln Ile Phe Gly Ser Ala Tyr Thr Ala Leu Phe Ser Gly
                435                 440                 445

Val Ser Trp Val Met Lys Ile Gly Ile Gly Val Leu Leu Thr Trp Ile
                450                 455                 460

Gly Leu Asn Ser Lys Asn Thr Ser Met Ser Phe Ser Cys Ile Ala Ile
465                 470                 475                 480

Gly Ile Ile Thr Leu Tyr Leu Gly Ala Val Val Gln Ala
                485                 490

<210> SEQ ID NO 5
<211> LENGTH: 495
<212> TYPE: PRT
<213> ORGANISM: Flavivirus dengue virus

<400> SEQUENCE: 5

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
                20                  25                  30

Thr Met Ala Gln Gly Lys Pro Thr Leu Asp Phe Glu Leu Thr Lys Thr
                35                  40                  45

Thr Ala Lys Glu Val Ala Leu Le

```
Phe Asn Glu Met Ile Leu Met Lys Met Lys Lys Thr Trp Leu Val
    195                 200             205

His Lys Gln Trp Phe Leu Asp Leu Pro Leu Pro Trp Thr Ala Gly Ala
    210                 215             220

Asp Thr Ser Glu Val His Trp Asn Tyr Lys Glu Arg Met Val Thr Phe
225             230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Lys Val Arg
                275                 280             285

Met Glu Lys Leu Arg Ile Lys Gly Met Ser Tyr Thr Met Cys Ser Gly
    290                 295             300

Lys Phe Ser Ile Asp Lys Glu Met Ala Glu Thr Gln His Gly Thr Thr
305             310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Val Ile
                340                 345                 350

Ser Ser Thr Pro Leu Ala Glu Asn Thr Asn Ser Val Thr Asn Ile Glu
            355                 360                 365

Leu Glu Pro Pro Phe Gly Asp Ser Tyr Ile Val Ile Gly Val Gly Asn
    370                 375                 380

Ser Ala Leu Thr Leu His Trp Phe Arg Lys Gly Ser Ser Ile Gly Lys
385                 390                 395                 400

Met Phe Glu Ser Thr Tyr Arg Gly Ala Lys Arg Met Ala Ile Leu Gly
            405                 410                 415

Glu Thr Ala Trp Asp Phe Gly Ser Val Gly Gly Leu Phe Thr Ser Leu
                420                 425                 430

Gly Lys Ala Val His Gln Val Phe Gly Ser Val Tyr Thr Thr Met Phe
            435                 440                 445

Gly Gly Val Ser Trp Met Ile Arg Ile Leu Ile Gly Phe Leu Val Leu
    450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495
```

What is claimed is:

1. A method of vaccinating against Dengue virus infection, comprising the steps of:
providing a vaccine, wherein the vaccine comprises:
a vaccine construct backbone, wherein the vaccine construct backbone is a flavivirus virus envelope protein;
wherein the vaccine comprises at least one substitution at an amino acid disposed at location, and wherein the at least one substitution is disposed at a location correlating to amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of SEQ ID No. 1;
wherein the at least one substitution replaces one or more amino acids of the vaccine construct backbone with at least one corresponding amino acid from a dengue fever virus envelope protein selected from the group consisting of SEQ ID No. 2, SEQ ID No. 3, SEQ ID No. 4, and SEQ ID No. 5; and
administering the vaccine to a patient, wherein the patient is suspectable to dengue viral infection.

2. The method of claim 1, where the vaccine construct backbone is a flavivirus selected from the group consisting of West Nile Virus, St. Louis encephalitis, Dengue Fever virus, Japanese encephalitis, Yellow Fever virus, and Kunjin virus.

3. The method of claim 1, where the flavivirus is yellow fever virus 17-D envelope protein having SEQ ID No. 1.

4. The method of claim 1, wherein the substituted amino acids are disposed adjacent to the E protein fusion loop and are within 5 Å of the fusion loop.

5. The method of claim 1, wherein the substituted amino acids are disposed adjacent to the E protein fusion loop and are within 14 Å of the fusion loop.

6. The method of claim 1, wherein the at least one substitution replaces one or more amino acids of the vaccine construct backbone with at least one corresponding amino acid from a dengue fever virus envelope protein from SEQ ID No. 3.

7. The method of claim 1, further comprising administering a pharmaceutically acceptable excipient concurrently with the vaccine.

8. The method of claim 1, further comprising; providing a vaccine, wherein the vaccine comprises:
a first serotype vaccine, wherein the first serotype vaccine further comprises: a first vaccine construct backbone, wherein the vaccine construct backbone is a flavivirus virus envelope protein; wherein the vaccine comprises at least one substitution at an amino acid disposed at location, and wherein the at least one substitution is disposed at a location correlating to amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of SEQ ID No. 1; wherein the at least one substitution replaces one or more amino acids of the vaccine construct backbone with at least one corresponding amino acid from a dengue fever virus envelope protein selected from the group consisting of SEQ ID No. 2;
a second serotype vaccine, wherein the second serotype vaccine further comprises: a second vaccine construct backbone, wherein the vaccine construct backbone is a flavivirus virus envelope protein;
wherein the vaccine comprises at least one substitution at an amino acid disposed at location, and wherein the at least one substitution is disposed at a location correlating to amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of SEQ ID No. 1; wherein the at least one substitution replaces one or more amino acids of the vaccine construct backbone with at least one corresponding amino acid from a dengue fever virus envelope protein selected from the group consisting of SEQ ID No. 3;
a third serotype vaccine, wherein the third serotype vaccine further comprises: a third vaccine construct backbone, wherein the vaccine construct backbone is a flavivirus virus envelope protein; wherein the vaccine comprises at least one substitution at an amino acid disposed at location, and wherein the at least one substitution is disposed at a location correlating to amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of SEQ ID No. 1; wherein the at least one substitution replaces one or more amino acids of the vaccine construct backbone with at least one corresponding amino acid from a dengue fever virus envelope protein selected from the group consisting of SEQ ID No. 4;
a fourth serotype vaccine, wherein the fourth serotype vaccine further comprises: a fourth vaccine construct backbone, wherein the vaccine construct backbone is a flavivirus virus envelope protein;
wherein the vaccine comprises at least one substitution at an amino acid disposed at an amino acid disposed at location, and wherein the at least one substitution is disposed at a location correlating to amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of SEQ ID No. 1: and wherein the at least one substitution replaces one or more amino acids of the vaccine construct backbone with at least one corresponding amino acid from a dengue fever virus envelope protein selected from the group consisting of SEQ ID No. 5.

9. The method of claim 1, wherein the at least one substitution is disposed at a location correlating to amino acids 101, 107, 109, or a combination thereof.

10. The method of claim 1, further comprising administering an adjuvant concurrently with the vaccine, wherein the adjuvant is alum, virosomes expressing the at least one vaccine construct backbone, or at least one interleukin.

11. The method of claim 10, wherein the at least one interleukin is IL-10, IL-12, TNF-α, TNF-β, or a combination thereof.

12. A method of vaccinating against Dengue virus infection, comprising the steps of:
providing a vaccine, wherein the vaccine comprises:
a vaccine construct backbone, wherein the vaccine construct backbone is a Yellow Fever virus envelope protein;
wherein the vaccine comprises at least one substitution at an amino acid disposed at location, and wherein the at least one substitution is disposed at a location correlating to amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of SEQ ID No. 1;
wherein the at least one substitution replaces one or more amino acids of the vaccine construct backbone with at least one corresponding amino acid from a dengue fever virus envelope protein selected from the group consisting of SEQ ID No. 2, SEQ ID No. 3, SEQ ID No. 4, and SEQ ID No. 5; and
administering the vaccine to a patient, wherein the patient is suspectable to dengue viral infection.

13. The method of claim 12, where the yellow fever virus envelope protein is a YFV 17-D protein having SEQ ID No. 1.

14. The method of claim 12, wherein the substituted amino acids are disposed adjacent to the E protein fusion loop and are within 5 Å of the fusion loop.

15. The method of claim 12, wherein the substituted amino acids are disposed adjacent to the E protein fusion loop and are within 14 Å of the fusion loop.

16. The method of claim 12, wherein the at least one substitution replaces one or more amino acids of the vaccine construct backbone with at least one corresponding amino acid from a dengue fever virus envelope protein from SEQ ID No. 3.

17. The method of claim 12, further comprising administering a pharmaceutically acceptable excipient concurrently with the vaccine.

18. The method of claim 12, further comprising:
providing a vaccine, wherein the vaccine comprises:
a first serotype vaccine, wherein the first serotype vaccine further comprises:
a first vaccine construct backbone, wherein the vaccine construct backbone is a flavivirus virus envelope protein;
wherein the vaccine comprises at least one substitution at an amino acid disposed at location, and wherein the at least one substitution is disposed at a location correlating to amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of SEQ ID No. 1;

wherein the at least one substitution replaces one or more amino acids of the vaccine construct backbone with at least one corresponding amino acid from a dengue fever virus envelope protein selected from the group consisting of SEQ ID No. 2;

a second serotype vaccine, wherein the second serotype vaccine further comprises:

a second vaccine construct backbone, wherein the vaccine construct backbone is a flavivirus virus envelope protein;

wherein the vaccine comprises at least one substitution at an amino acid disposed at location, and wherein the at least one substitution is disposed at a location correlating to amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of SEQ ID No. 1;

wherein the at least one substitution replaces one or more amino acids of the vaccine construct backbone with at least one corresponding amino acid from a dengue fever virus envelope protein selected from the group consisting of SEQ ID No. 3;

a third serotype vaccine, wherein the third serotype vaccine further comprises:

a third vaccine construct backbone, wherein the vaccine construct backbone is a flavivirus virus envelope protein;

wherein the vaccine comprises at least one substitution at an amino acid disposed at location, and wherein the at least one substitution is disposed at a location correlating to amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of SEQ ID No. 1;

wherein the at least one substitution replaces one or more amino acids of the vaccine construct backbone with at least one corresponding amino acid from a dengue fever virus envelope protein selected from the group consisting of SEQ ID No. 4;

a fourth serotype vaccine, wherein the fourth serotype vaccine further comprises:

a fourth vaccine construct backbone, wherein the vaccine construct backbone is a flavivirus virus envelope protein;

wherein the vaccine comprises at least one substitution at an amino acid disposed at location, and wherein the at least one substitution is disposed at a location correlating to amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of SEQ ID No. 1; and wherein the at least one substitution replaces one or more amino acids of the vaccine construct backbone with at least one corresponding amino acid from a dengue fever virus envelope protein selected from the group consisting of SEQ ID No. 5.

19. The method of claim 12, further comprising administering an adjuvant concurrently with the vaccine, wherein the adjuvant is alum, virosomes expressing the at least one vaccine construct backbone, or at least one interleukin.

20. The method of claim 19, wherein the at least one interleukin is IL-10, IL-12, TNF-$\alpha$, TNF-$\beta$, or a combination thereof.

* * * * *